United States Patent
Finger et al.

(10) Patent No.: US 12,337,193 B2
(45) Date of Patent: Jun. 24, 2025

(54) APPLICATOR WITH A RADIATION SOURCE WITHIN A MODULE FOR TREATING TISSUE HAVING ENHANCED VISUALIZATION AND RADIATION SHIELDING CAPABILITIES

(71) Applicant: IP LIBERTY VISION CORPORATION, Suite 5B, NY (US)

(72) Inventors: Paul T. Finger, New York, NY (US); Toby Welles, New York, NY (US)

(73) Assignee: IP LIBERTY VISION CORPORATION, New York, NY (US)

( * ) Notice: Subject to any disclaimer, the term of this patent is extended or adjusted under 35 U.S.C. 154(b) by 0 days.

(21) Appl. No.: 19/009,968

(22) Filed: Jan. 4, 2025

(65) Prior Publication Data

US 2025/0144446 A1    May 8, 2025

Related U.S. Application Data

(63) Continuation of application No. 18/346,819, filed on Jul. 4, 2023, now Pat. No. 12,186,584.

(51) Int. Cl.
*A61N 5/00* (2006.01)
*A61N 5/10* (2006.01)

(52) U.S. Cl.
CPC .... *A61N 5/1028* (2013.01); *A61N 2005/1024* (2013.01)

(58) Field of Classification Search
CPC ...... A61N 5/10; A61N 5/1001; A61N 5/1017; A61N 5/1028; A61N 2005/1019; A61N 2005/1024
See application file for complete search history.

(56) References Cited

U.S. PATENT DOCUMENTS

| | | | |
|---|---|---|---|
| 3,840,015 A | 10/1974 | Gain | |
| 6,443,881 B1 * | 9/2002 | Finger | A61N 5/0601 600/1 |

(Continued)

FOREIGN PATENT DOCUMENTS

| | | |
|---|---|---|
| WO | 2014/074712 A1 | 5/2014 |
| WO | 2015/102800 A1 | 7/2015 |

OTHER PUBLICATIONS

WIPO, International Preliminary Report on Patentability (IPRP) for PCT App. No. PCT/US14/68471 dated Jul. 5, 2018, and International Search Report (ISR) of Feb. 26, 2015 (PCT Pub. App. No, 2015/102800).

(Continued)

*Primary Examiner* — Samuel G Gilbert
(74) *Attorney, Agent, or Firm* — SMITH TEMPEL; Steven P. Wigmore

(57) ABSTRACT

A therapeutic applicator and method may include a wand portion and a module coupled to the wand portion. The module may have a body section and a recess positioned within the body section. The body section may include a prismatic member made of a transparent material and the body section may further include a convex surface. The convex surface may provide a magnification of a view that includes a region surrounding the recess. A radiation source may be positioned within the recess. The body section may have a thickness greater than a diameter of the radiation source which is sufficient to attenuate radiation being emitted from the radiation source while the transparent material of the body section allows visibility of a treatment site that is adjacent to the radiation source. The magnification of the view may fall in range between about 1.1 times to 50.0 times an unmagnified view.

20 Claims, 35 Drawing Sheets

(56) References Cited

U.S. PATENT DOCUMENTS

| | | |
|---|---|---|
| 8,414,467 B2 | 4/2013 | Finger |
| 9,165,692 B2 | 10/2015 | Finger et al. |
| 9,827,444 B2 | 11/2017 | Finger et al. |
| 10,117,578 B2 | 11/2018 | Finger et al. |
| 10,384,078 B2 | 8/2019 | Finger et al. |
| 10,406,026 B2 | 9/2019 | Simaan et al. |
| 11,045,351 B2 | 6/2021 | Finger et al. |
| 11,046,586 B2 | 6/2021 | Leupold et al. |
| 11,147,443 B2 | 10/2021 | Tesar |
| 2004/0138515 A1 | 7/2004 | White et al. |
| 2007/0263375 A1 | 11/2007 | Birkenbach |
| 2008/0119686 A1 | 5/2008 | Finger |
| 2011/0077468 A1 | 3/2011 | Finger |
| 2015/0105605 A1 | 4/2015 | Finger et al. |
| 2016/0184605 A1 | 6/2016 | Roberts et al. |
| 2019/0344096 A1 | 11/2019 | Finger et al. |
| 2022/0212032 A1* | 7/2022 | Marsteller ............ A61N 5/1007 |

OTHER PUBLICATIONS

IP Liberty Vision Corporation, IWAND—Internet Webpage: [https://libertyvision.com/iwand-a/ ], three pages, accessed Jan. 2021.

Kirwan. J.F. "Bela Irradiation: new uses for an old treatment: a review" 2003, Eye (Nature publishing group), 17, pp. 207-215.

Relaed Copending U.S. Appl. No. 17/827,062, filed May 27, 2022; First Named Inventor: Paul T. Finger et al.; Confirmation No. 2590; Application Title: An Applicator With a Radiation Source Within a Module for Treating Tissue Having Visualization and Radiation Shielding Capabilities; Unpublished as of This Date (Nov. 1, 2022).

\* cited by examiner

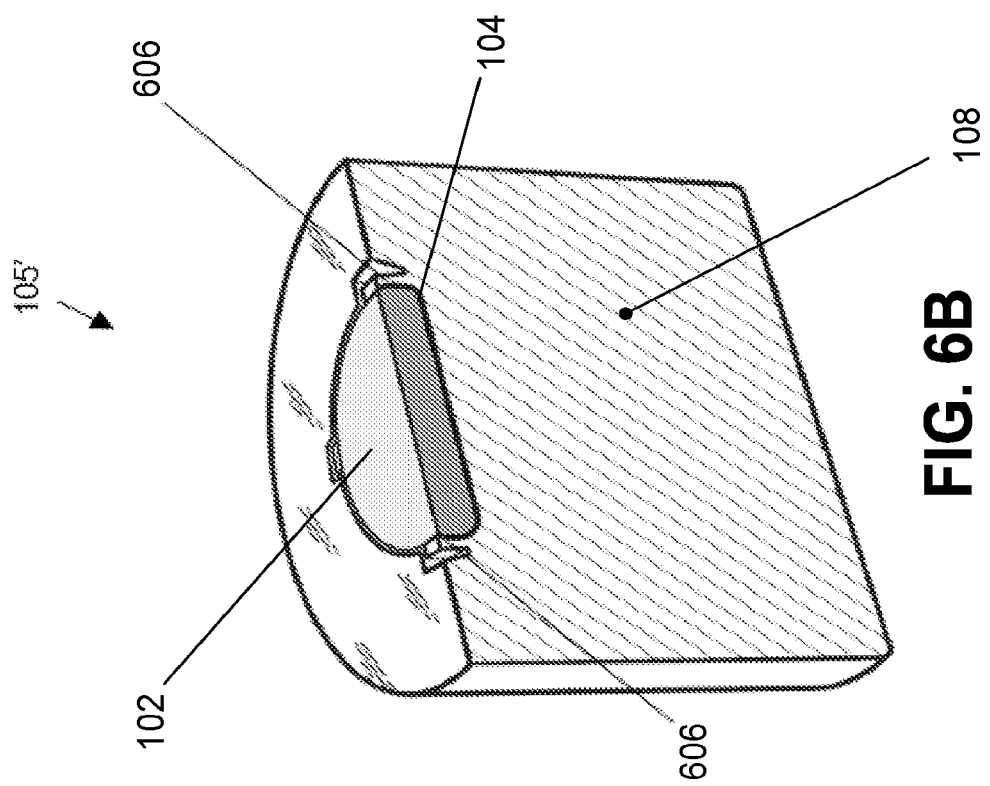
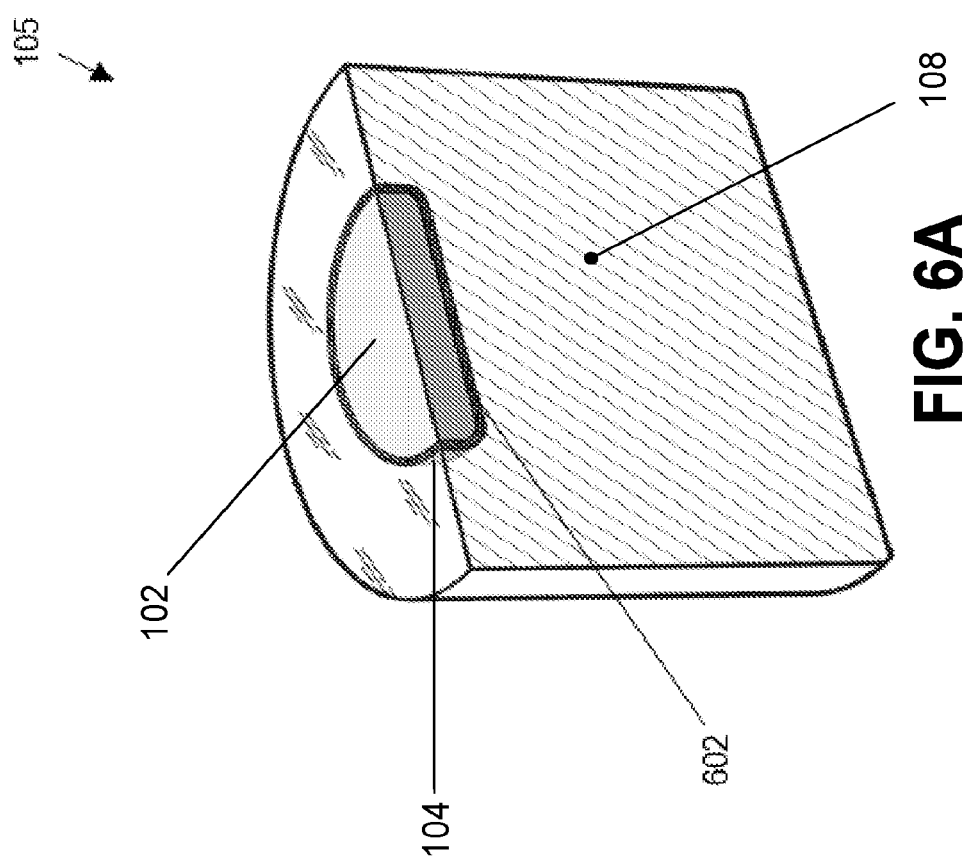
FIG. 6A
FIG. 6B

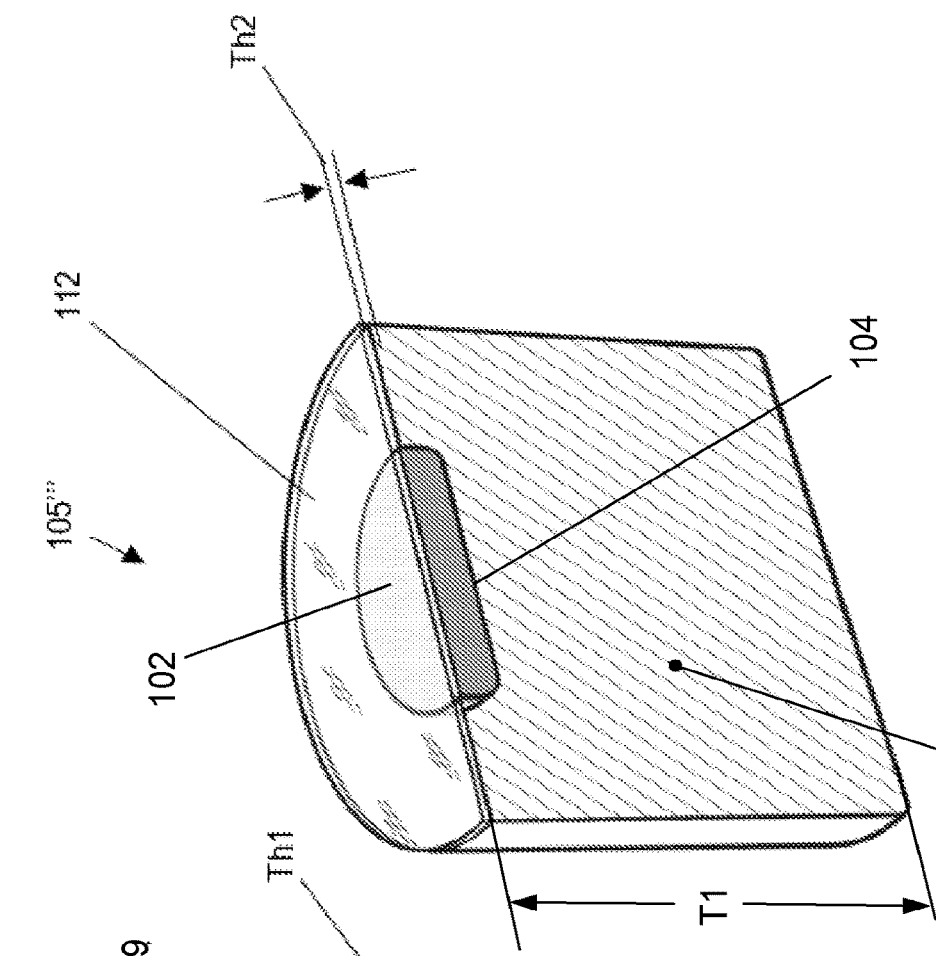
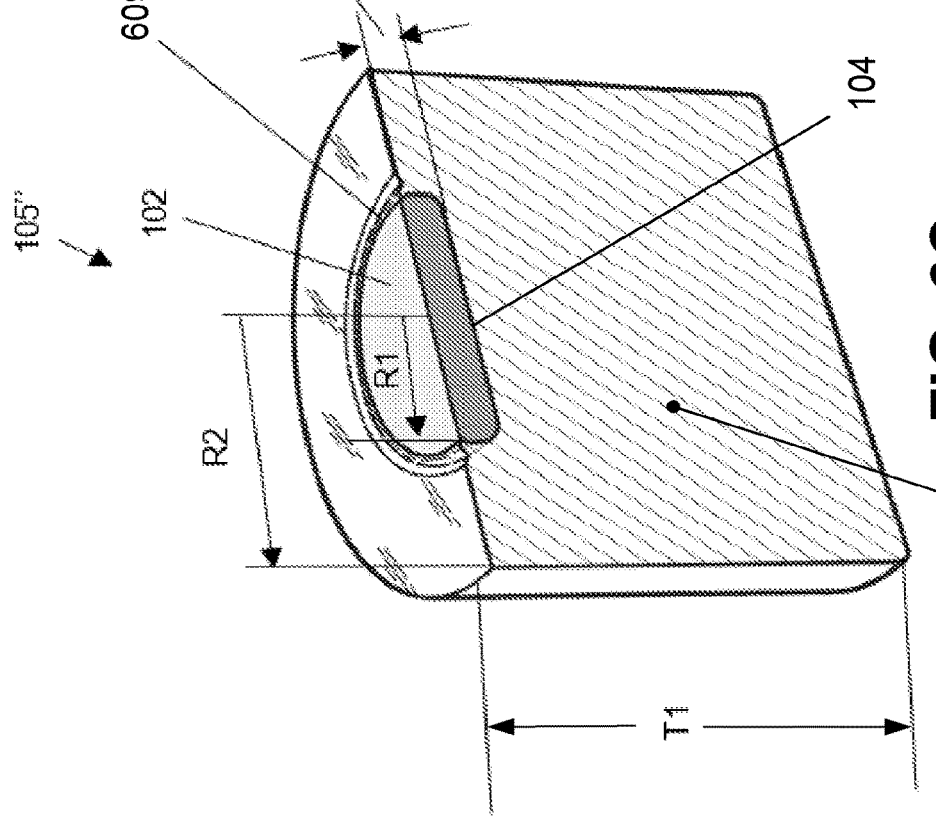
FIG. 6C
FIG. 6D

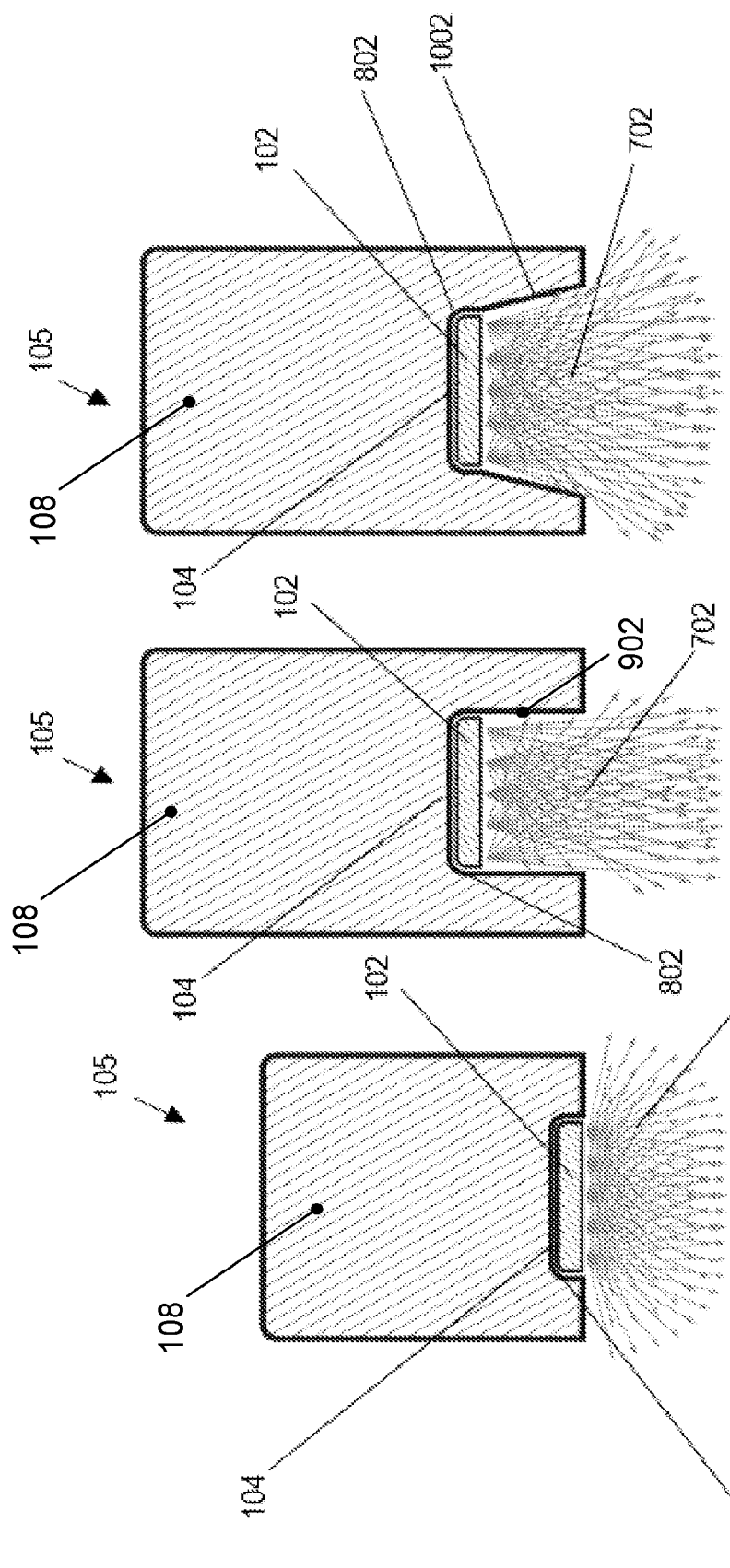

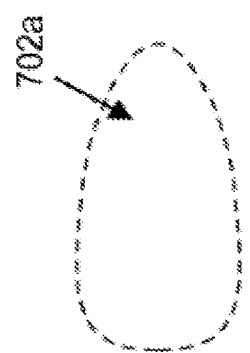
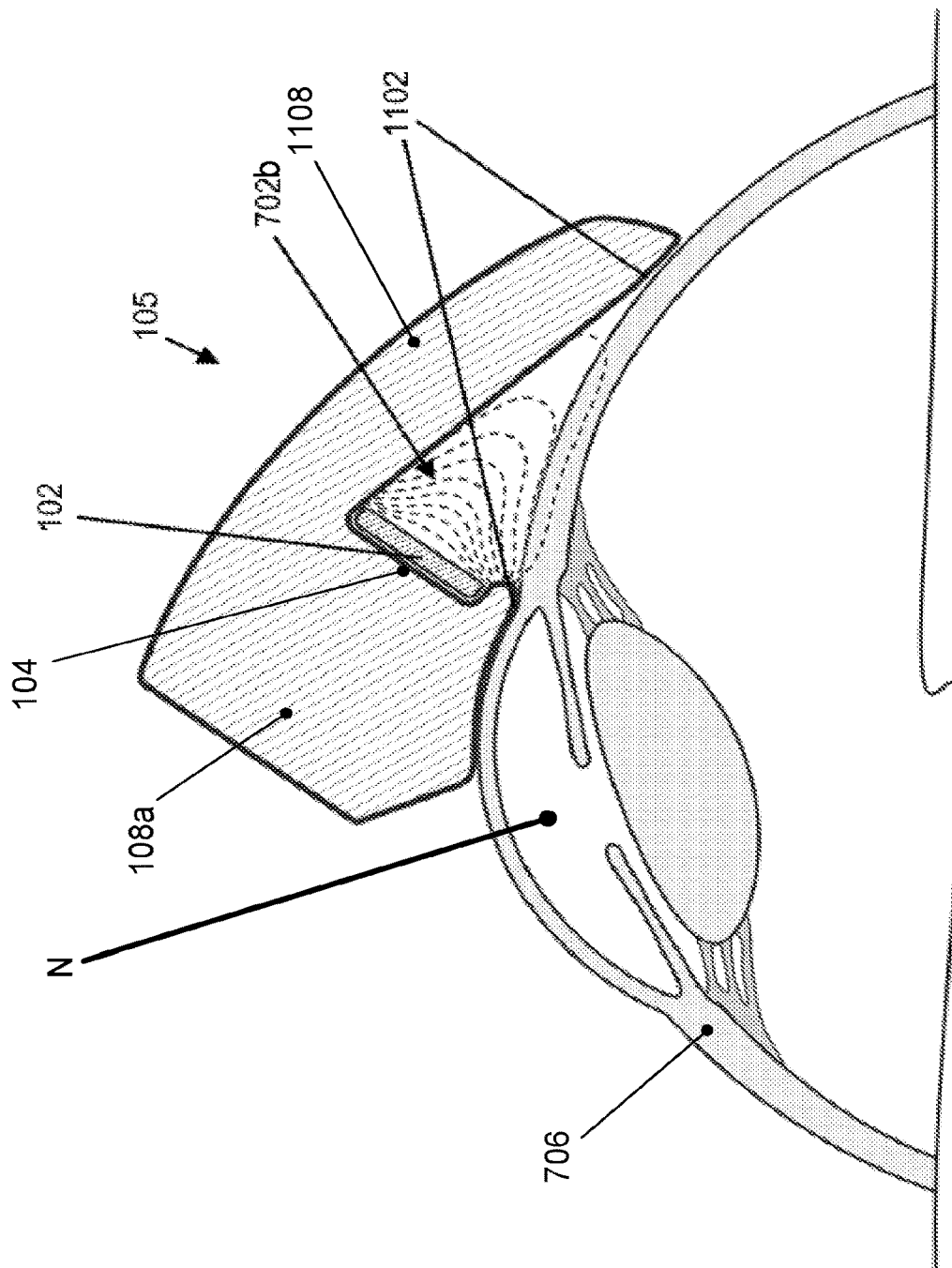
FIG. 12
FIG. 11

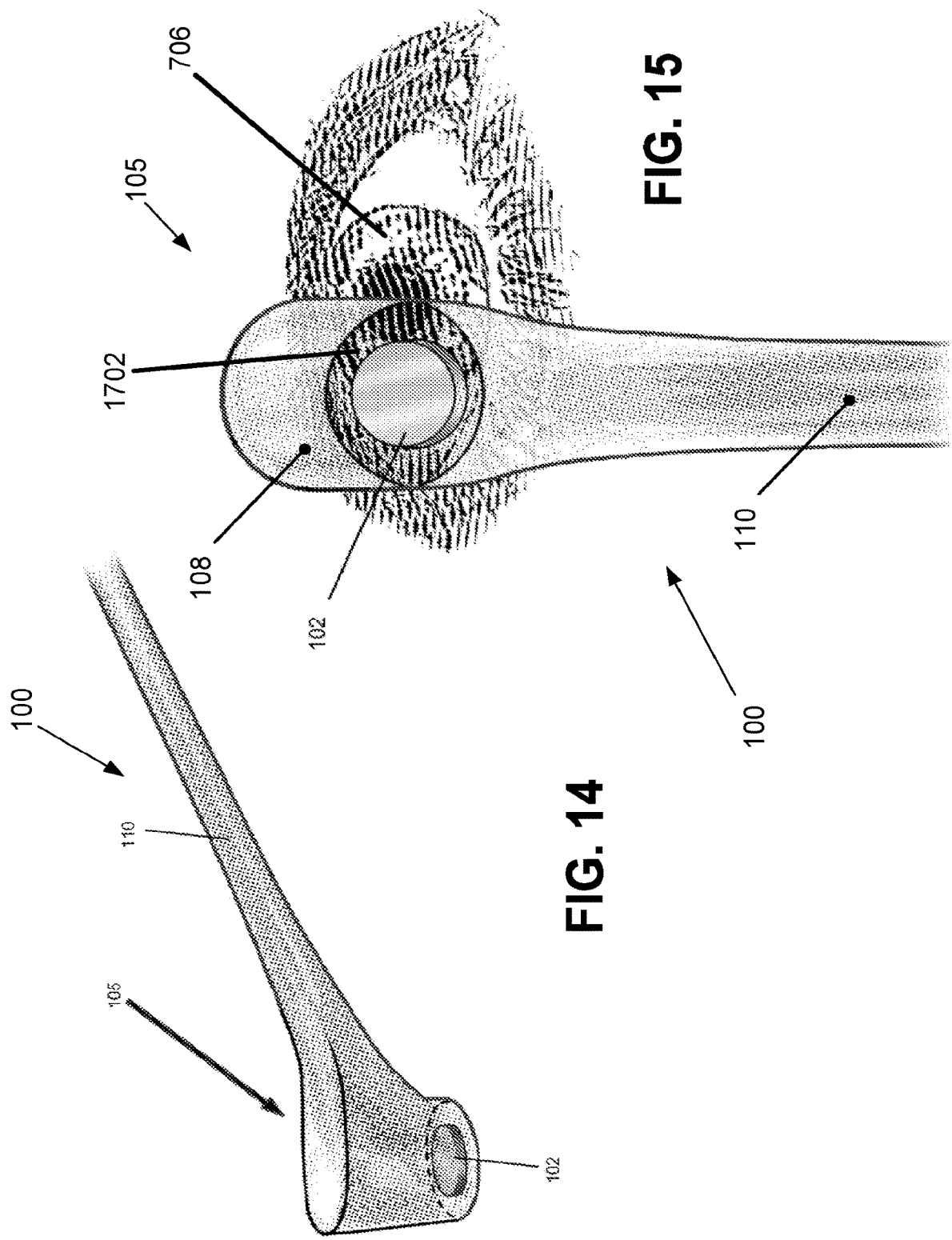

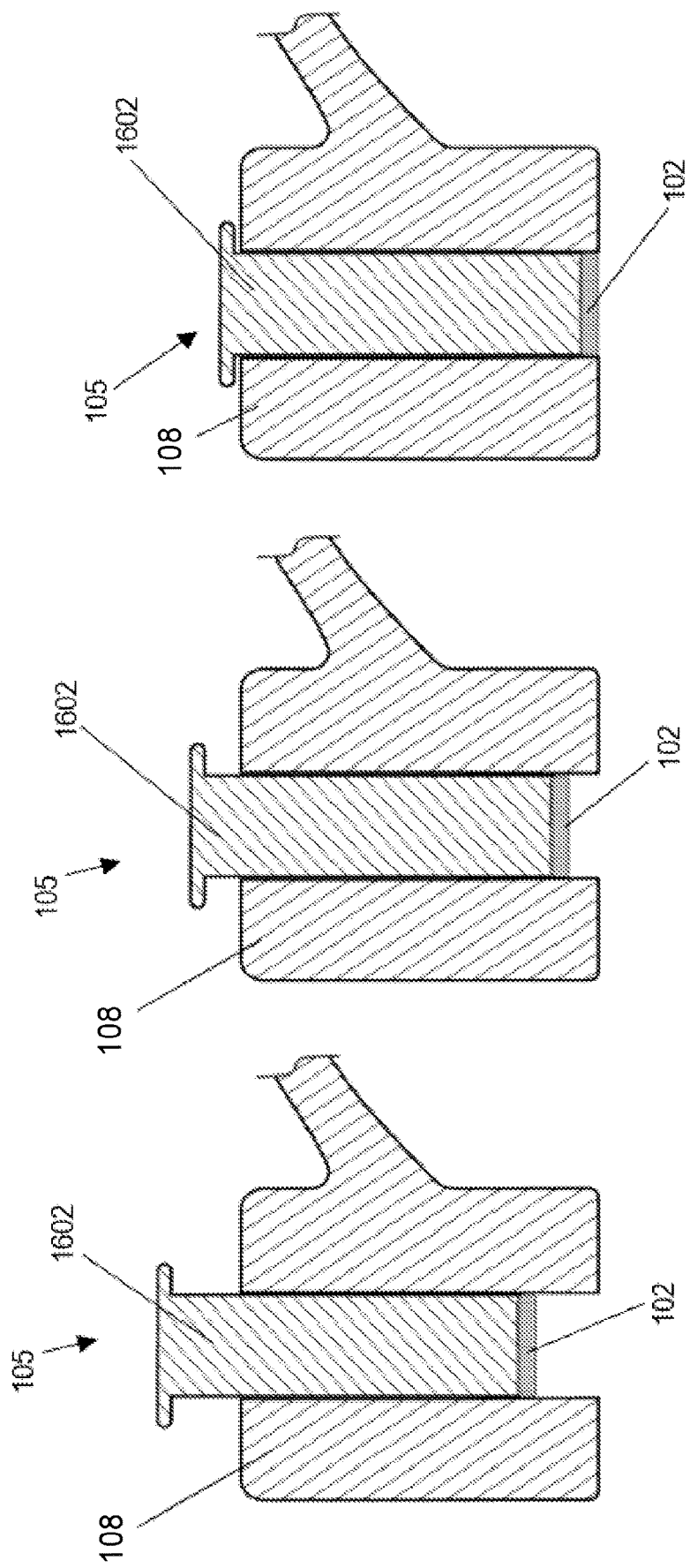

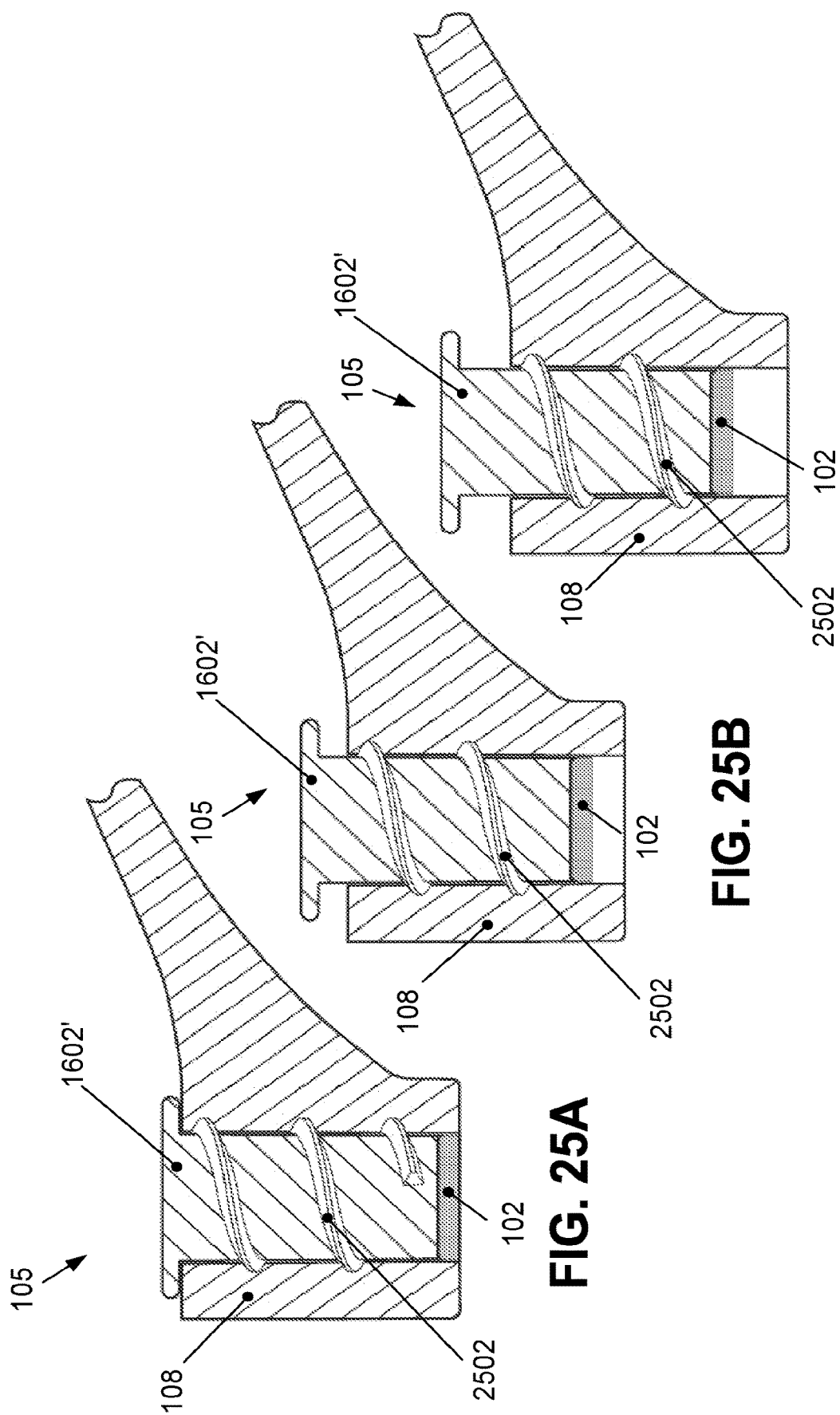

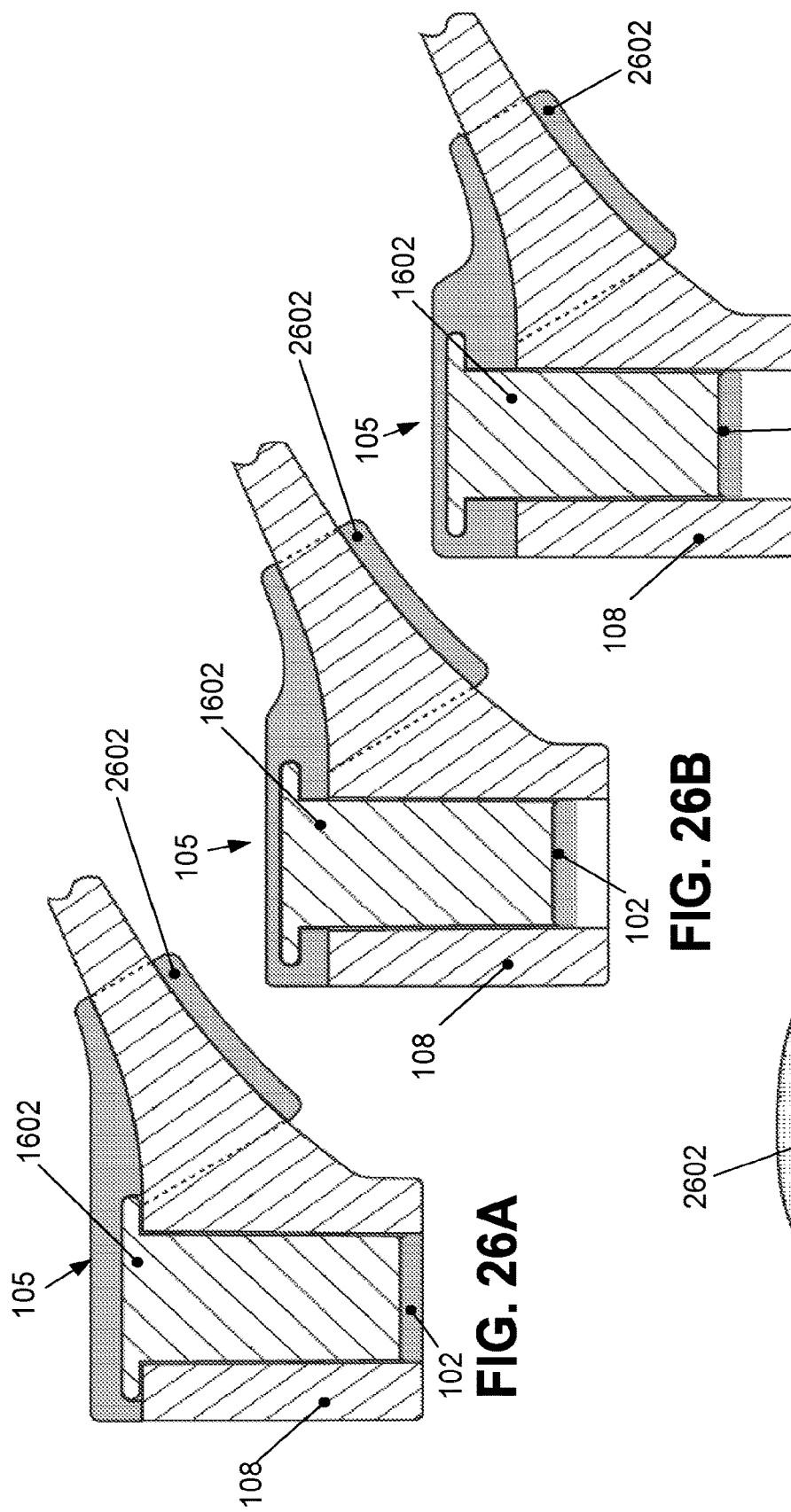

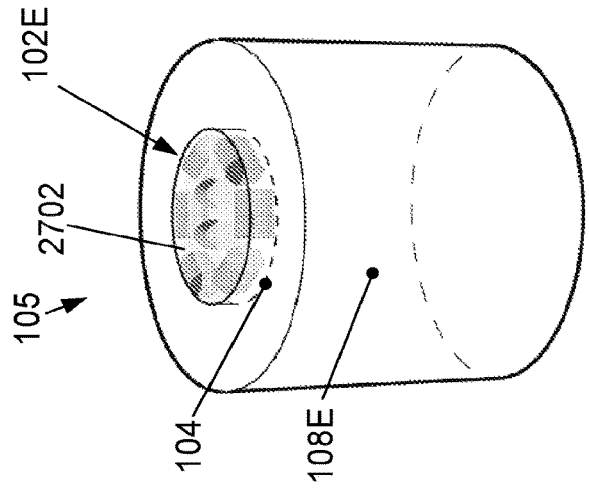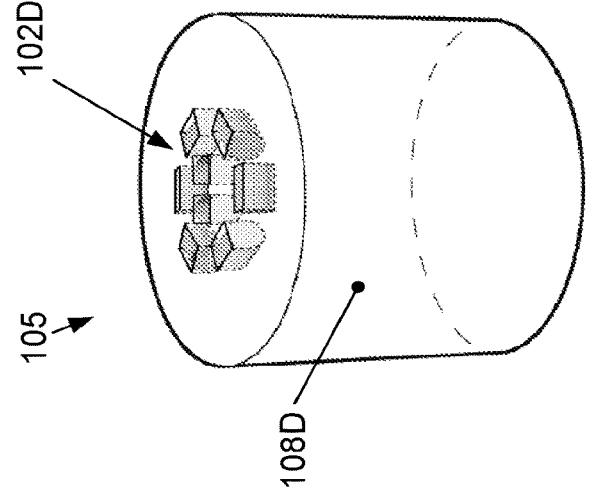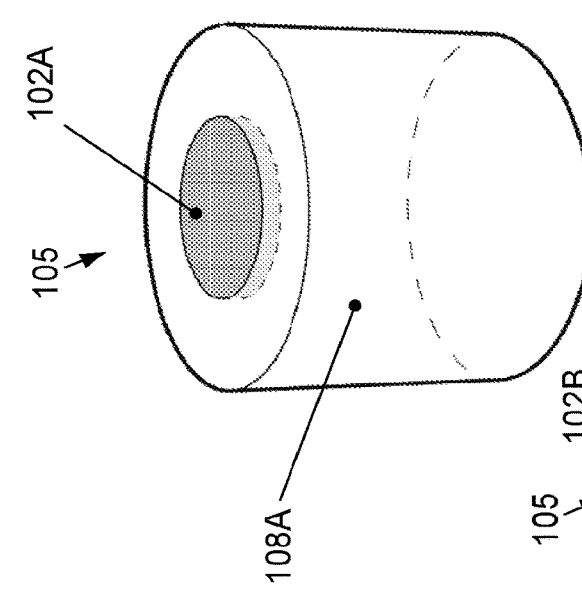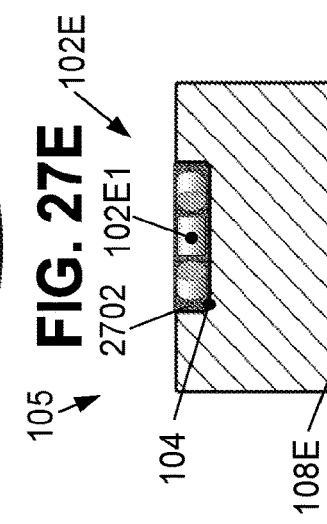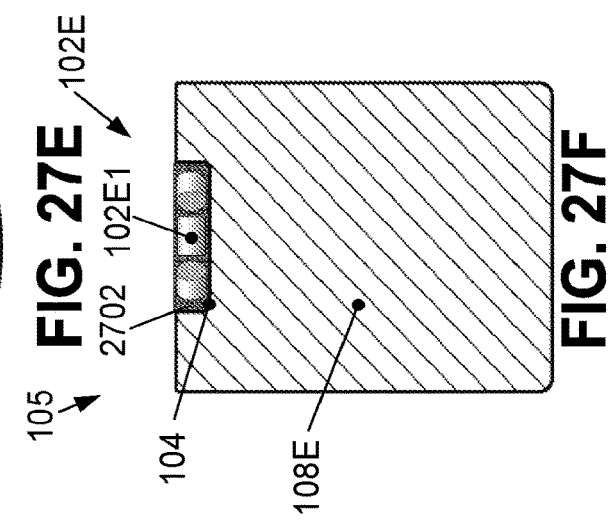

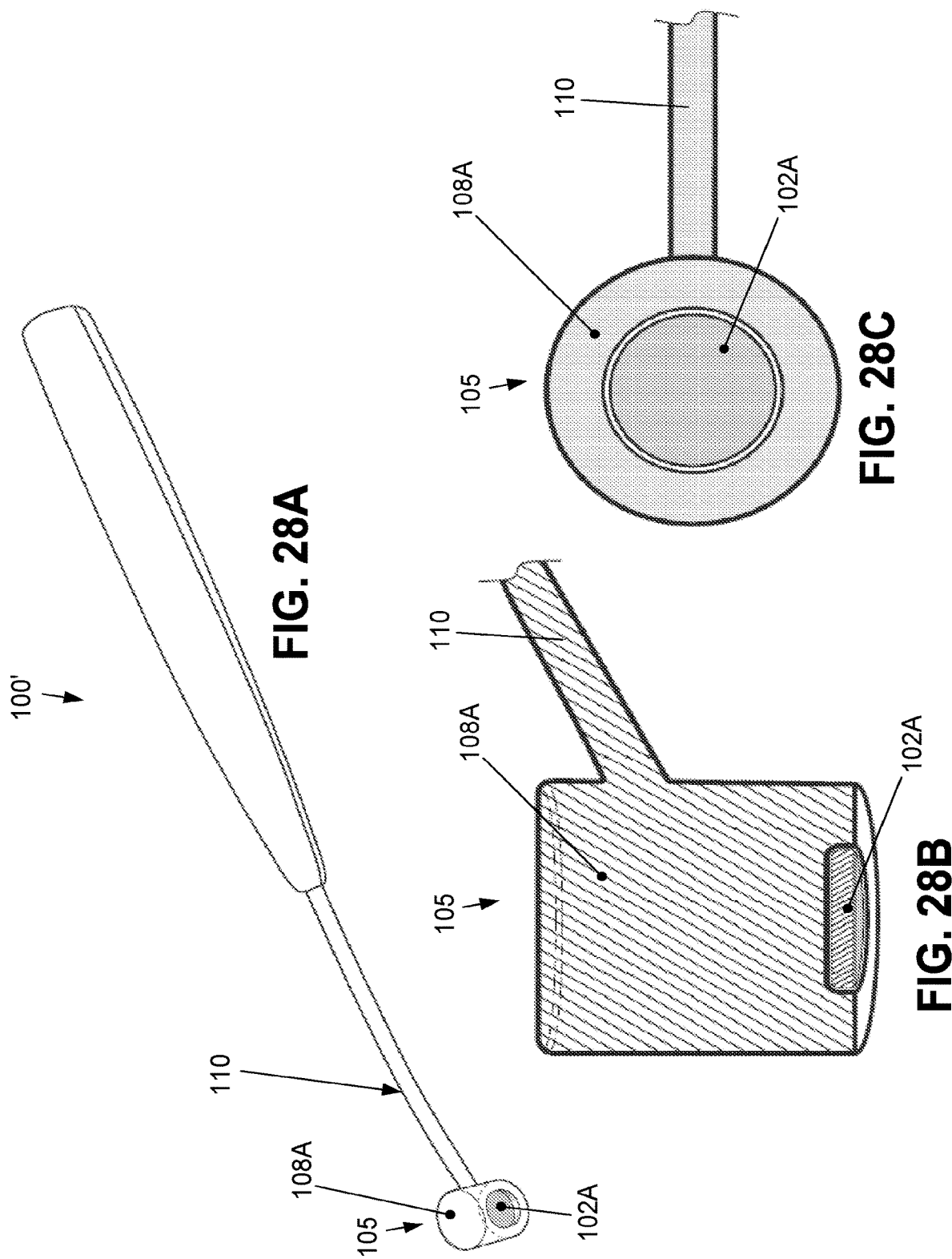

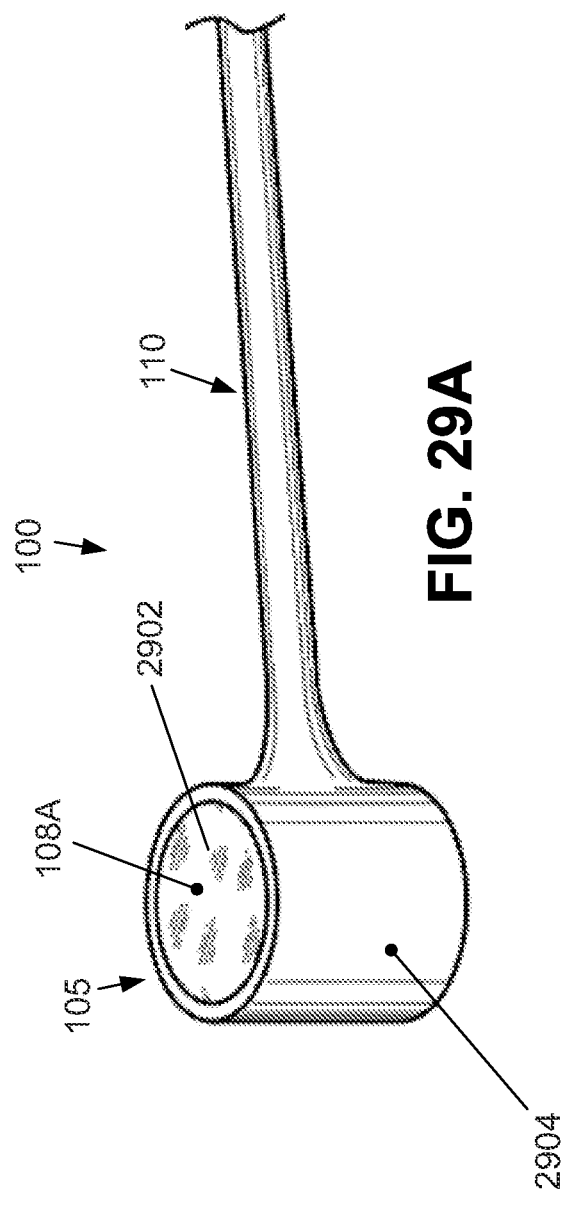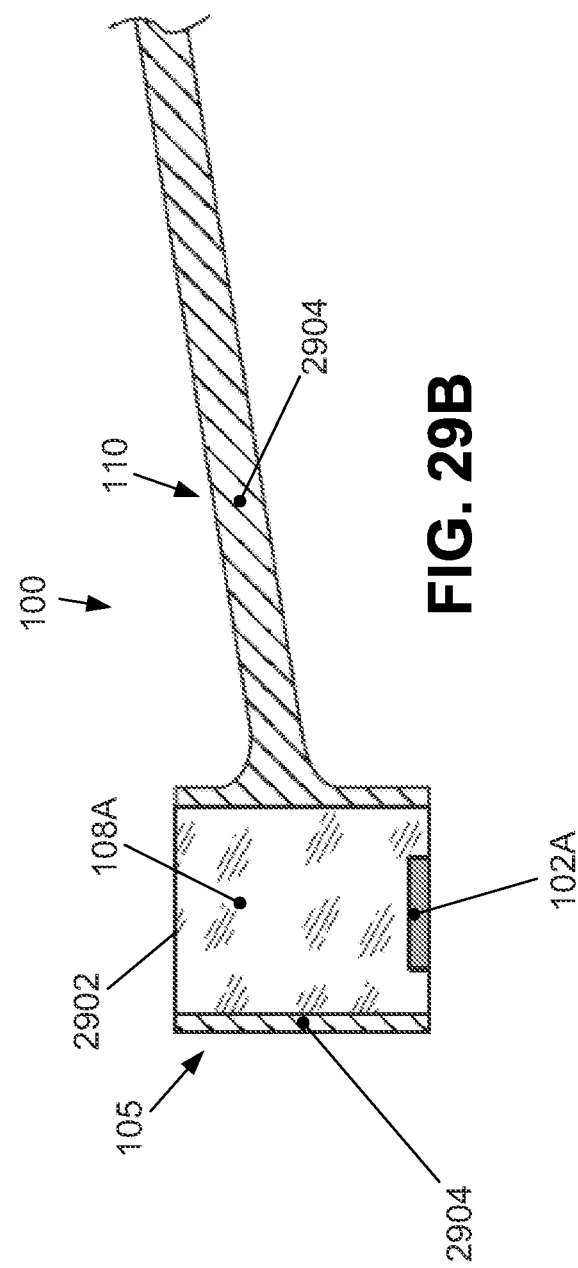

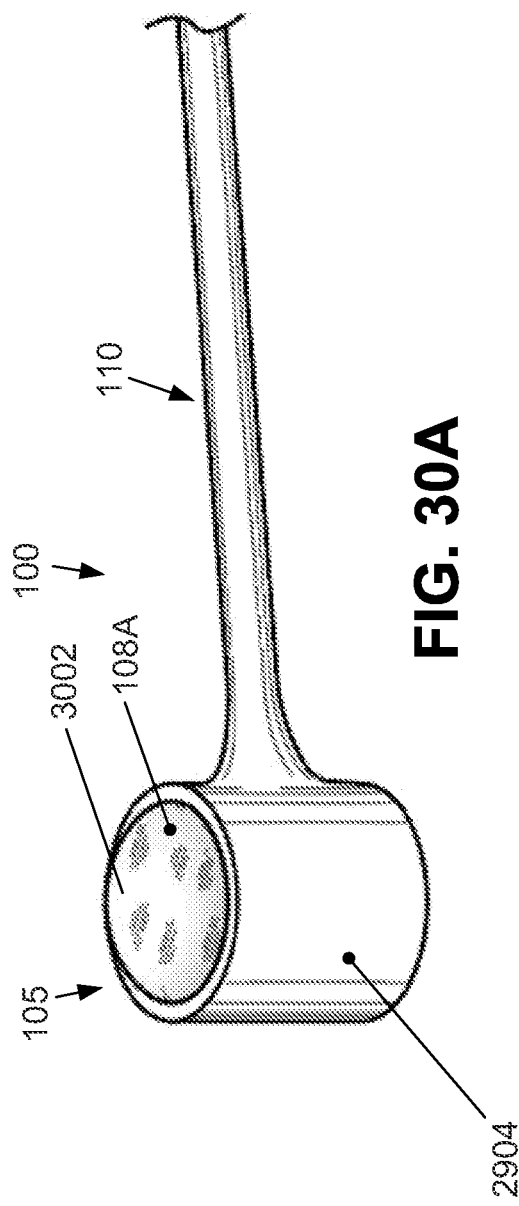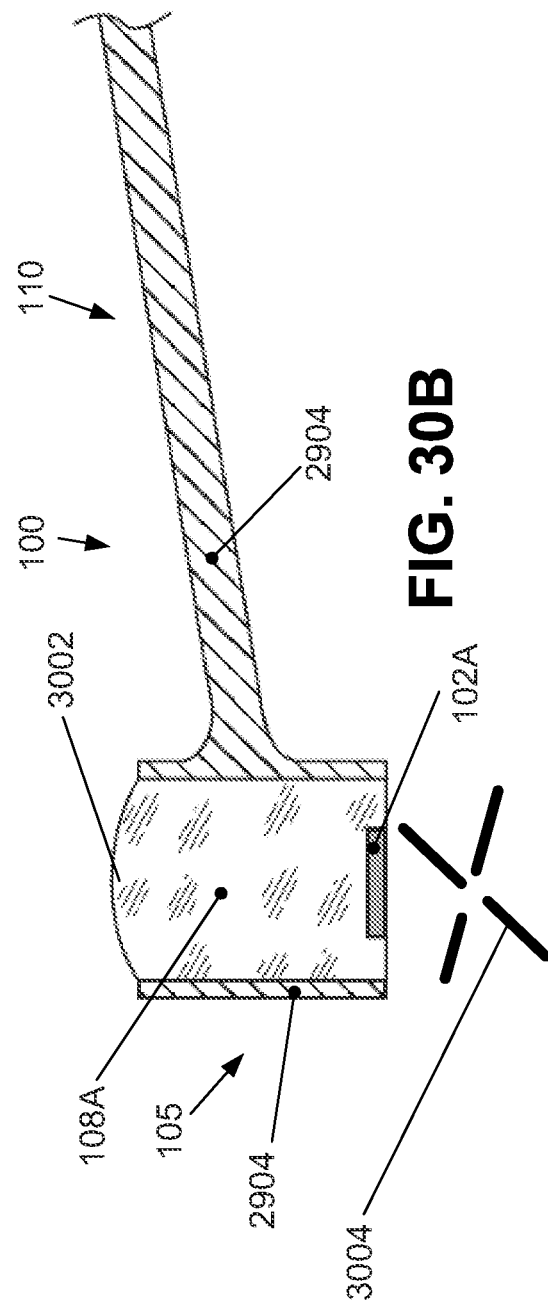

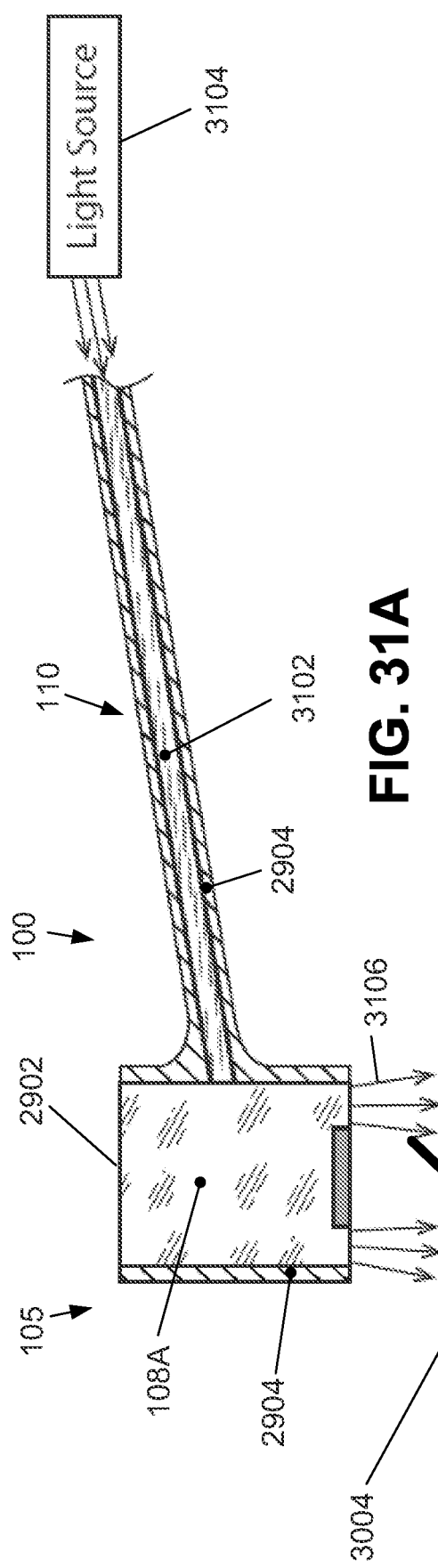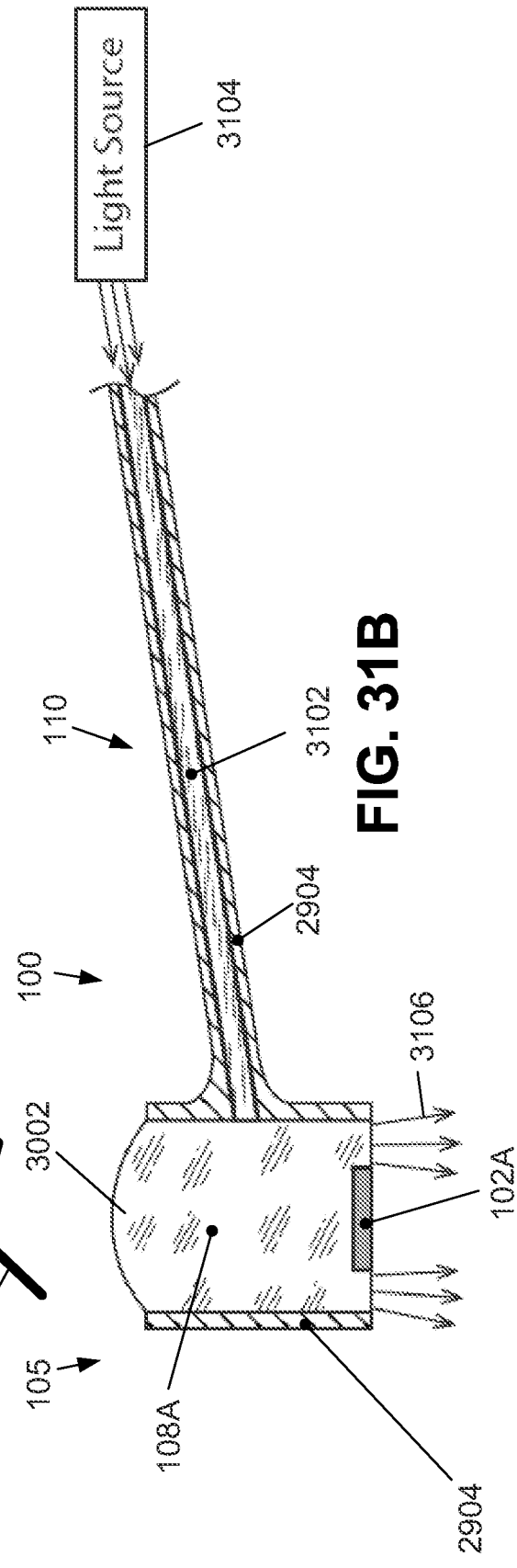

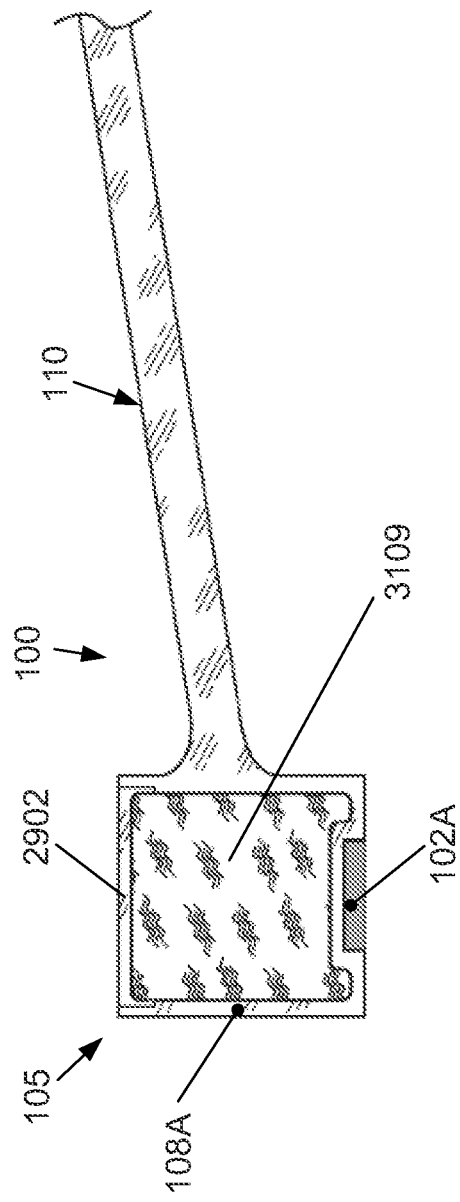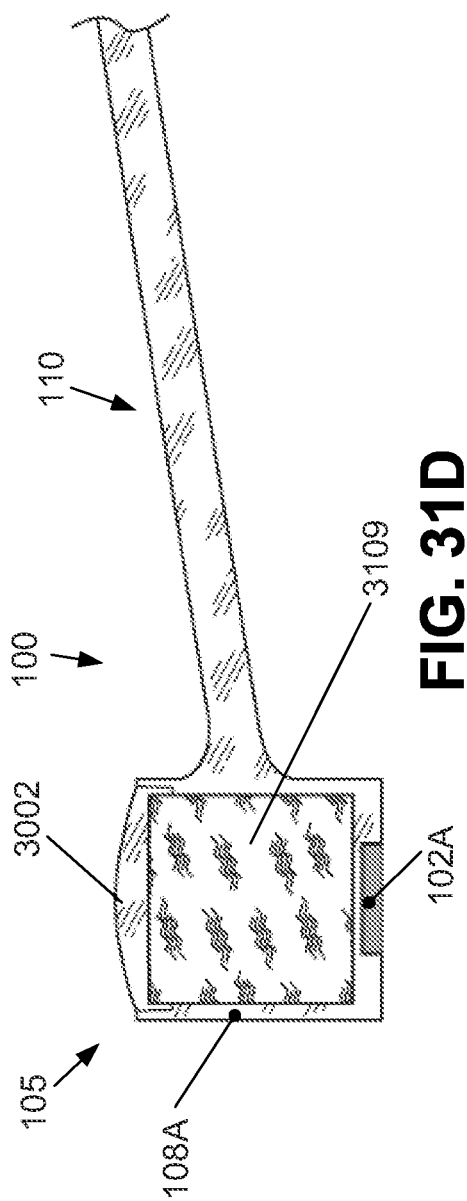

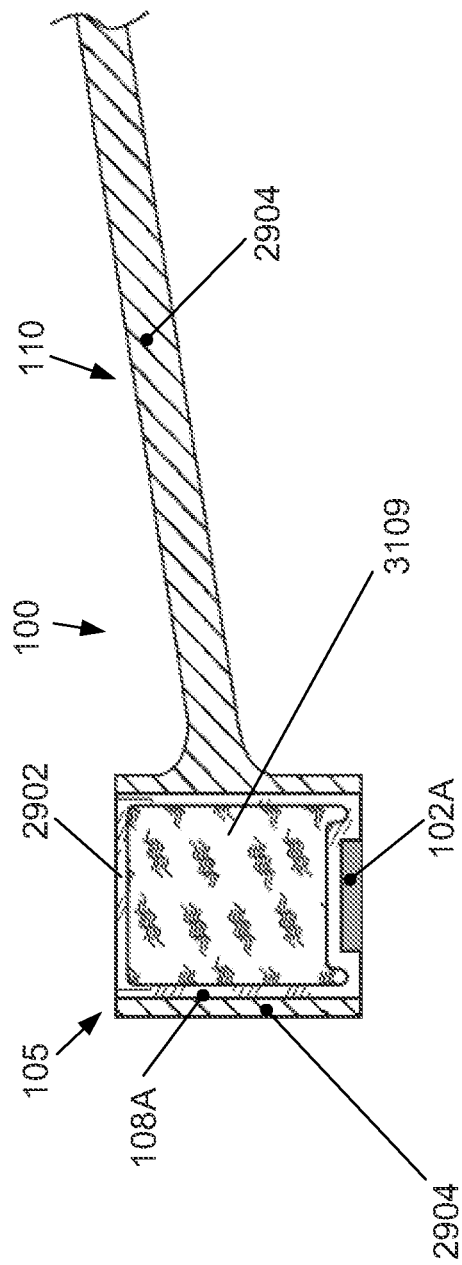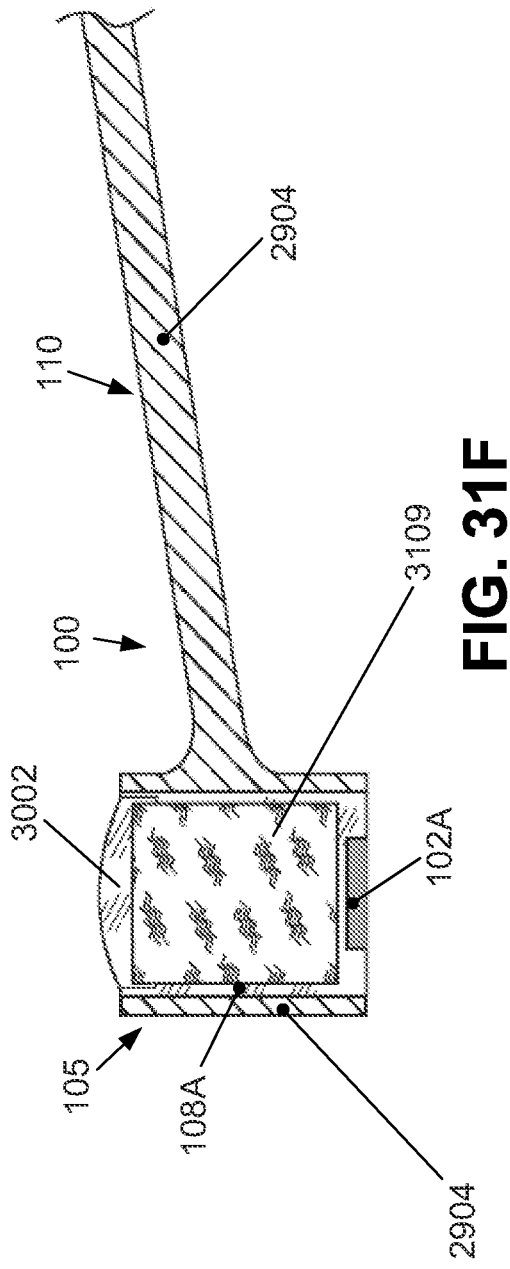

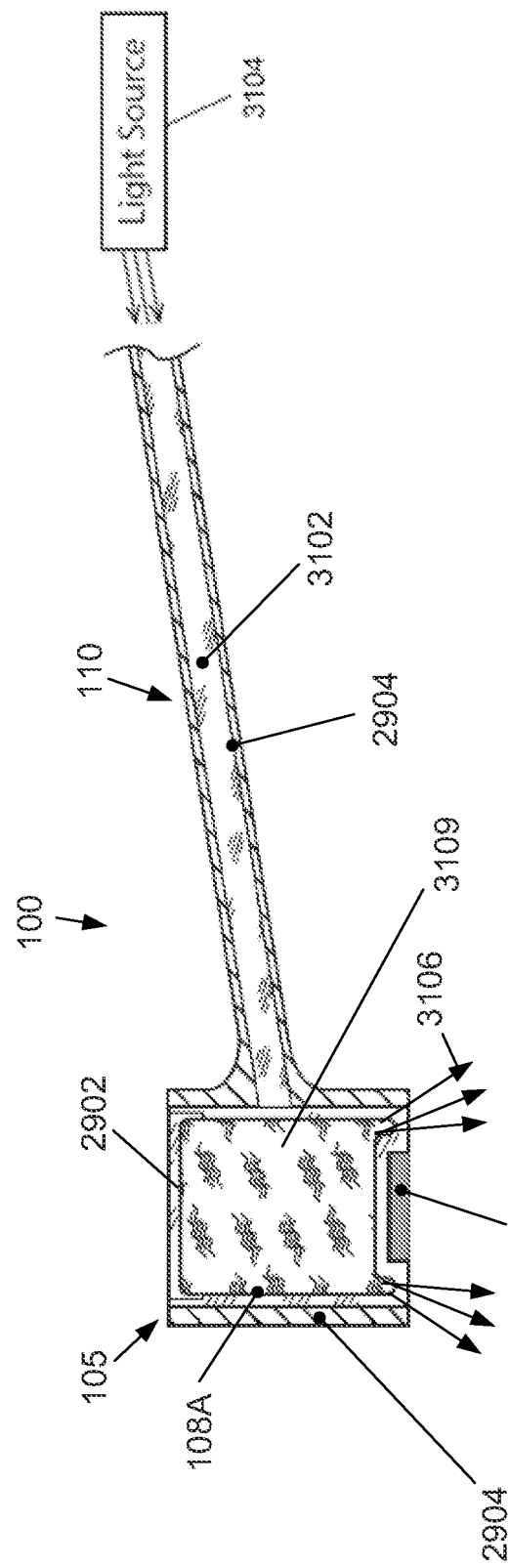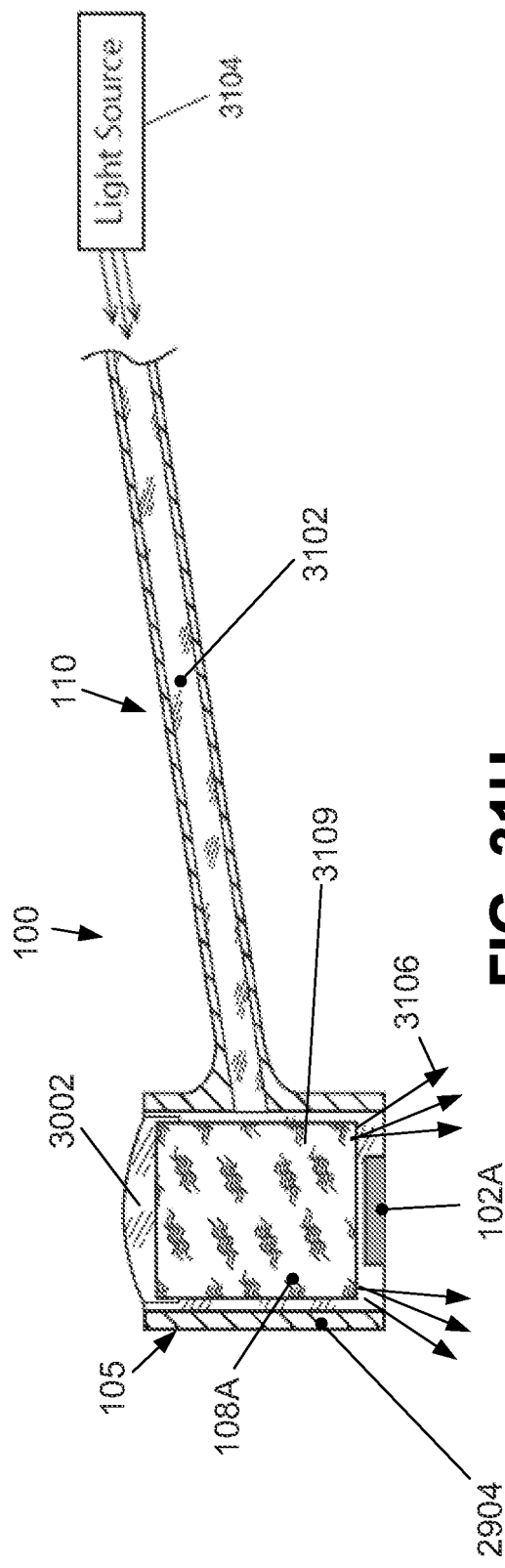

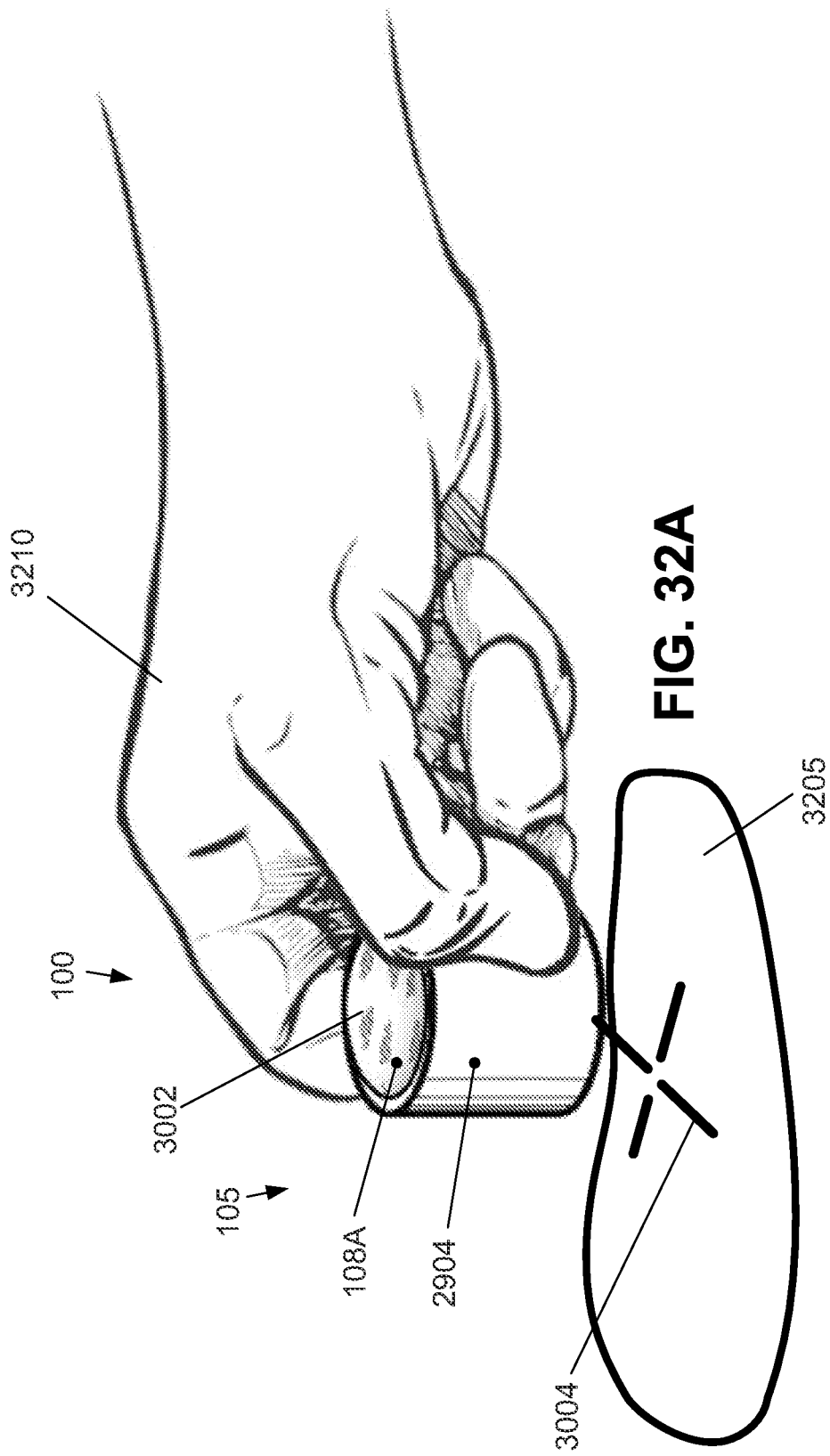

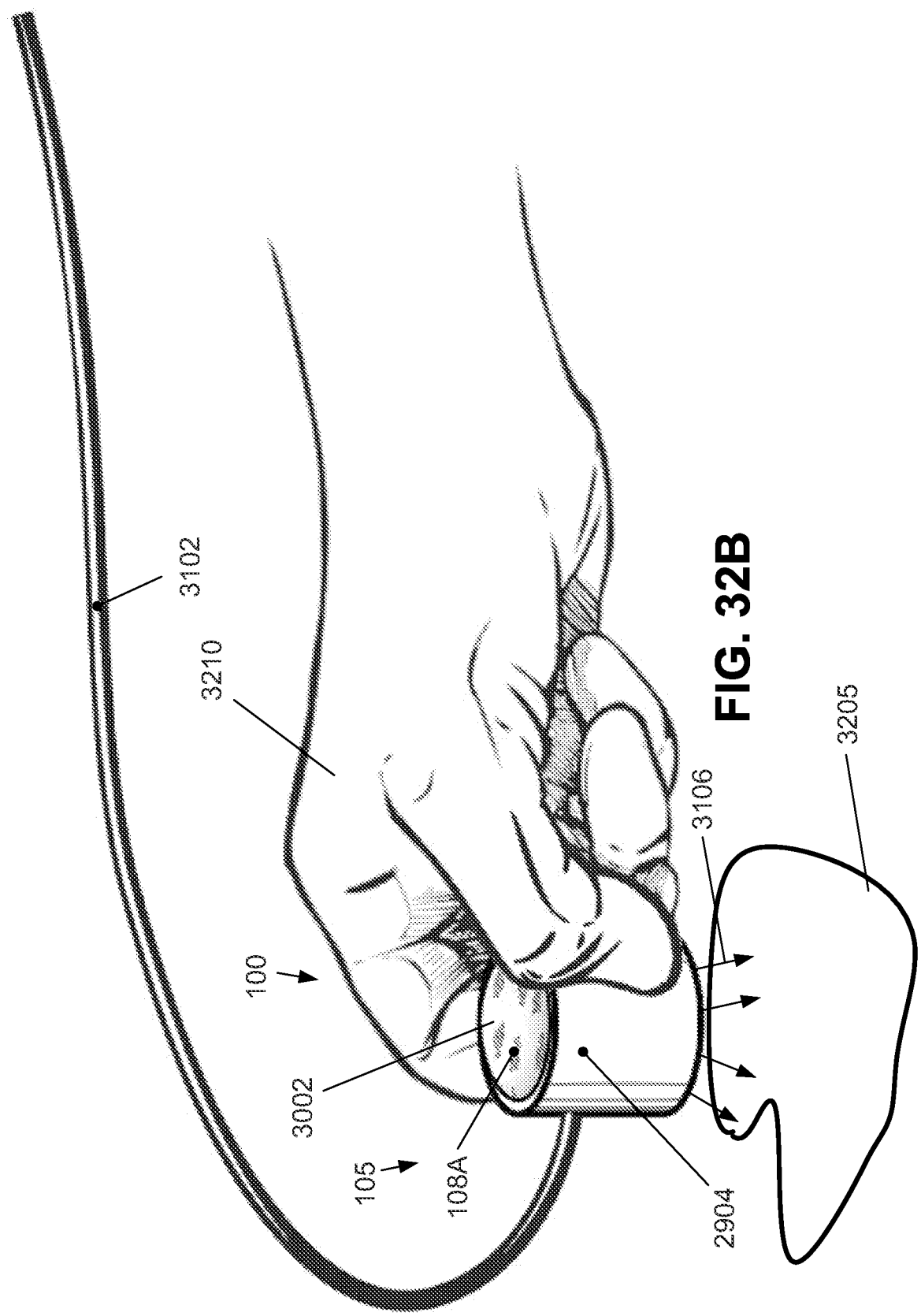

APPLICATOR WITH A RADIATION SOURCE WITHIN A MODULE FOR TREATING TISSUE HAVING ENHANCED VISUALIZATION AND RADIATION SHIELDING CAPABILITIES

BACKGROUND

Brachytherapy is a form of radiation therapy where a source of radiation is placed near or in contact with the tissue treatment site. This method of radiation application has been used as treatment for a variety of tumors, benign and malignant growths. In brief, brachytherapy has limited penetration in tissues which results in localized irradiation to the targeted treatment volume with relative sparing of surrounding tissues. However, brachytherapy sources currently require site-specific applicators to place or insert sources on or in targeted tissues.

Eye treatments include, but are not limited to, irradiation of tumors, benign growths, as well as irradiation of tissues to prevent post-traumatic scarification following surgical procedures. In ophthalmology, the latter include (but are not limited to) methods to surgically create ocular fluid outflow channels (aqueous shunts) and to prevent pterygium regrowth.

One prior art device was the Amersham Strontium-90 ($^{90}$Sr/$^{90}$Y) beta-irradiation applicator. In that device, the radiation source $^{90}$Sr is in secular equilibrium with its daughter $^{90}$Y. No longer in production as of the date of this disclosure, this device included a disc-shaped radionuclide metal source encased at the end of its steel housing. The thin, most distal surface of the housing acts as an aperture for radiation emission. When placed in contact with the targeted tissue, the radiation is absorbed over a prescribed period of time. The metal casing around and proximal to the aperture having greater thickness, attenuates the radiation and thus provides relative shielding of surrounding tissue, surgeons, and other operating room personnel. The system appears as a rod-shaped hand-held applicator that, along its shaft, incorporates a disc-shaped shield for the practitioner.

Several disadvantages to this prior art applicator exist: First, with the device being made of metal, this applicator is heavy. This leads to operator fatigue during use, affecting surgical control and accuracy of placement. Second, the configuration of such metal applicators is ergonomically awkward since their form has been driven by what shapes are easily machinable. This results in difficulty holding them in position properly and over the time durations required for treatment. Third, the $^{90}$Sr/$^{90}$Y source within these metal applicators emits beta radiation which interacts with its high-impedance (Z) metal casing to produce unwanted high-energy x-rays known as bremsstrahlung.

However, high energy bremsstrahlung "braking radiation" is created when beta particles interact with all solids. The more abruptly the particles are forced to slow, the more bremsstrahlung x-rays are created. Thus, high-density materials such as metals generate more high-energy x-rays compared to low-density materials such as plastics and fluids, such as water. These latter materials absorb the beta radiation energy more slowly and thus produce fewer bremsstrahlung x-rays. Another problem with the prior art applicator is visibility: specifically, the opaque and bulky metal shielding that surrounds the beta source, used to construct the distal tip of the prior art's device, impedes the ability of the practitioner to view and thus accurately position and monitor the radiation source placement during treatment.

Accordingly, there is a need in the art for a device that is easier for the medical practitioner to hold in position for long periods of time when applying radiation to human tissue using the device. Further, there is a need in the art for a device that improves shielding of the medical practitioner and/or other personnel from extraneous and back-scattered radiation emitted from the device or from human tissue receiving the radiation.

SUMMARY

A therapeutic applicator and method may include a wand portion and a module coupled to the wand portion. The module may have a body section and a recess positioned within the body section. The body section may include a prismatic member made of a transparent material and the body section may further include a convex surface. The convex surface may provide a magnification of a view that includes a region surrounding the recess.

A radiation source may be positioned within the recess. The body section may have a thickness greater than a diameter of the radiation source which is sufficient to attenuate radiation being emitted from the radiation source while the transparent material of the body section allows visibility of a treatment site that is adjacent to the radiation source.

The magnification of the view may fall in range between about 1.1 times to 50.0 times an unmagnified view. The module may be further contained within a metal casing. And in some embodiments, the wand portion may be contained by a metal casing. In other exemplary embodiments, the wand portion may propagate light from a light source that is adjacent to the recess.

A therapeutic applicator may include a handle and a module coupled to the handle. The module may include a body section and a recess positioned within the body section. The body section may include a prismatic member made of a transparent material. The body section may have a thickness greater than a diameter of a recess. The transparent material of the body section may allow visibility of a treatment site that is adjacent to the recess.

The body section may have a convex surface where the convex surface provides a magnification of the treatment site. In other exemplary embodiments, the applicator may further include a radiation source positioned within the recess.

This summary is provided to introduce a selection of concepts that are further described below in the detailed description and illustrated in the several detailed figures. This summary is not intended to identify key or essential features of the claimed subject matter, nor is it intended to be used as an aid in limiting the scope of the claimed subject matter.

BRIEF DESCRIPTION OF THE DRAWINGS

In the drawings, like reference numerals refer to like parts throughout the various views unless otherwise indicated. For reference numerals with letter character designations such as "102A" or "102B", the letter character designations may differentiate two like parts or elements present in the same figure. Letter character designations for reference numerals may be omitted when it is intended that a reference numeral to encompass all parts having the same reference numeral in all figures. For clarity, not all components are shown in each Figure.

FIG. 6A illustrates a cross-sectional perspective view of one exemplary embodiment of the module that includes an adhesive for the radiation source;

FIG. 6B illustrates another exemplary embodiment for the module that includes flexing fingers for capturing and holding the radiation source;

FIG. 6C illustrates another exemplary embodiment for the module that includes heat or ultrasonic swaging that may be used to affix the source into the recess of the module;

FIG. 6D illustrates another exemplary embodiment for the module that includes a thin layer of relatively radio-transparent material to hold the radiation source in place;

FIG. 8 illustrates a cross-sectional view of the source mounted flush relative to the thickness of the cylindrical body of the module (and relative to the depths shown in FIGS. 9-10) and showing schematically the radiation output field spread;

FIG. 9 illustrates a cross-sectional view of the source at an increased depth relative to the thickness of the cylindrical body of the module (and relative to the depth shown in FIG. 8) and showing schematically the radiation output field spread;

FIG. 10 illustrates a cross-sectional view of the source at an increased depth relative to the thickness of the cylindrical body of the module (and relative to the depth shown in FIG. 8) and showing schematically the radiation output field spread;

FIG. 11 illustrates an alternative exemplary embodiment where the recess within the body, radiation source orientation, and patient contacting treatment surface of the module may be disposed at an angle relative to the normal axis of the treatment site;

FIG. 12 illustrates the elongated area for the radiation isodosage or radiation field generated by the angled radiation source of FIG. 11;

FIG. 14 illustrates a perspective side view of a therapeutic applicator which is also illustrated from a different view/angle in FIG. 15;

FIG. 15 illustrates the therapeutic applicator of FIG. 14 depicting the view through the body section of the module near a treatment site which may be beneath and adjacent to the radiation source;

FIG. 19 illustrates a cross-sectional view of an exemplary embodiment of a module with a movable core element that is in a first position;

FIG. 20 illustrates a cross-sectional view of an exemplary embodiment of the module where the movable core element is in a second position relative to the first position shown in FIG. 19;

FIG. 21 illustrates a cross-sectional view of an exemplary embodiment of the module where the movable core element is in a third position relative to the first and second positions shown in FIGS. 19-20;

FIG. 25A illustrates a side view of an alternative exemplary embodiment for the module illustrated in FIGS. 19-24 where the module comprises a threaded core element;

FIG. 25B illustrates a side view of the threaded core element in a slightly elevated position relative to the position shown in FIG. 25A;

FIG. 25C illustrates a side view of the threaded core element in a slightly elevated position relative to the position shown in FIG. 25B;

FIG. 26A illustrates an exemplary embodiment of a movable core of a module with a mating cap for a module;

FIG. 26B illustrates an exemplary embodiment of a movable core of a module engaging a mating cap after the core has been moved to an elevated position relative to the position shown in FIG. 26A;

FIG. 26C illustrates an exemplary embodiment of a movable core of a module engaging a mating cap after the core has been moved to an elevated position relative to the positions shown in FIG. 26A and FIG. 26B;

FIG. 26D illustrates a side, perspective view of a cap alone and without being in contact with a core or module;

FIG. 27A illustrates a side perspective view of a module which contains or holds a disk-shaped radiation source;

FIG. 27B illustrates a side perspective view of a module which contains or holds a rectangular radiation source;

FIG. 27C illustrates a side perspective view of a module which contains or holds an obround radiation source;

FIG. 27D illustrates a side perspective view of a module which contains or holds a plurality of small, prismatic radiation sources;

FIG. 27E illustrates a side perspective view of a module which contains or holds a plurality of small, prismatic radiation sources or seeds positioned within a material or a sub-container which is within recess of the module body;

FIG. 27F illustrates a cross-sectional view of the module 105 of FIG. 27E;

FIG. 28A illustrates an elevational perspective view of a therapeutic applicator according to another exemplary embodiment having a module with at least three functions and a wand portion which does not have any tapered portion;

FIG. 28B illustrates a side cross-sectional view of the module illustrated in FIG. 28A;

FIG. 28C illustrates a bottom view of the module illustrated in FIGS. 28A-28B.

FIG. 29A illustrates a perspective view of a module that is encased within a metallic outer jacket;

FIG. 29B illustrates a cross-sectional view of the exemplary embodiment of the module illustrated in FIG. 29A;

FIG. 30A illustrates a perspective view of a module that is encased within a metallic outer jacket and having a convex surface;

FIG. 30B illustrates a cross-sectional view of the exemplary embodiment of the module illustrated in FIG. 30A;

FIG. 31A illustrates a cross-sectional view of an exemplary embodiment of a therapeutic applicator, similar to the exemplary embodiment of FIGS. 29A-29B, but with a light source and a light guide to produce light rays;

FIG. 31B illustrates a cross-sectional view of an exemplary embodiment of a therapeutic applicator similar to the exemplary embodiment of FIGS. 30A-30B, but with a light source and a light guide to produce light rays;

FIG. 31C is a cross-sectional view of an exemplary embodiment of a therapeutic applicator which has a hollow module filled with a transparent liquid;

FIG. 31D is a cross-sectional view of an exemplary embodiment of a therapeutic applicator which has a hollow module filled with a transparent liquid and having a convex surface for magnifying tissue adjacent to the radioactive source;

FIG. 31E illustrates a cross-sectional view of an exemplary embodiment of a therapeutic applicator which has a hollow module filled with a transparent liquid and with a metal casing;

FIG. 31F illustrates a cross-sectional view of an exemplary embodiment of a therapeutic applicator which has a hollow module filled with a transparent liquid and having a metal casing along with a convex or curved surface for magnifying tissue adjacent to the radioactive source;

FIG. 31G illustrates a cross-sectional view of an exemplary embodiment of a therapeutic applicator which has a hollow module filled with a transparent liquid and having both a metal casing and an optical waveguide 3102 with light source;

FIG. 31H illustrates a cross-sectional view of an exemplary embodiment of a therapeutic applicator which has a hollow module filled with a transparent liquid and having both a metal casing and an optical waveguide 3102 with light source in addition to a convex/curved surface;

FIG. 32A illustrates an exemplary therapeutic applicator having a convex surface that produces magnification, but the device does not have a wand portion or arm portion which were described above in connection with FIGS. 29A-31B; and FIG. 32B illustrates an exemplary therapeutic applicator having a convex surface that produces magnification along with a light waveguide, but the device does not have a wand portion or arm portion similar to FIG. 32A.

DETAILED DESCRIPTION OF THE EXEMPLARY EMBODIMENTS

The word "exemplary" is used herein to mean "serving as an example, instance, or illustration." Any aspect described herein as "exemplary" is not necessarily to be construed as exclusive, preferred or advantageous over other aspects.

Figure 1:
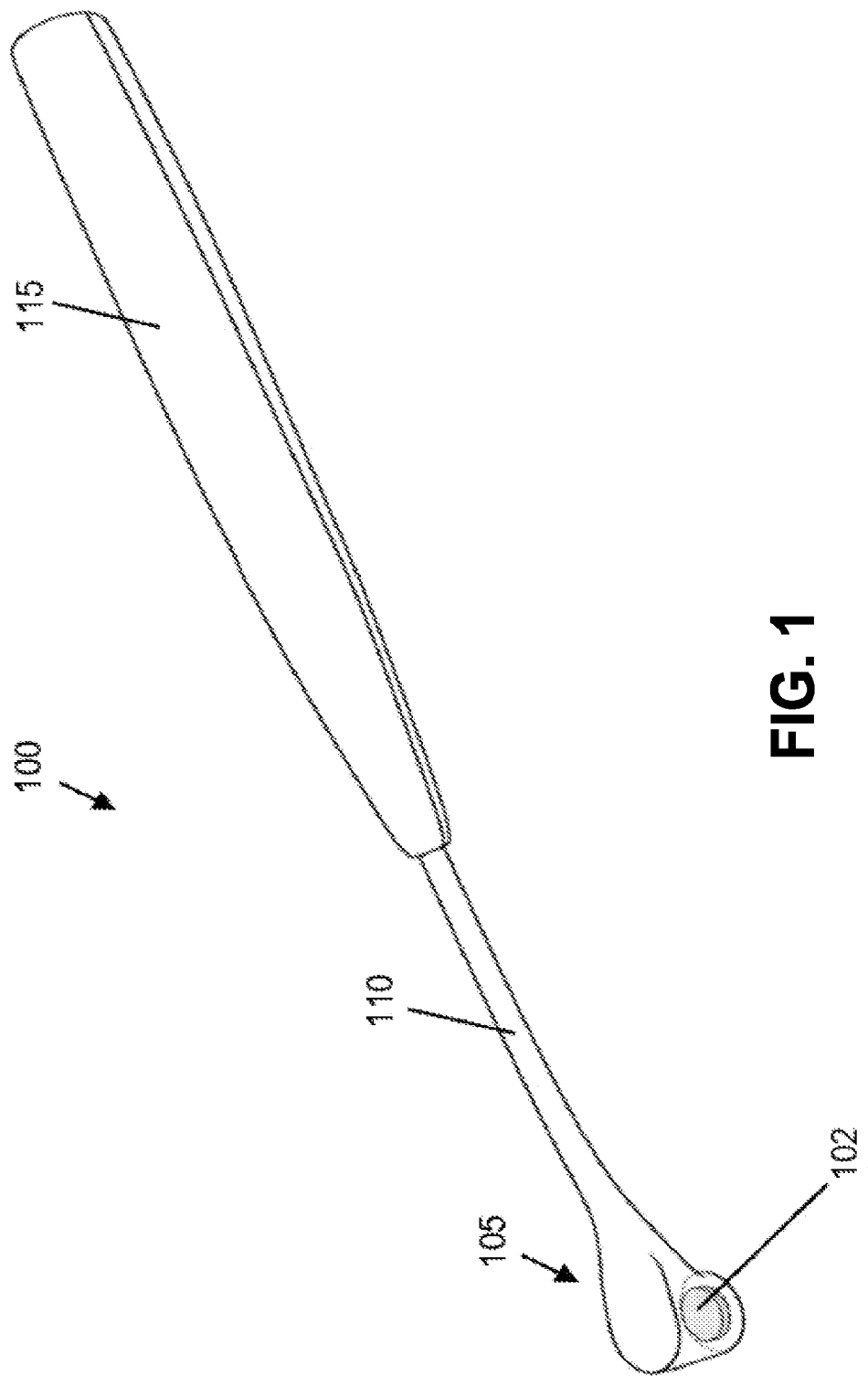
FIG. 1 this figure illustrates an elevational perspective view of a therapeutic applicator having a module with at least three functions.
Figure 2:
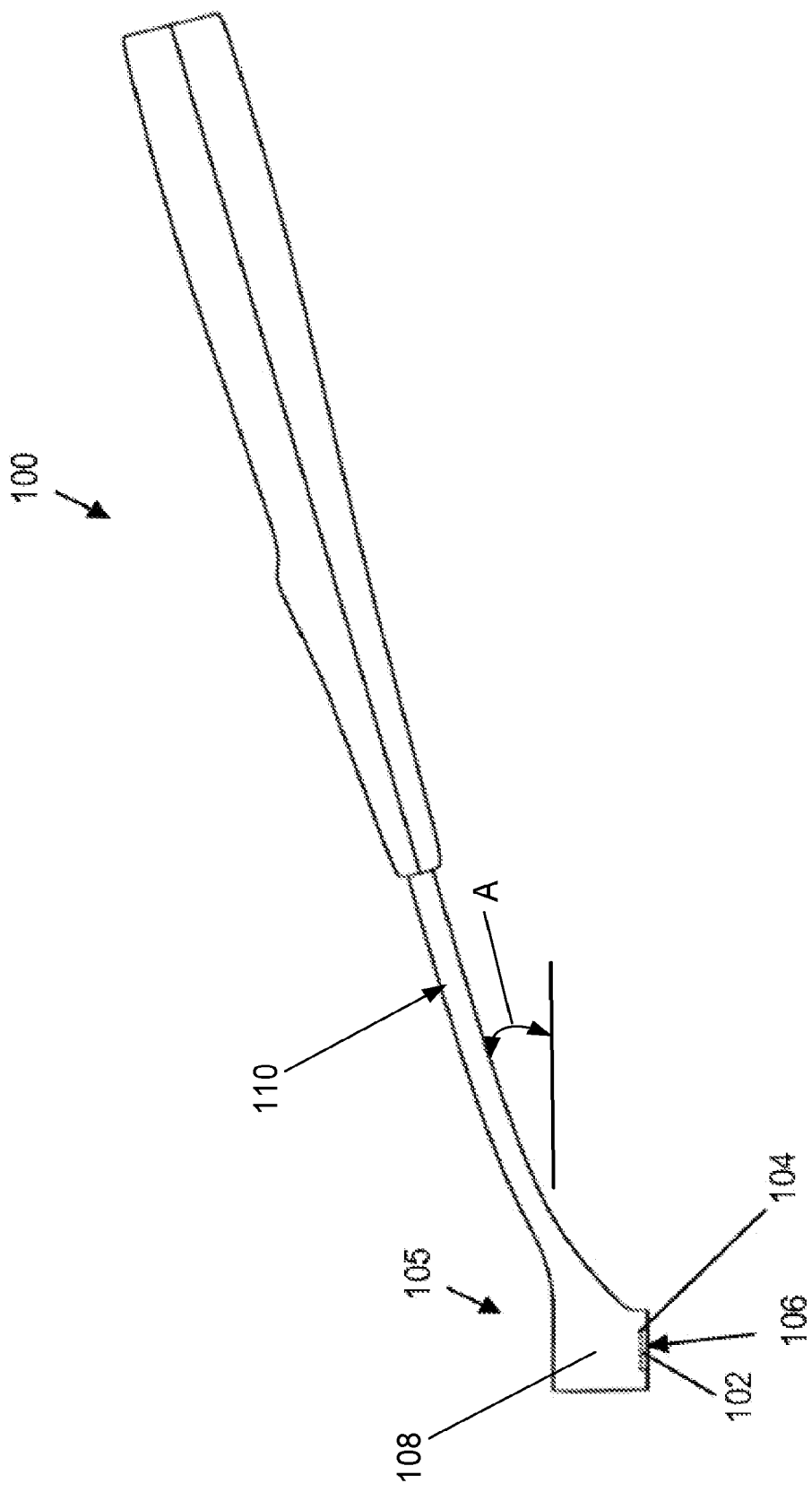
FIG. 2 illustrates a side view of the therapeutic applicator presented in FIG. 1.
Figure 3:
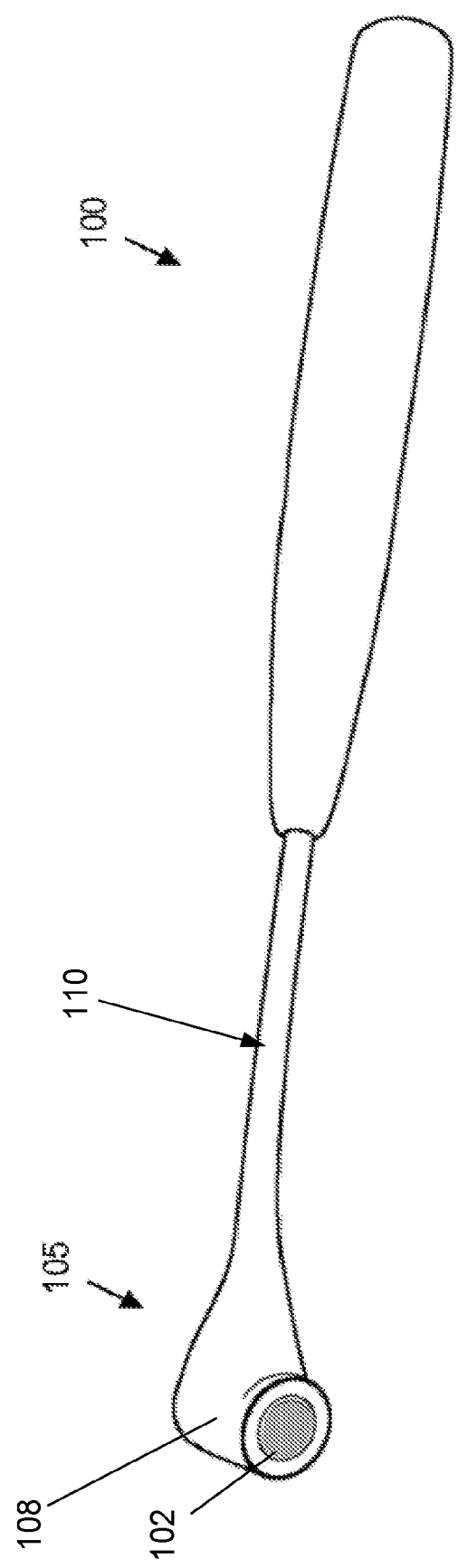
FIG. 3 illustrates another low angle perspective view of the therapeutic applicator presented in FIG. 1.
Figure 4A:
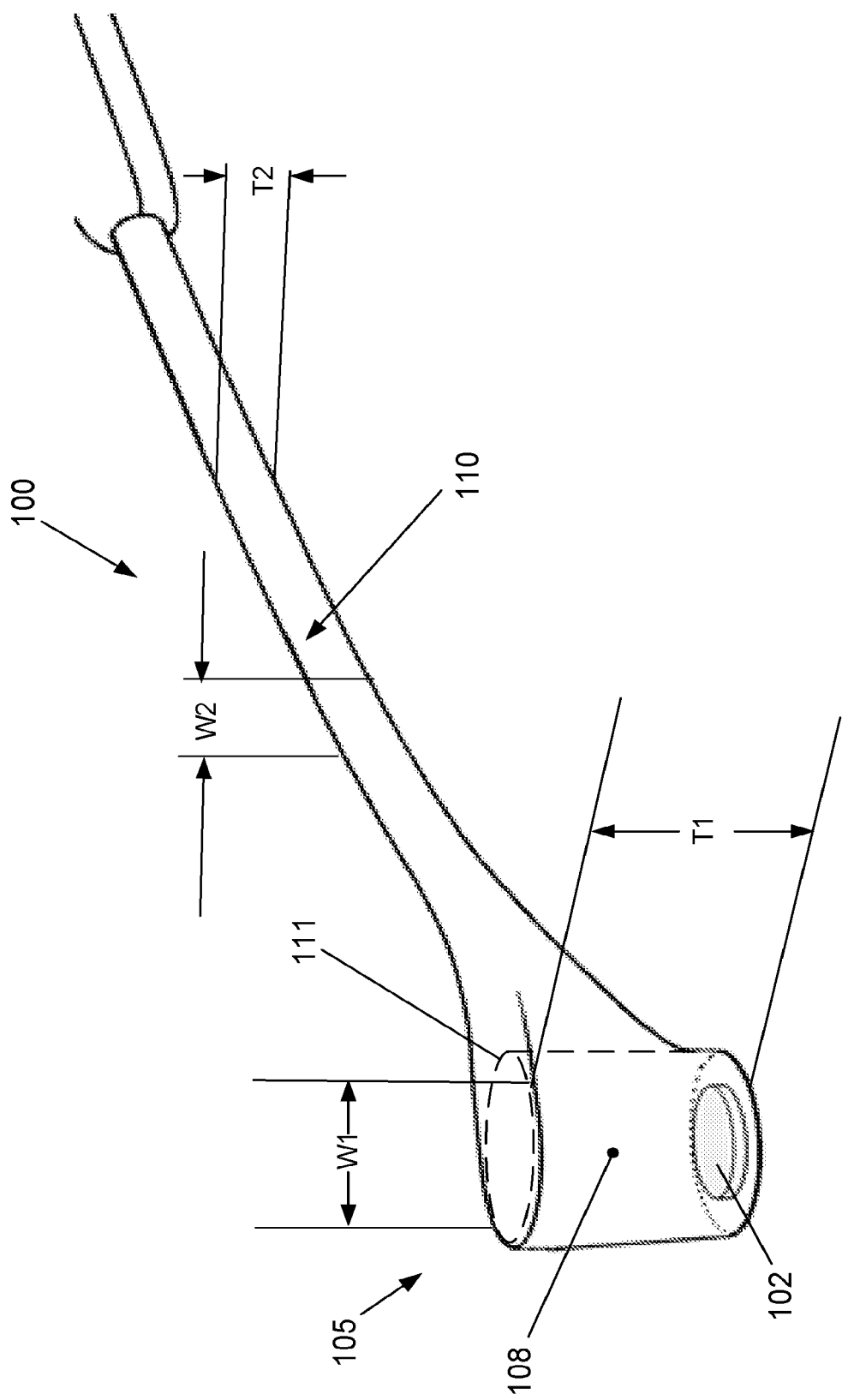
FIG. 4A illustrates a close-up perspective side view of the body section of the module shown in FIGS. 1-3.
Figure 4B:
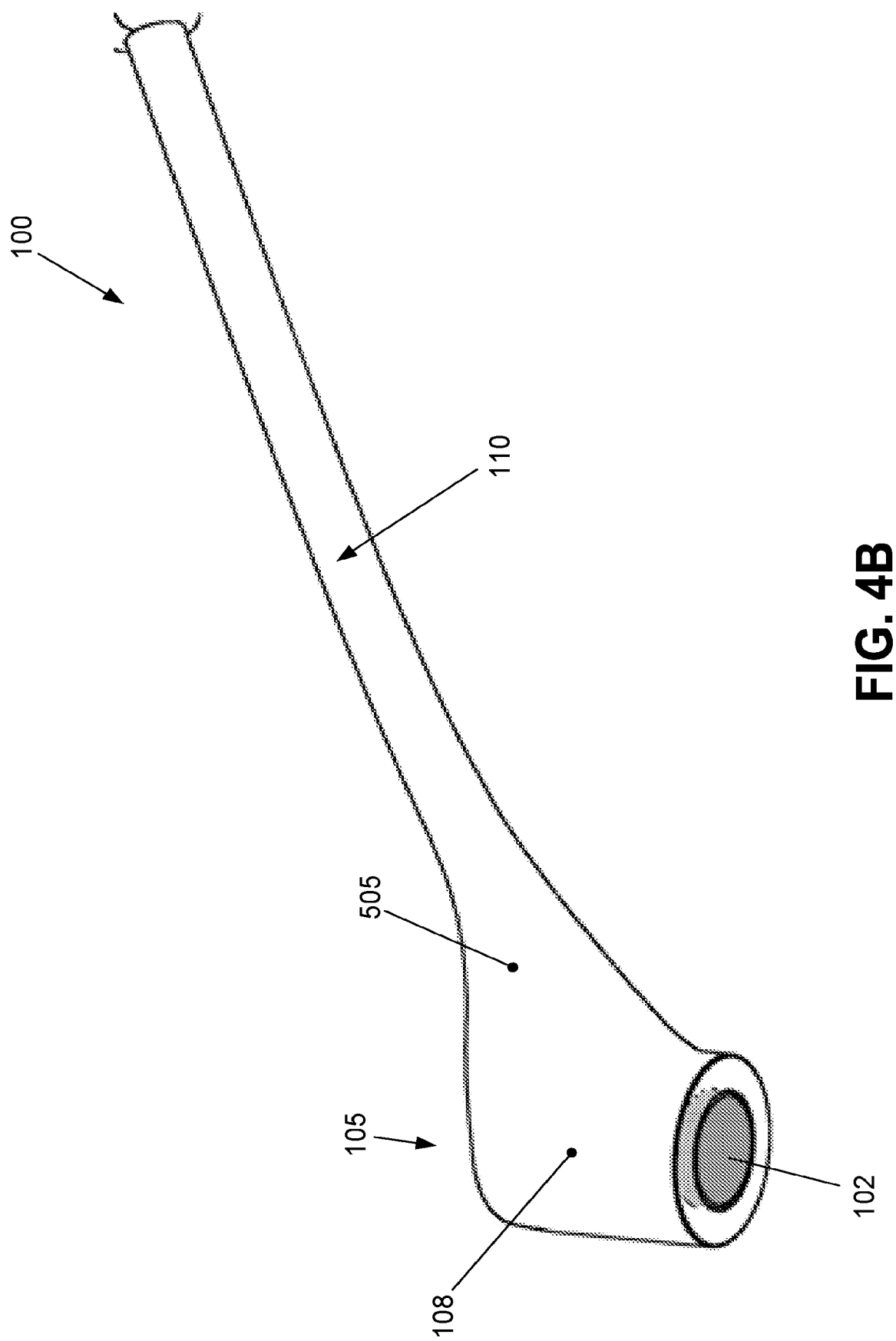
FIG. 4B illustrates a close-up perspective low angle view of the body section of the module shown in FIGS. 1-4A.

One preferred and exemplary embodiment can be seen in FIGS. 1-3 with close-up views of the device's module area 105 and, according to the preferred embodiment, an integral applicator 100 as shown in FIGS. 4a and 4b.

Referring now to FIG. 1, this figure illustrates an elevational perspective view of a therapeutic applicator 100 having a module 105 with at least three functions: a holding mechanism for a radiation source 102; a shield for radiation emitted by the radiation source 102; and a mechanism for increasing visibility of the treatment site. More specifically, the therapeutic applicator 100 may be designed to selectively emit and shield beta radiation. The applicator 100 may comprise three principal portions: a distal tip area comprising the module 105; a wand 110 that is attached either integrally or removably to the module 105; and a handle 115 that be held by a hand of a medical practitioner, where the handle 115 is coupled to the wand 110. Each of these component portions will be described with reference to the Figures.

Exemplary materials for the radiation source 102 may include, but are not limited to $^9$Sr, $^{169}$Yb, $^{90}$Y, $^{192}$Ir, $^{103}$Pd, $^{177}$Lu, $^{149}$Pm, $^{140}$La, $^{153}$Sm, $^{186}$Re, $^{188}$Re, $^{166}$Ho. $^{166}$Dy, $^{137}$Cs, $^{57}$Co, $^{169}$Er, $^{165}$Dy, $^{97}$Ru, $^{193m}$Pt, $^{195m}$Pt, $^{105}$Rh, $^{68}$Ni, $^{67}$C, $^{64}$Cu, $^{109}$Cd, $^{111}$Ag, $^{198}$Au, $^{199}$Au, $^{201}$Tl, $^{175}$Yb, $^{47}$Sc, $^{159}$Gd, and $^{212}$Bi, just to name a few. The radiation source 102 may include any combination of these materials as understood by one of ordinary skill in the art.

Meanwhile, the module 105 may comprise a polymeric material that possesses at least two properties of being both radiation tolerant and biologically safe for use in contact with any human tissue being treated with radiation source 102. The material of the module 105 usually must also exhibit adequate toughness/strength to prevent breakage during use. This material advantageously is transparent affording the medical practitioner increased visibility of the treatment site through the body of the module 105. Materials suitable for the module 105 include, but are not limited to, co-polyesters, and in some use cases where long-term beta exposure is not required, polyethylene terephthalate, polycarbonate; polysulfone, and metal-containing plastics which are transparent to light such as, but not limited to, a leaded polymethyl methacrylate (PMMA—acrylic polymer), glass, or any combination thereof of these materials.

While human tissue is one intended environment or use for the applicator 100, other uses for the applicator 100 are possible. That is, the applicator 100 may be used on animal tissue in a veterinary context as understood by one of ordinary skill in the art.

Referring now to FIG. 2, this figure illustrates a side view of the therapeutic applicator 100 presented in FIG. 1. FIG. 2 further illustrates a treatment or patient contacting surface 106 of the applicator 100. The module 105 may be configured to have a recess 104 for holding the radiation source 102. Meanwhile, a body section 108 of the module 105 may be configured to provide adequate radiation attenuation, and thus protective shielding, for surfaces not contacting the treatment site. The wand portion or handle 110 may be positioned at an angle A relative to a top surface of the module 105. As illustrated inf FIG. 2, angle A is usually less than 90.0 degrees, and generally, angle A is equal to or less than 45.0 degrees. Other magnitudes for angle A are possible and are included within the scope of this disclosure.

Referring now to FIG. 3, this figure illustrates another perspective view of the therapeutic applicator 100 presented in FIG. 1. The source 102 may be attached to the module 105 as shown and is positioned within the recess 104 (See FIG. 2).

Referring now to FIG. 4A, illustrates a close-up perspective side view of the body section of the module shown in FIGS. 1-3. The body section 108 of FIG. 4 is further shown with dashed lines 111 that provide an outline of a substantially cylindrical shape. Meanwhile, the radiation source 102 is shown to have a substantially circular shape. The source 102 may be characterized has having a disc shape since the source 102 has some depth/thickness relative to its substantially circular shape. Other shapes for the body section 108 and radiation source 102 are possible and are included within the scope of this disclosure.

As noted above, the module 105 may comprise a cylindrical body section 108. However, the module 105 may comprise other geometrical shapes besides a cylinder. For example, the module 105 may comprise a body section 108 having a cross-sectional shape such as, but not limited to, a square, a rectangle, a pentagon, a hexagon, an octagon, etc. Generally, the body section 108 may comprise a prismatic member. A prismatic member is defined in this disclosure as a geometrical structure having a straight center-line and symmetrical cross-sectional shape.

In the exemplary embodiment shown in FIG. 4A, the substantially cylindrical shape 111 of the body section 108 may have a width dimension W1 and a thickness dimension T1. Meanwhile, the wand portion or handle 110 coupled to the body section 108 may also have a width dimension W2 and a thickness dimension T2. The width dimension W1 of the body section 108 of the module 105 is generally greater than the width dimension W2 of the wand portion 110.

Similarly, the thickness dimension T1 (about 11.0 mm) of the body section 108 is generally greater than the thickness dimension T2 (about 3.2 mm) of the wand portion 110. If the wand portion 110 is substantially cylindrical, then the width dimension W2 (about 3.2 mm) and the thickness dimension T2 (about 3.2 mm) of FIG. 4A would be generally the same and would comprise a single diameter dimension, as understood by one of ordinary skill in the art. If a differently sized radiation source and/or a different radiation source were used, the dimensions of the module would likely change but the dimensions of the wand portion will usually remain the same as presented in the several figures of this disclosure.

The wand portion 110 may also comprise a prismatic member, similar to the body section 108. However, the wand portion 110 is usually smaller in both thickness and width compared to the body section 108.

As noted previously, with the module 105 sized in a manner unrelated to that of the wand portion 110, the module 105 may provide at least two functions beyond holding the radiation source 102: (1) the module 105 may provide shielding from radiation being emitted by the source 102; and (2) the module 105 may increase the visibility for the medical practitioner of the treatment site, which is generally adjacent to the source 102 and opposite to the module 105.

Referring now to FIG. 4B, this figure illustrates a close-up perspective bottom view of the body section of the module shown in FIGS. 1-4A. In this figure, a tapered portion 505 present between the body section 108 and wand portion 110 is more visible. The tapered portion 505 transitions the relatively uniform cross-section of the wand portion 110 to the larger body section 108 which has larger dimensions for the visibility function and shielding function described above.

Figure 5A:
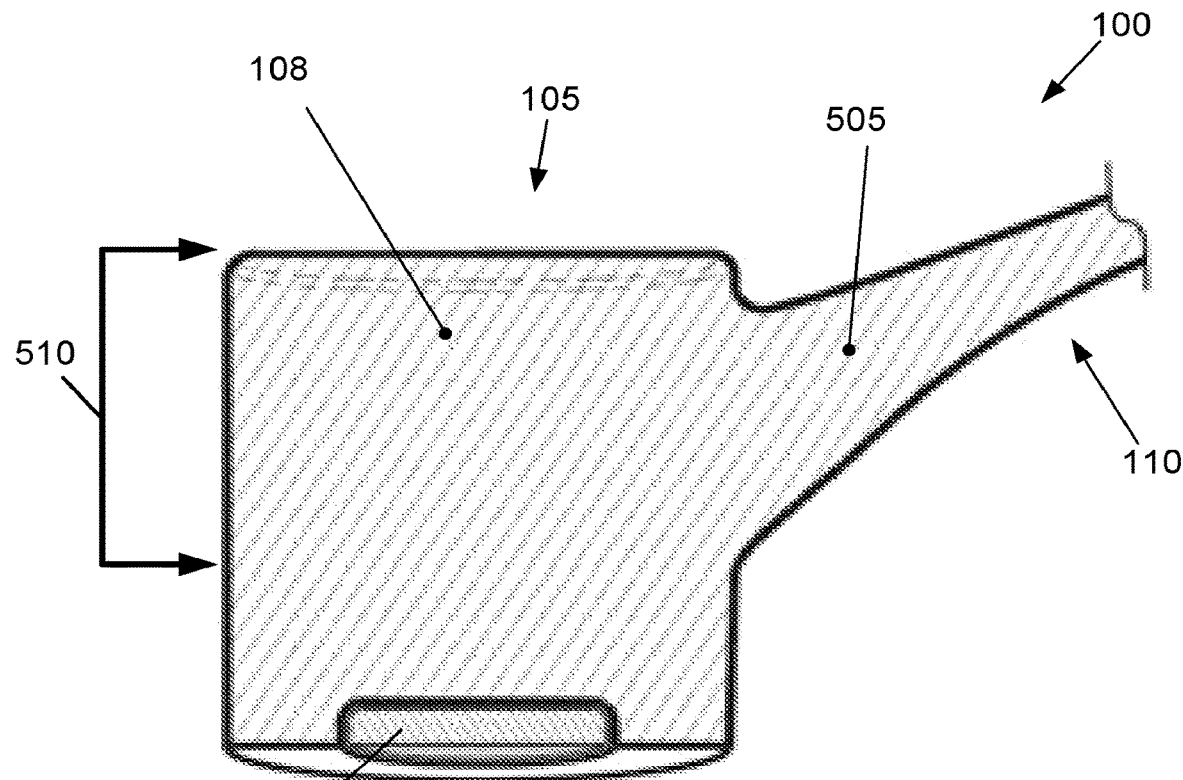
FIG. 5A illustrates a side close-up view of the cylindrical body section of the module as well as the tapered portion of the wand element.

Referring now to FIG. 5A, this figure illustrates a side close-up view of the cylindrical body section 108 of the module 105 as well as the tapered portion 505 of the wand portion 110. The tapered portion 505 generally is positioned in an upper portion or upper section 510 of the cylindrical body section 108 as shown in FIG. 5A. Generally, the tapered portion 505 couples to the cylindrical body section 108 of the module 105 at portions/regions that are above the half-way or 50% of the thickness T1 dimension (see FIG. 4A for the T1 dimension) of the cylindrical body section 108.

Figure 5B:
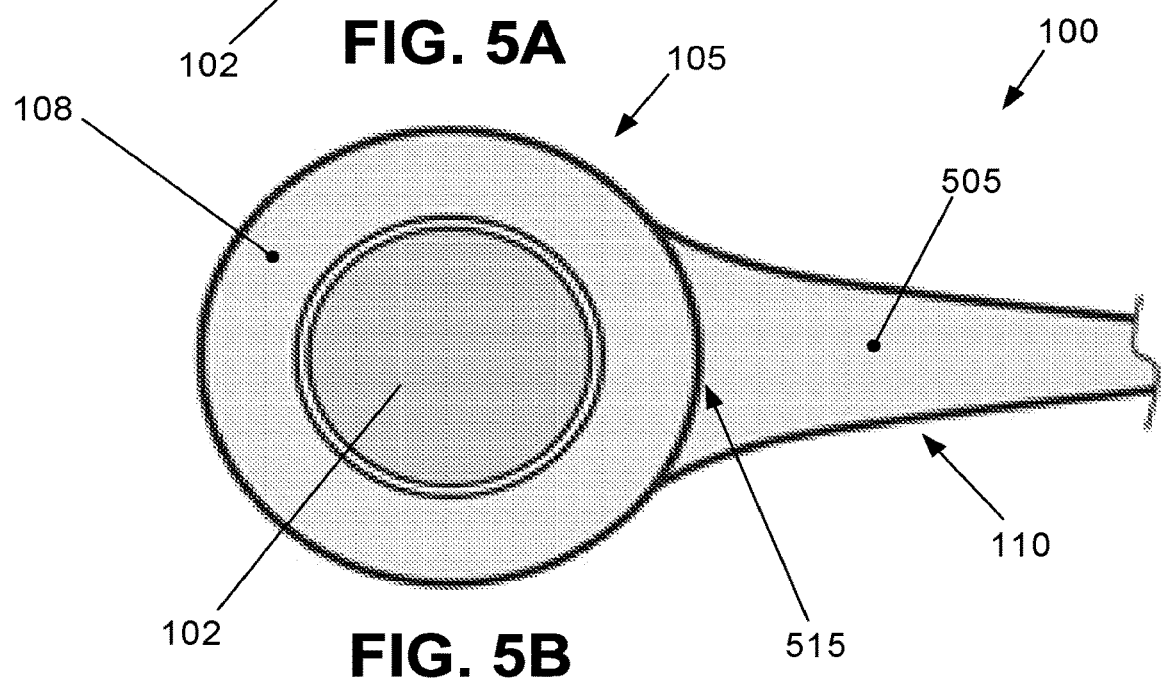
FIG. 5B illustrates a bottom view of the cylindrical body section of the module as well as the tapered portion of the wand element.

Referring now to FIG. 5B, this figure illustrates a bottom view of the cylindrical body section 108 of the module 105 as well as the tapered portion 505 of the wand portion 110. In this view and according to this exemplary embodiment of the applicator 100, the tapered portion 505 couples to the cylindrical body section 108 along a region 515 that is substantially less than the entire circumference of the cylindrical body section 108. The coupling region 515 generally comprises a magnitude which is less than one-half the entire circumference of the cylindrical body section 108 of the module 108.

Referring now to FIG. 6A, this figure illustrates a cross-sectional perspective view of one exemplary embodiment of the module 105 that includes an adhesive 602 for the radiation source 102. Specifically, in this exemplary embodiment, the source 102 is mounted in and coupled to the recess 104 of the module 105 using a suitable adhesive 602. Exemplary adhesives include, but are not limited to, medical-grade epoxies tested for radiation tolerance, or for short exposure duration, medical-grade cyanoacrylate adhesives.

Referring now to FIG. 6B, this figure illustrates another exemplary embodiment for the module 105' that includes flexing fingers 606 for holding the radiation source 102. Specifically, the module 105' of FIG. 6B may comprise mechanical means, such as, but not limited to, flexing fingers 106 for holding the source 102 within the recess 104. With the flexing fingers 106, no adhesives are needed in this exemplary embodiment to secure the source 102 within the module 105.

Referring now to FIG. 6C, this figure illustrates another exemplary embodiment for the module 105" that includes ultrasonic swaging 609 that may be used to affix the source 102 into the recess 104 of the module 105". In such a swaging process, an ultrasonic horn in the form of a ring or an uninterrupted ring, having a diameter slightly greater than that of the recess 104, would be pressed into the face of the module 105" concentric with the source recess 104. This would deform a ridge of the polymer concentrically inward to create a capturing edge for maintaining the source 102 in the recess 104. FIG. 6C also illustrates some exemplary dimensions for the module 105". These dimensions are based on the specific radionuclide output as selected for insertion into the module 105" as well as the density or attenuation characteristics, Z, of the selected polymer which forms the cylindrical body section 108.

In the exemplary embodiment illustrated in FIG. 6C, a co-polyester module 105" may contain a titanium encapsulated $^{90}Y$ 3 mm (R1)×1 mm thick (Th1) source 102, where exemplary dimensions may include, but are not limited to: R1=3 mm, R2=5 mm, T1=11.25 mm, and Th1=1 mm. The inventors recognize that there is an inherent compromise between a size which affords adequate shielding and a size (particularly the R2 dimension) which has dimensions suited to the patient treatment site, (in this case, between the eyelids, after some deformation by surgical accessories). The magnification of the view through module 105 is, generally, based on the convexity of the top surface of the module 105. The exact optical magnification is usually based on the refractive index of the selected polymer, and the magnification desired by the medical practitioner.

In the exemplary embodiment of FIG. 6C, the radiation source 102 may have an exemplary thickness Th1 that ranges between about 0.5 mm to about 2.0 mm. In addition, the radiation source 102 may have a radius R1 that ranges between about 2.0 mm to about 7.0 mm. However, other dimensions, larger or smaller, are possible and are included within the scope of this disclosure.

R2 which is the radius of the cylindrical body section 108 of the module 105" (which is ½ of the W1 dimension shown in FIG. 4A) may be generally, double the size of the R1 dimension. For example, if R1 is 2.0 mm, then R2 is usually about 4.0 mm. Further, the thickness dimension T1 is generally greater than a diameter (R1×2=D) of the disc shaped radiation source 102 and the recess 104 which closely mirrors the shape of the radiation source 102.

Referring now to FIG. 6D, this figure illustrates another exemplary embodiment for the module 105''' that includes a thin layer of relatively radio-transparent material 112 to hold the radiation source 102 in place. Specifically, the radio-transparent material 112 may include, but is not limited to, a biocompatible radiation-resistant polymer. For example, the material may comprise a co-polyester which may be overlaid and adhered to capture the radiation source 102 in the recess 104. The thickness Th2 of the material 112 illustrated in FIG. 6D may have a magnitude of about 0.10 mm. However, other thicknesses greater or less than this value are possible as understood by one of ordinary skill in the art.

As illustrated in FIGS. 6C-6D, the cylindrical body section 108 of the module 105 has a thickness dimension T1. The thickness dimension T1 is sized such that it attenuates significant portions of the source's radiation output so as to achieve acceptable safety levels for the practitioner and other personnel present during treatment. The thickness dimension T1 will be discussed in additional detail below in connection with FIG. 16A.

Figure 6G:
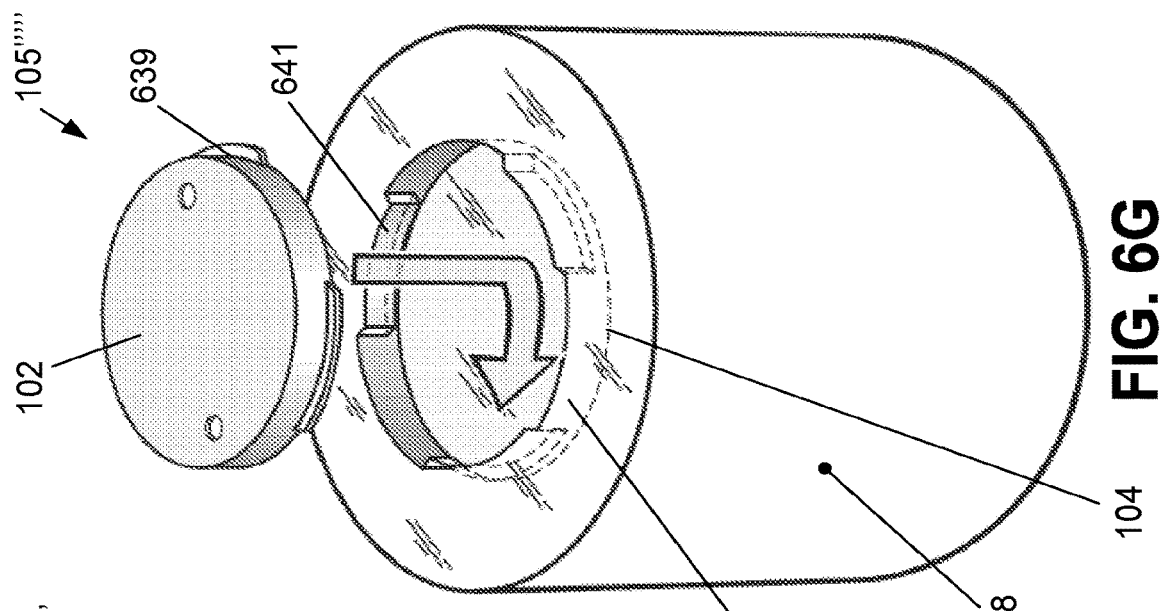
FIG. 6G illustrates a side perspective view of the bayonet configuration of the module illustrated in FIG. 6F.
Figure 6F:
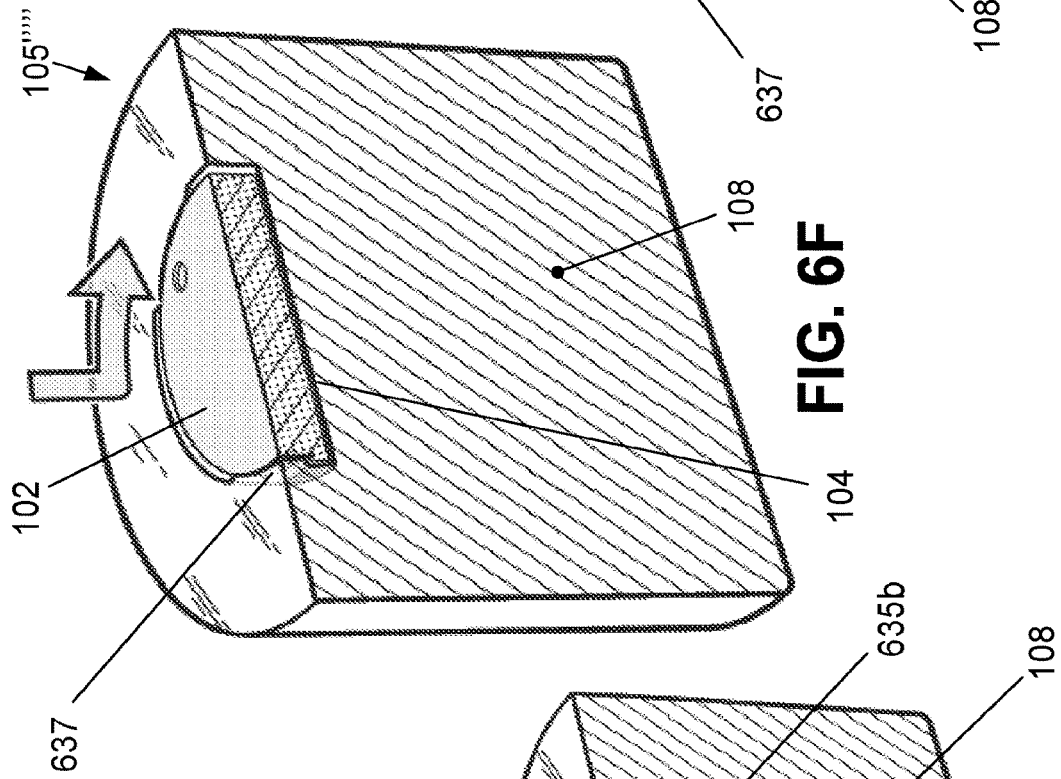
FIG. 6F illustrates another exemplary embodiment for the module that may be characterized as a bayonet configuration to hold the radiation source in place.
Figure 6E:
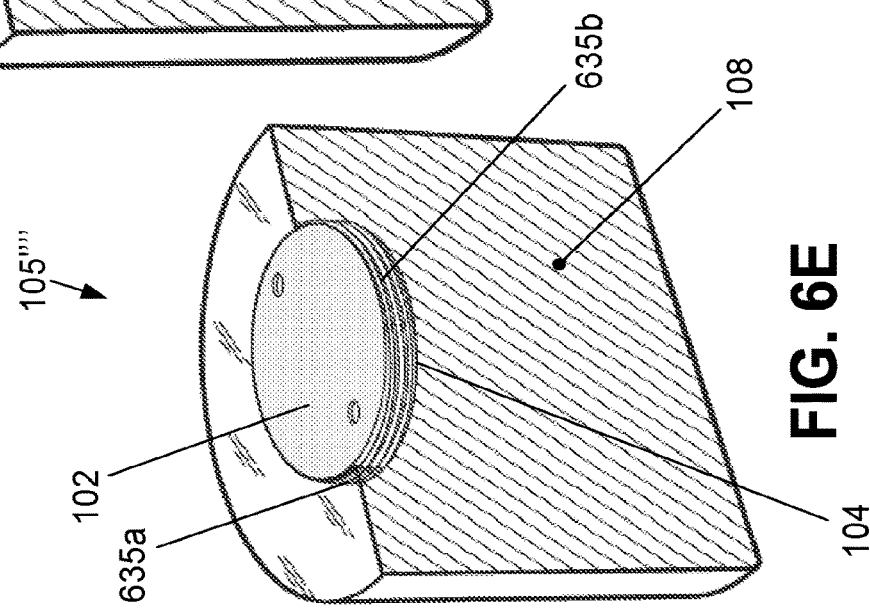
FIG. 6E illustrates another exemplary embodiment for the module that includes screw threads to hold the radiation source in place.

Referring now to FIG. 6E, this figure illustrates another exemplary embodiment for the module 105"" that includes screw threads 635a, 635b to hold the radiation source 102 in place. Specifically, the module body 108 and its recess 104 may have first threads 635a which receive second threads 635b. The second threads 635b may be put on the outside of the radiation source 102. Thus, the radiation source 102 may be "screwed" into recess 104 according to this exemplary embodiment depicting one mounting option for the source 102.

Referring now to FIG. 6F, this figure illustrates another exemplary embodiment for the module 105" that may be characterized as a bayonet configuration to hold the radiation source 102 in place. FIG. 6F is a cross-sectional view that shows how the recess 104 may have one or more mechanical projections 641 (see FIG. 6G) present on the side wall 637 of the recess 104. The mechanical projections 641 of the side wall 637 may engage mechanical projections 639 (see FIG. 6G.) on the source 639 when the source is rotated to "lock" into the recess 104.

Referring now to FIG. 6G, this figure illustrates a side, perspective view of the bayonet configuration of the module 105"" illustrated in FIG. 6F. In this view, the radiation source 102 having projections 641 is shown disconnected and in an "unlocked" state relative to the embodiment shown in FIG. 6F. In FIG. 6F, the "unlocked" source 102 is shown above the body 108 of the module 105". As noted previously, the mechanical projections 639 of the source 102 are designed to interact and lock with the mechanical projections 641 of the side wall 637 of the recess 104.

The number and sizes of the projections 639, 641 may vary without departing from the scope of this disclosure as understood by one of ordinary skill in the art. For example, a fewer or a greater number of projections 639 may be employed compared to those shown in FIGS. 6F-6G.

Further, as will be explained below, the radiation source 102 may comprise a plurality of seeds or separate elements which may be contained in a sub-container 2702 (see FIGS. 27E-27F described below). The sub-container 2702 of FIGS. 27E-27F may take on or encompass any one of the mechanical mounting configurations illustrated in FIGS. 6A-6G as understood by one of ordinary skill in the art.

Figure 7A:
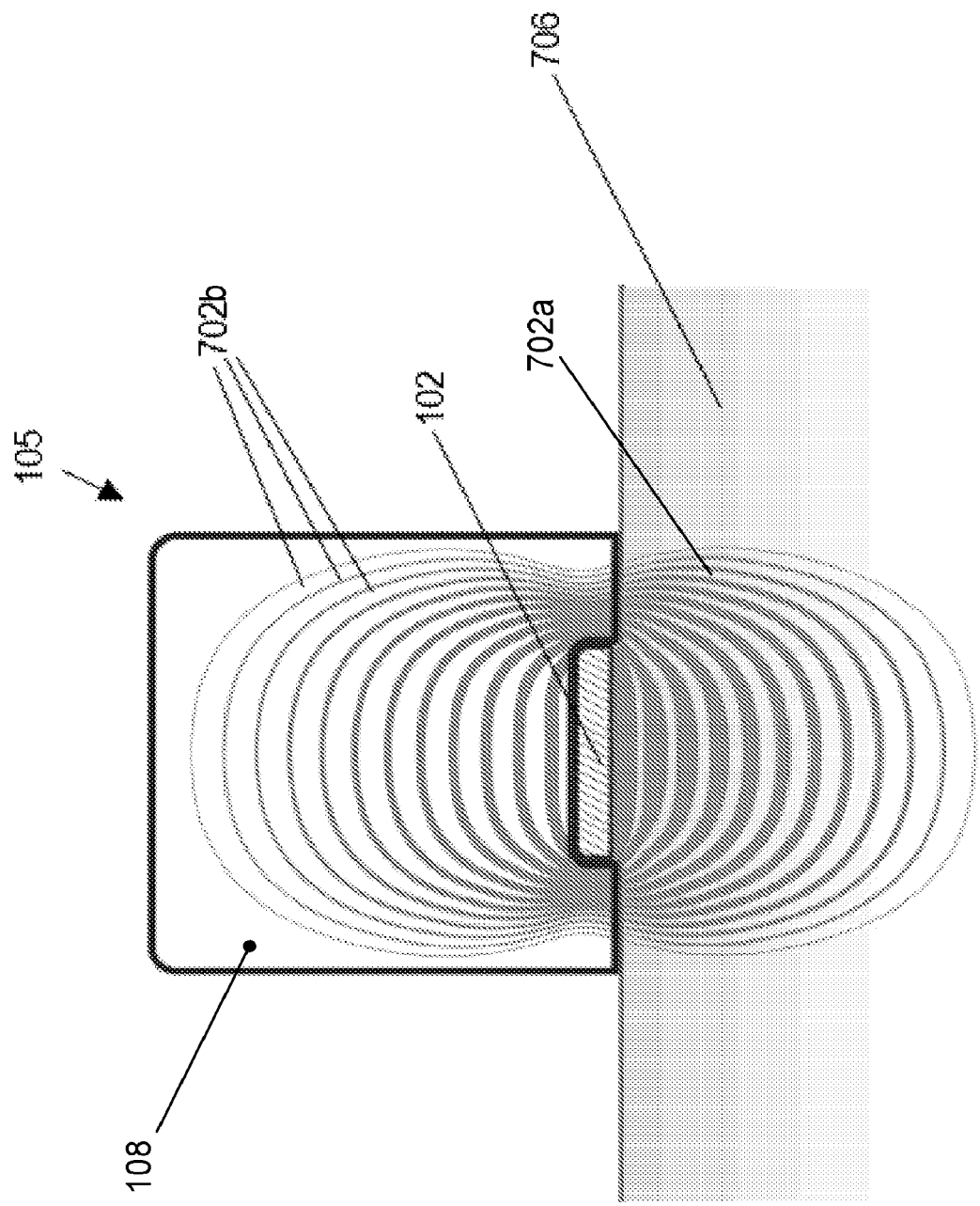
FIG. 7A illustrates a schematic example of isodose profiles typical of the attenuation of beta rays from the source in both the module body and patient tissue.

Referring now to FIG. 7A, this figure illustrates a schematic example of isodose profiles typical of the attenuation of beta rays 702 from the source 102 in both the module body section 108 and patient tissue 706 resulting in radiation only affecting the patient while protecting the medical practitioner from unwanted radiation exposure. Note that the radiation emissions from the source 102 are anisotropic, which means that a specific volumetric profile for the module 105 usually must be configured to correspond to the varied multi-axial output levels characteristic of the selected radiation source 102.

Figures 7B, 7C:
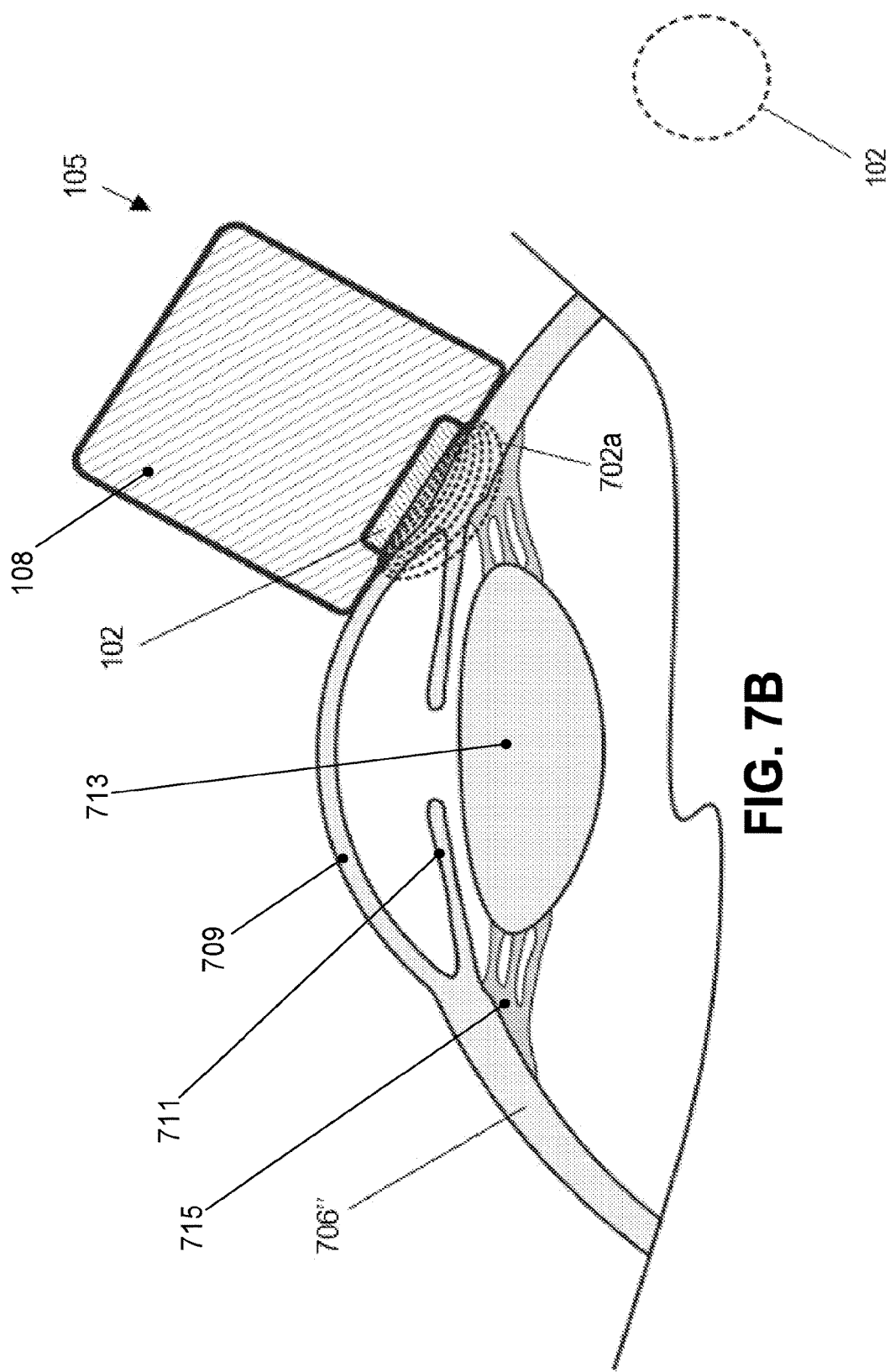
FIG. 7B shows a cross-sectional view of a module, depicted here devoid of the wand component, placed upon the eye tissue for treatment of a malignant or benign growth.
FIG. 7C illustrates the resulting treatment area that is generally circular corresponding to the use of a circular source.

Referring now to FIG. 7B, this figure shows a cross-sectional view of module 105, (depicted here devoid of the wand component 110) placed upon the eye tissue 706" for treatment of a malignant or benign growth. Schematic radiation isodose contours are indicated by the dashed lines 702 beneath the face of the source 102 overlaid on a cross-section of the human eye 706". Seen here in this cross-sectional view are the sclera 706", the cornea 709, the iris 711, the lens 713, and the ciliary muscles 715.

Referring now to FIG. 7C, this figure illustrates the resulting treatment area that is generally circular corresponding to the use of a circular source 702, such as shown in FIGS. 7A-7B. If non-circular sources 102 (not illustrated) were mounted within the module 105, it would result in differently shaped treatment areas corresponding to the shape and attitude of the source 102 used. Since the polymer module 105 attenuates beta radiation emissions 702 from the source 102 (See FIG. 7A), it may be advantageous in certain treatment applications to dimension the module to additionally limit the lateral spread of radiation.

Thus, in certain exemplary embodiments, the mounting of the source 102 in the module 105 may be recessed so as to surround the side areas of the radiation field 702 with polymer to limit the spread of radiation 702 to a more central area. Referring now to FIG. 8, this figure illustrates a cross-sectional view of the source 102 at a very shallow depth relative to the thickness of the cylindrical body section 108 of the module 105 (and relative to the depths shown in FIGS. 9-10). The recess 104 may have a rounded edge. The arrows shown in FIG. 8 (and FIGS. 9-10) indicate schematically the relative field shapes 702 arising from the use of differing recess depths and wall angle of the recess 104. These diagrams illustrated in FIGS. 8-10 represent only a few of many similar recessed configurations having varied depths and geometries for the recess 104.

Referring now to FIG. 9, this figure illustrates a cross-sectional view of the source 102 at an increased depth relative to the thickness of the cylindrical body section 108 of the module 105 (and relative to the depth shown in FIG. 8). The increased depth of the recess 104 of FIG. 9 and the upright wall 902 focus the radiation field 702 into a tighter area/regions compared to the radiation fields 702 of FIGS. 8 and 10.

Referring now to FIG. 10, this figure illustrates a cross-sectional view of the radiation source 102 at an increased depth relative to the thickness of the cylindrical body section 108 of the module 105 (and relative to the depth shown in FIG. 8). Specifically, FIG. 10 illustrates a chamfered edge or conical wall or flared wall 1002, which may be part of the recess 104. Compared to the radiation fields 702 of FIGS. 8 & 9, the radiation field 702 of FIG. 10 is wider than the field 702 of FIG. 9, but not as wide as the field 702 of FIG. 8.

Referring now to FIG. 11, this figure illustrates an alternative exemplary embodiment where the recess 104, radiation source orientation, and patient contacting treatment surface 1102 of the module 105 may be disposed at an angle relative to the normal axis N of the treatment site. The module 105 may comprise an additional body section 1108 that extends past the radiation source 102. Since beta radiation is minimally attenuated in air, the possibility exists that by tilting the source 102 at an angle to the treatment surface 1102, the resulting isodosage or radiation field 702 can be distributed over an elongated area 702a (See FIG. 12) even if the radiation source 102 itself is circular.

Referring now to FIG. 12, this figure illustrates the elongated area 702a for the radiation isodosage or radiation field 702 generated by the angled radiation source 702 of FIG. 11. The isodosage 702 of radiation hitting the elongated area 702a may be useful in treating an area of human tissue requiring anti-scarification treatment following a surgery for pterygium, for example, where an elongated area needs treatment. Additional thickness of the volumetric shape of the module 105 beyond that strictly necessary for acceptable shielding levels may be present to augment its function in two primary ways: First, the additional thickness of the module 105 may be provided to further enhance shielding in the direction of the medical practitioner's hand when in use, such that the attenuation of the beta radiation goes beyond acceptable levels for even more reduction in radiation exposure by the medical practitioner.

It should be noted that for placement and maneuverability in reaching the treatment position, it is advantageous to minimize the dimensions of the module 105 in and near the patient contacting surface 1102 to the extent possible given the ever-present requirement for the safety of attending personnel, yet in other portions of the module 105, excess thickness may be added to deliberately exceed acceptable levels of shielding.

Figure 13:
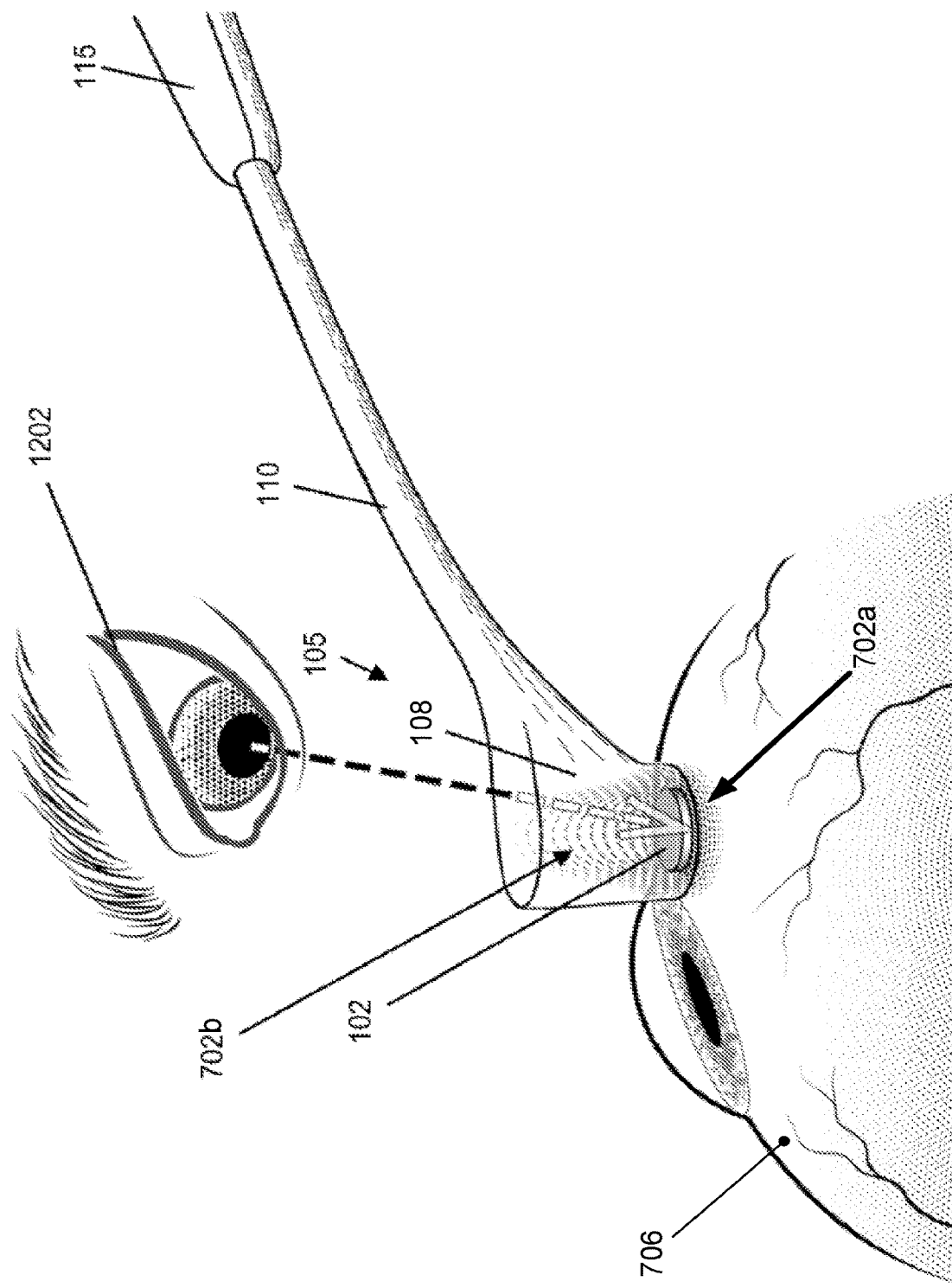
FIG. 13 illustrates a side, perspective view of the therapeutic applicator in use where a medical practitioner may clearly view the treatment surface on the patient's eyeball through the transparent body section of the module, permitting accurate and confirmable placement of the radiation source on the eyeball during the treatment.

Referring now to FIG. 13, this figure illustrates a side, perspective view of the therapeutic applicator in use where a medical practitioner 1202, (shown here much closer to the device than in actual use) may clearly view the treatment surface 102 on the patient's eyeball 706 through the transparent body section 108 of the module 105, permitting accurate and confirmable placement of the radiation source 102 on the eyeball 706 during the treatment. The radiation 702a that is attenuated by the patient's tissues 706 as the treatment dose 702 is represented as closely spaced, dotted isodose curves 702a beneath the disc shaped radiation source 102.

The radiation 702b attenuated, and thus shielded from affecting the practitioner and other operating room personnel, is represented here as dotted iso-gradient lines 702b within the device's body section 108 of the module 105. Thus, FIG. 13 illustrates a medical device 105 which, while delivering a suitable localized radiation dose 702a to the treatment surface of the patient's target tissues 706, allows the practitioner 1202 to view the site in a superior manner, and this configuration being a lightweight and highly maneuverable device, significantly enhances the delivery of accurate, safe and reliable brachytherapy.

Referring now to FIG. 14, this figure illustrates a perspective side view of a therapeutic applicator 100 which is also illustrated from a different view/angle in FIG. 15. The applicator 100 of FIG. 14 is illustrated with some shading to represent that it may be made from a material such as a leaded polymethyl methacrylate (PMMA-acrylic polymer).

Referring now to FIG. 15, this figure illustrates the therapeutic applicator 100 of FIG. 14 having a view 1702 through the body section 108 of the module 105 near a treatment site 706 which may be adjacent to the radiation source 102. The view 1702 may be magnified or presented without any magnification made by the body section 108 of the module 105. In the exemplary embodiment of FIG. 15, the treatment site 706 comprises eye tissue. However, other human tissues may be treated with the therapeutic applicator 100 without departing from the scope of this disclosure as understood by one of ordinary skill in the art.

Figure 16:
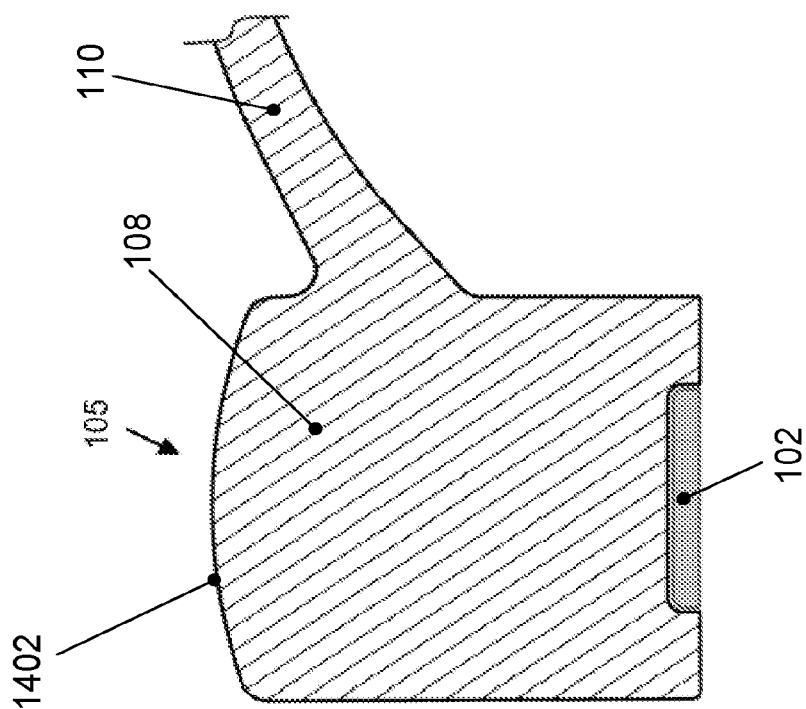
FIG. 16 illustrates a cross-sectional view of a module and a wand portion according to one exemplary embodiment which may magnify a view as a result of the lenticular contour of the module's surface.

Referring now to FIG. 16, this figure illustrates a cross-sectional view of a module 105 and a wand portion 110 according to one exemplary embodiment. According to this exemplary embodiment, the wand portion 110 is substantially smaller in its thickness relative to a thickness of the body section 108 of the module. For example, as shown in this FIG. 16, the thickness of the body portion is at least two times thicker than the thickness of the wand portion 110, as just an example.

As noted previously, the additional thickness of the body section 108 attenuates the radiation from the radioactive source 102. In this exemplary embodiment of FIG. 16, the body section 108 may comprise a cylindrical shape. Since the module 105, and particularly its body section 108 in this preferred exemplary embodiment is transparent, there exists the capability of augmenting the medical practitioner's view (1202—See FIG. 13) of the treatment site by shaping the surface 1402 of the module 105 to magnify the view. This surface 1402 may be characterized as a lenticular contour.

Figure 17:
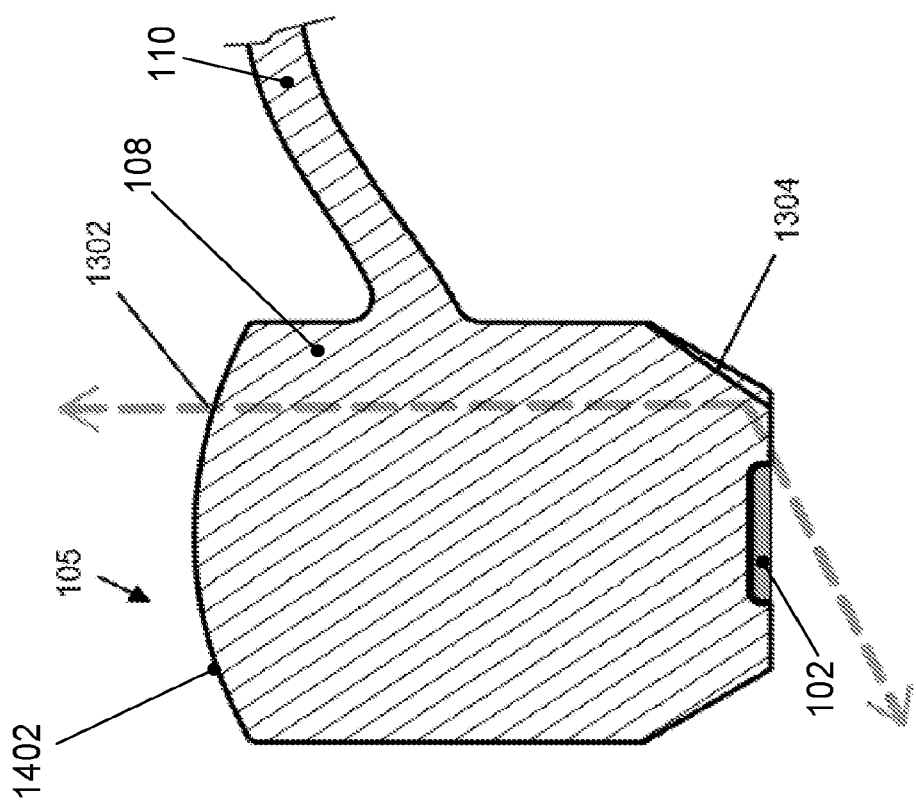
FIG. 17 illustrates a cross-sectional view of a module which may reflect or refract and magnify a view disposed beneath the radiation source as shown by a light ray.

Referring now to FIG. 17, this figure illustrates a cross-sectional view of a module 105 which may have a mirrored surface 1304 which reflects light as shown by a light ray 1302. The mirrored surface 1304 could be mounted or prismatic effects could be utilized such that through internal reflection and/or refraction of light 1302, the medical practitioner (1202—See FIG. 13, 1702 of FIG. 15) may view in useful directions through, and/or laterally to the patient contact surface during the procedure. The transparency of the module 104 affords the practitioner a largely unobstructed view (1202 of FIG. 13, 1702 of FIG. 15) of the treatment area surrounding the source 102 itself, thus enabling markers such as tissue dye to be seen through the device 100 facilitating accurate placement and conferring the ability to monitor placement and patient tissue conditions during treatment.

Figure 18:
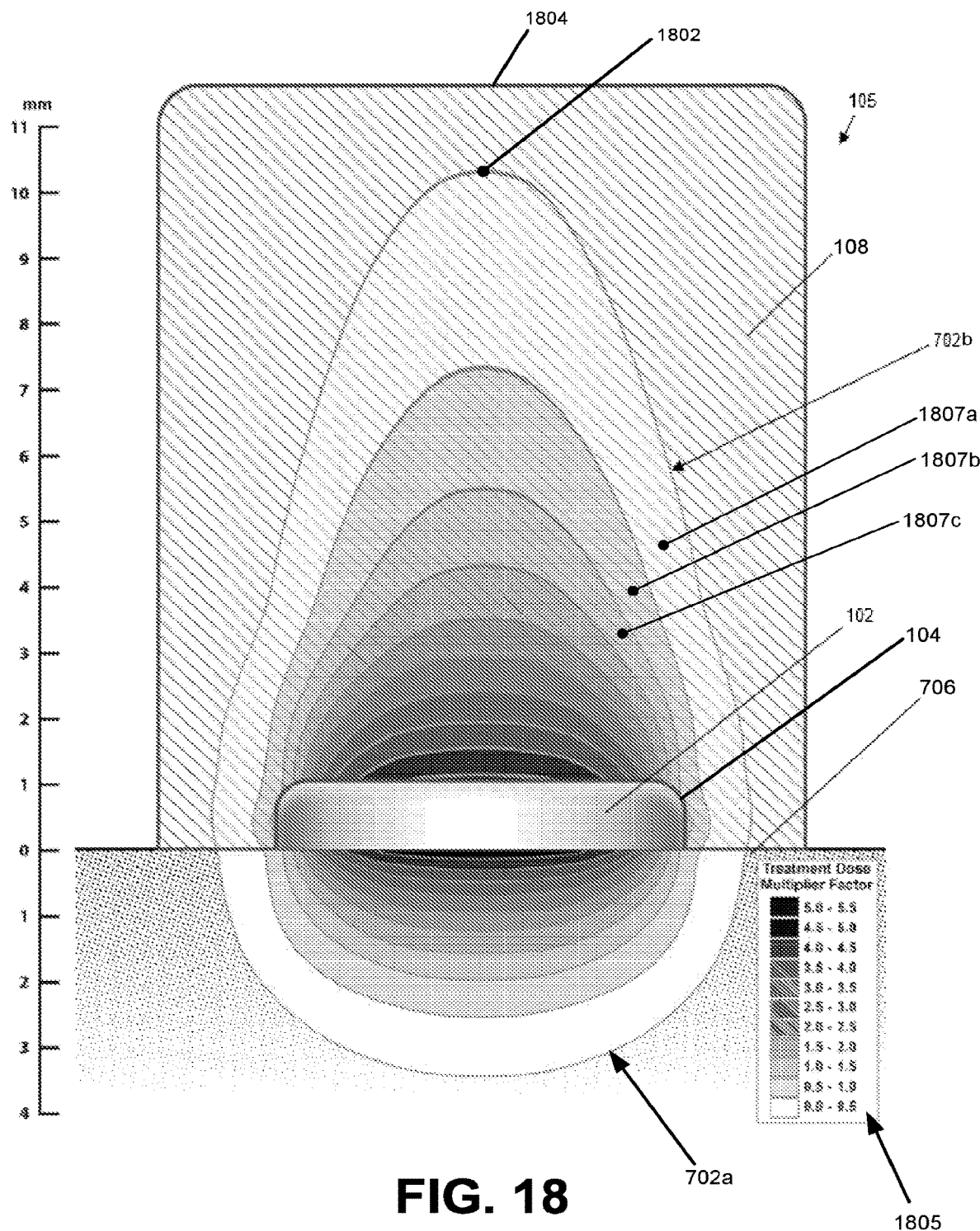
FIG. 18 illustrates radiation isodose profiles in a cross-sectional view of the body section of the module and in the treatment site, which usually comprises human tissue.

Referring now to FIG. 18, this figure illustrates radiation isodose profiles 702a, 702b within a cross-sectional view of the body section 108 of the module 105 and in the treatment site 706, which usually comprises human tissue. According to the exemplary embodiment illustrated in FIG. 18, the radiation source 102 may comprise a beta radiation emitting source. Specifically, the radiation source 102 may comprise yttrium-90. However, other radiation sources are possible and are included within the scope of this disclosure.

FIG. 18 illustrates a cross section through the cylindrical shaped section body 108 above and a treatment surface 706 that includes patient's tissues below the zero plane. FIG. 18 includes a plot of radiation intensity levels 702b from the radiation source 102 within the section body 108 and radiation levels 702a below the radiation source 102 in human tissue 706.

The radiation intensity levels 702b above the radiation source 102 falls off in intensity as one measures its intensity at progressive distances from the radiation source 102 within the section body 108. That is, the section body 108 due to its thickness of its transparent material absorbs most of the radiation 702b being emitted above the radiation source 102. In the tissues at the treatment surface 706 below the radiation source 102, this represents the delivered radiation dose 702a to the tissue 706. The falloff rate and radiation pattern 702b will usually vary based on the type of the radionuclide source 702 that is chosen.

In the section body 108, the radiation intensity plot 702b decreases with increasing distances above the radiation source 102. The thickness of the section body 108 is generally selected such that the radiation 702b above the source 102 generally stops or ends at a point 1802 just below the surface 1802 of the transparent material forming the section body 108. In the exemplary embodiment illustrated in FIG. 18, point 1802 is about 10.3 mm from the treatment surface 706 (i.e. the zero axis in FIG. 18). This plot 702b of radiation intensity above the radiation source 102 demonstrates that radiation emissions received by medical personnel in near the surface 1804 of the module 105 are very low and/or negligible.

FIG. 18 further illustrates a treatment dose multiplier factor key 1805 which corresponds to some gray-scale shading positioned within the module 105 and tissue 706. The gray-scale shading in FIG. 18, and specifically, the contour shading within the module 105 and the tissue 706, represents radiation being emitted by the radiation source 102. The term "treatment dose multiplier factor" refers to a non-specific target dosage amount or level which is assigned to each contour shaded region illustrated in FIG. 18.

A series of gray-scale shaded contours 1807a, 1807b, and 1807c corresponding to the radiation field 702b are shown in the diagram. These contours indicate progressive levels of radiation dosage/strength, where each shade/contour represents a radiation level being emitted from the radiation source 102 as the source 102 emits radiation into the body 108 of the module 105 and into the tissue 706 of a patient.

For example, the outermost shaded contour 1807a, according to the factor key 1805, may have a multiplier factor between 0.0 to 0.5 (the lowest factor of key 1805) that is multiplied against a base level of radiation being emitted by the radiation source 102. Similarly, the second outermost shaded contour 1807b, according to the factor key 1805, may have a multiplier factor between 0.5 to 1.0 (the second factor of key 1805) that is multiplied against a base level of radiation being emitted by the radiation source 102. Similarly, the third outermost shaded contour 1807c, according to the factor key 1805, may have a multiplier factor between 1.0 to 1.5 (the third factor of key 1805) that is multiplied against a base level of radiation being emitted by the radiation source 102.

The remaining shaded contours 1807 or dosage curves 1807 are assigned the values as shown in key 1805 corresponding to their levels of shading. These dosage curves 1807, which are really three-dimensional plotted surfaces seen in cross-section for this view shown in FIG. 18, may also be referred to in this disclosure as isodose contours.

Referring now to FIG. 19, this figure illustrates a cross-sectional view of an exemplary embodiment for a module 105 with a movable core element 1602 that is in a first position. In this first position, the radiation source 102, which is coupled to the movable core element 1602, is present within the section body 108 at a first depth.

Referring now to FIG. 20, this figure illustrates a cross-sectional view of an exemplary embodiment of the module 105 where the movable core element 1602 is in a second position relative to the first position shown in FIG. 19. In this second position, the radiation source 102, which is coupled to the movable core element 1602, is present within the section body 108 at a second depth which is less than the first depth shown in FIG. 19.

Referring now to FIG. 21, this figure illustrates a cross-sectional view of an exemplary embodiment of the module 105 where the movable core element 1602 is in a third position relative to the first and second positions shown in FIGS. 19-20. In this third position, the radiation source 102, which is coupled to the movable core element 1602, is present within the section body 108 at a third depth which is less than the first depth shown in FIG. 19 and the second depth shown in FIG. 20.

This third depth of FIG. 21 may be the same magnitude Th1 as described in connection with FIG. 6C described above. Further, the first and second depths for FIGS. 19-20 may be similar and/or equal to the depths described above in connection with the exemplary embodiments illustrated in FIGS. 9-10 which are described above.

There are multiple benefits for the exemplary embodiments illustrated in FIGS. 19-21: It may allow simple adaptation to differing amounts of recess for the source 102, as described above as a means to limit lateral spread of radiation, by selecting a retraction amount in advance of use. It would also allow the device's shielding module to be pre-positioned prior to use without the radionuclide 102 in place, which could prove useful in mitigating pre-treatment exposure to both the patient and personnel should the positioning of the module 105 be anticipated to be a troublesome process.

Figure 22:
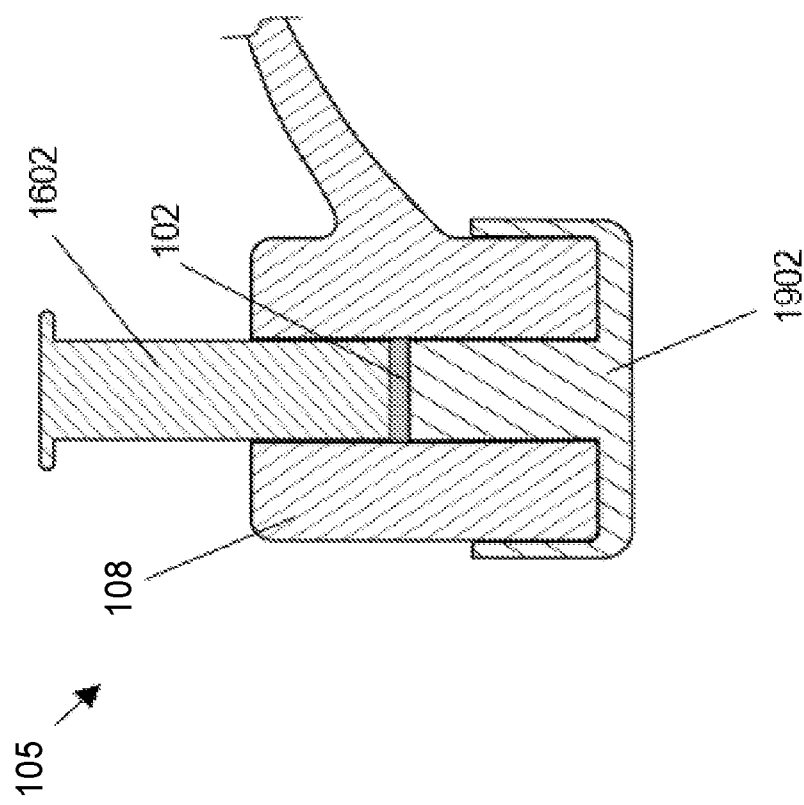
FIG. 22 illustrates another exemplary embodiment of a cross-sectional view of the module with a movable core element in addition to a shielding cap.

Referring now to FIG. 22, this figure illustrates another exemplary embodiment of a cross-sectional view of the module 105 with a movable core element 1602 in addition to a shielding cap 1902. The removable shielding cap 1902 may attenuate radiation emanating from the patient-facing side of the module 105 prior to use.

Figure 23:
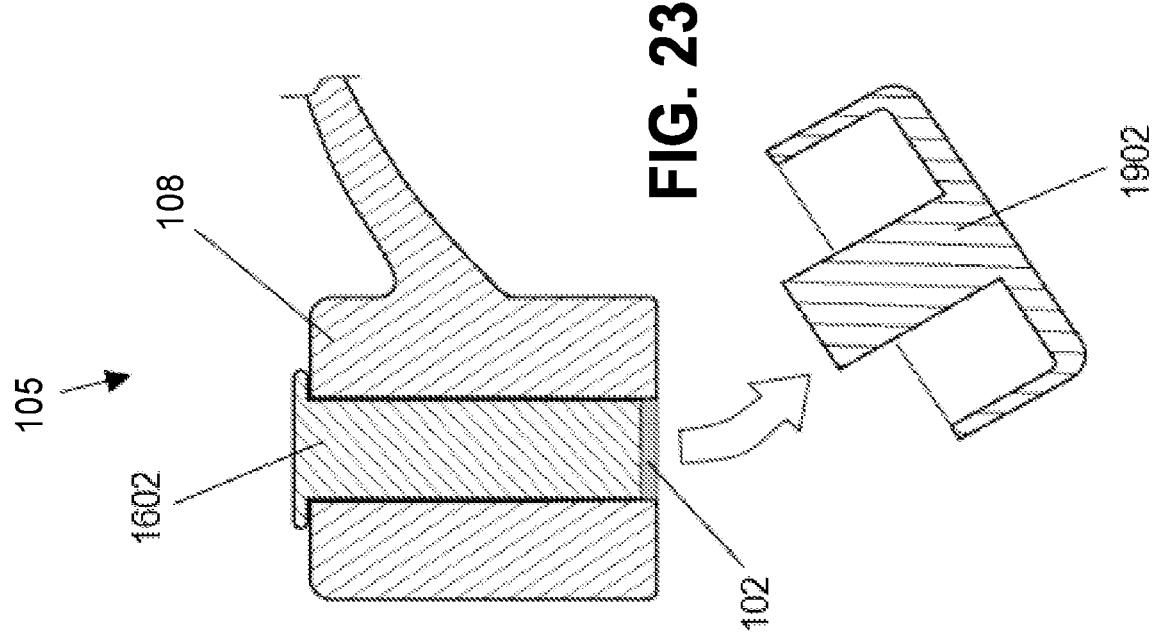
FIG. 23 illustrates another exemplary embodiment of a cross-sectional view of the module of FIG. 22 with a movable core element where the shielding cap has been removed.

Referring now to FIG. 23, this figure illustrates another exemplary embodiment of a cross-sectional view of the module 105 of FIG. 22 with a movable core element 1602 where the shielding cap 1902 has been removed. The cap 1902 is generally removed prior to treating tissue/the treatment site 706 (see FIG. 18). During treatment with the cap 1902 removed, the core element 1602 with radiation source 102 attached would be lowered into a selected position at the time of use as illustrated in FIG. 23, or into a recessed position such as the examples shown on FIGS. 19 & 20.

Figure 24:
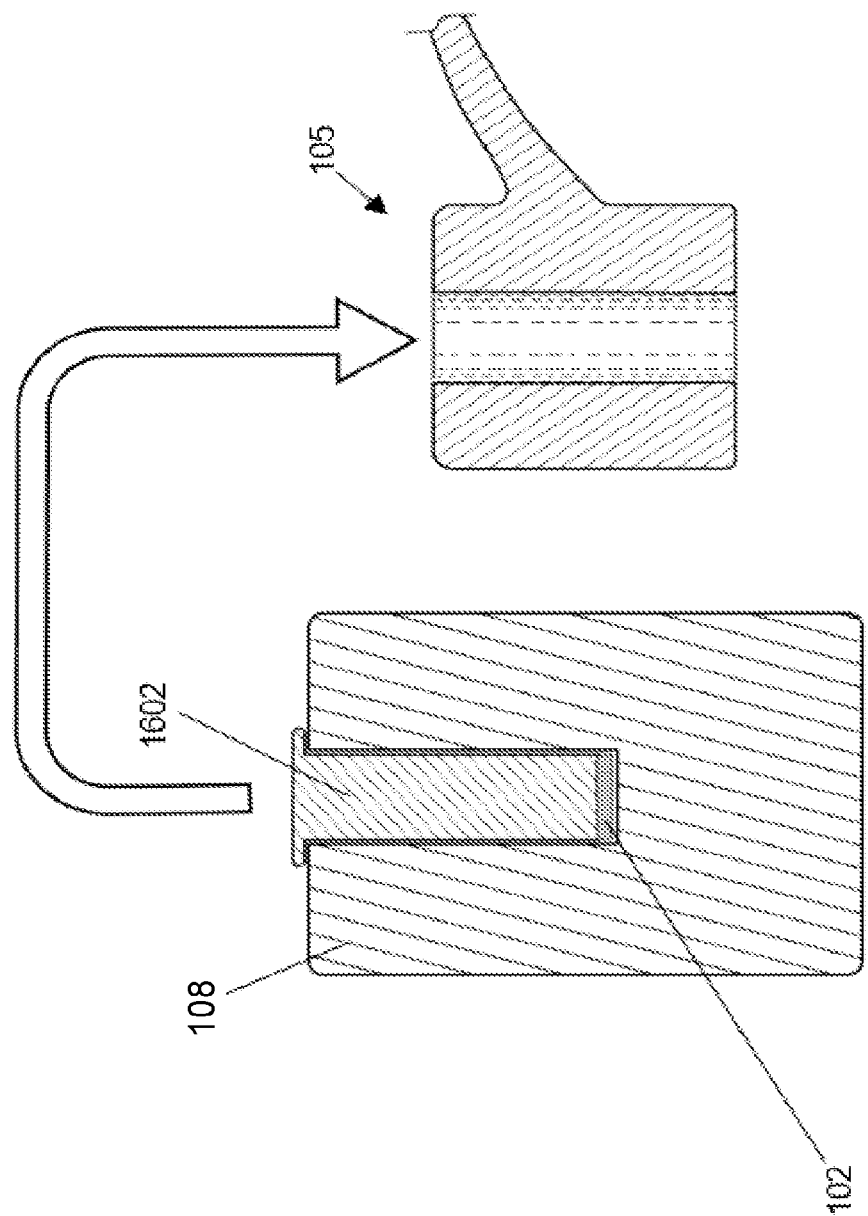
FIG. 24 illustrates how a module having a movable core element could be shipped and stored in a separate container prior to use in an operating room (O/R)

Referring now to FIG. 24, this figure illustrates how a module 105 having a movable core element 1602 could be shipped and stored in a separate container 2002 prior to use in an operating room (O/R). When the container 2002 with movable core 1602 arrives at the O/R, the movable core 1602 may be removed from the container 2002 where the core 1602 may then be inserted into the central portion of the module 105 as shown by the arrow.

Referring now to FIG. 25A, this figure illustrates a side view of an alternative exemplary embodiment for the module 105 illustrated in FIGS. 19-24 where the module 105 comprises a threaded core element 1602'. The threaded core element 1602' mates with the body 108 of the module 105. The thread 2502 may move the core element 1602' up or down when the core element 1602' is rotated within the body 108. As understood by one of ordinary skill in the art, the pitch and depth of the thread 2502 may be adjusted compared to what is illustrated without departing from the scope of this disclosure.

Referring now to FIG. 25B, this figure illustrates a side view of the threaded core element 1602' in a slightly elevated position relative to the position shown in FIG. 25A. As noted previously, similar to the exemplary embodiment illustrated in FIG. 9, this elevated position of the core element 1602' having a radiation source 102 may produce a different radiation pattern where the radiation pattern is narrower compared to the pattern which may be produced by the source 102 of FIG. 25A, which is not elevated within the body 108.

Referring now to FIG. 25C, this figure illustrates a side view of the threaded core element 1602' in a slightly elevated position relative to the position shown in FIG. 25B. As noted previously, similar to the exemplary embodiment illustrated in FIG. 9, this elevated position of the core element 1602' having a radiation source 102 may produce a different radiation pattern where the radiation pattern is more narrow compared to the pattern which may be produced by the source 102 of FIG. 25B, which is elevated relative to FIG. 25A, but less elevated than the position of the source 102 depicted in FIG. 25C.

Referring now to FIG. 26A, this figure illustrates an exemplary embodiment of a movable core 1602 with a mating cap 2602 for a module 105. The mating cap 2602 is provided and secured to the module 105 after the movable core 1602 has been adjusted to a desired position within the body 108. The mating cap 2602 prevents movement of the core 1602 once it couples to the cap 1602.

Referring now to FIG. 26B, this figure illustrates an exemplary embodiment of a movable core 1602 of a module 105 engaging a mating cap 2602 after the core 1602 has been moved to an elevated position relative to the position shown in FIG. 26A. The mating cap 2602 in this exemplary embodiment may a thickness greater than the thickness shown in FIG. 26A. With this additional thickness in FIG. 26B, the cap 2602 may grasp at an additional height of the movable core 1602 relative to the height of the cap 2602 shown in FIG. 26B.

Referring now to FIG. 26C, this figure illustrates an exemplary embodiment of a movable core 1602 of a module 105 engaging a mating cap 2602 after the core 1602 has been moved to an elevated position relative to the positions shown in FIG. 26A and FIG. 26B. The mating cap 2602 of FIG. 26C has a thickness which is slightly greater than the thicknesses of the caps 2602 illustrated in FIGS. 26A-26B. With this additional thickness in FIG. 26C, the cap 2602 may grasp at an additional height of the movable core 1602 relative to the height of the cap 2602 shown in FIG. 26B With this additional thickness in FIG. 26B, the cap 2602 may grasp at an additional height of the movable core 1602 relative to the height of the cap 2602 shown in FIGS. 26A-B.

As noted previously, this additional height within the core 108 will usually produce a more narrow radiation field produced by the radiation source 102 compared to the radiation fields produced by the sources 102 in FIGS. 26A-26B. As previously noted, increased radiation source distance by moving the core 1602 within the body 108 usually narrows the penumbra (side-scatter) and thus focuses the radiation compared to unshielded radiation sources 102. See FIGS. 8-9 described above which show how the height within the core 108 may impact the resultant radiation fields 702.

Referring now to FIG. 26D, this figure illustrates a side, perspective view of a cap 2602 alone and without being in contact with a core 1602 or module 108. The cap 2602 may be made from plastic, rubber, ceramic, metals, and other like materials which can also help shield radiation being emitted from a radiation source 102 and held within a module 105. Generally, the cap 2602 is usually made from a transparent material to allow light to may pass through it, similar to the material of the module 105, so that the treatment area 706 (see FIG. 7A) may be visible to the medical practitioner.

Referring now to FIG. 27A, this figure illustrates a side perspective view of a module 105 which contains or holds a disk-shaped radiation source 102A. As noted previously, the radiation source 102 may comprise any one of several different shapes, such as, but not limited to, round/disk-shaped, square, rectangular, obround, elliptical, and other like polygonal shapes as understood by one of ordinary skill in the art. Generally, the module 105 and its body 108 will take on a geometry that is similar to the geometry of the radiation source 102. In the exemplary embodiment illustrated in FIG. 27A, the body 108A may comprise a substantially cylindrical shape.

Referring now to FIG. 27B, this figure illustrates a side perspective view of a module 105 which contains or holds a rectangular radiation source 102B. The body 108B of the module 105 may comprise a prismatic member having a near rectangular cross-sectional shape.

Referring now to FIG. 27C, this figure illustrates a side perspective view of a module 105 which contains or holds an obround radiation source 102C. The body 108C of the module 105 may comprise a prismatic member having a near obround cross-sectional shape.

Referring now to FIG. 27D, this figure illustrates a side perspective view of a module 105 which contains or holds a plurality of small, prismatic radiation sources 102D, which may also be characterized as seeds 102D. Eight small sources or seeds 102 are illustrated in FIG. 27D. The small sources 102 may be contained within pockets or recesses formed by the module 105. Fewer, or a greater number of seeds/sources 102 are possible. Similarly smaller or larger seeds/sources 102 are also possible and are included within the scope of this disclosure. The body 108D of the module 105 may comprise a prismatic member having a near circular cross-sectional shape.

Referring now to FIG. 27E, this figure illustrates a side perspective view of a module 105 which contains or holds a plurality of small, prismatic radiation sources or seeds 102E positioned within a material 2702. The material 2702 may comprise an adhesive, such as glue or potting material, or any combination thereof. The material 2702 may be positioned within recess 104 of the module body 108E. Alternatively, instead of a material, the outlined structure 2702 of FIG. 27E may comprise a sub-container 2702 having a disk-shape.

However, other shapes for the sub-container 2702 are possible and are included within the scope of this disclosure. Other shapes may include, but are not limited to, obround, rectangular, elliptical, tubular, square, and other polygonal shapes. Eight small sources 102 are positioned within the sub-container 2702 of FIG. 27E. Fewer, or a greater number of seeds/sources 102 are possible. Similarly smaller or larger seeds/sources 102 are also possible and are included within the scope of this disclosure.

Referring now to FIG. 27F, this figure illustrates a cross-sectional view of the module 105 of FIG. 27E. In the exemplary embodiment of FIG. 27F, the structure 2702 comprises an adhesive, such as, but not limited to, glue and/or potting material as understood by one of ordinary skill in the art. The geometry of the seeds/sources 102E1 are more clearly illustrated in this FIG. 27F. Each seed/source 102E1 of FIG. 27 comprises a substantially cylindrical shape. However, other geometrical shapes for the seeds/small sources 102E1 are possible and are included within the scope of this disclosure. Other shapes for the seeds 102E1 include, but are not limited to, those shapes of the module bodies 108 illustrated in FIGS. 27B-27C which include rectangular prisms and obround prisms, as well as others, like square prisms, triangular prisms, and other polygonal shapes.

Further, as mentioned above, the radiation source 102 may comprise a plurality of seeds or separate elements which may be contained in a sub-container 2702 (see FIGS. 27E-27F described below). The sub-container 2702 of FIGS. 27E-27F may take on or encompass any one of the mechanical mounting configurations for the module 105 illustrated in FIGS. 6A-6G as understood by one of ordinary skill in the art. Additionally, anyone of the non-seed sources 102A-102C of FIGS. 27A-27C may also take on or encompass any one of the mechanical mounting configurations for the module 105 illustrated in FIGS. 6A-6G as understood by one of ordinary skill in the art.

Referring now to FIG. 28A, this figure illustrates an elevational perspective view of a therapeutic applicator 100' according to another exemplary embodiment having a module 105 with at least three functions and a wand portion 110 which does not have any tapered portion 505. Compared to FIGS. 4A & 5B which have tapered portions 505 extending from a body 108A of a module towards the wand portion 110, the wand portion 110 of the applicator 100' does not have any tapered portion 505. Instead, the wand portion 110 may have a uniform cross-sectional shape that directly connects/couples to the body 108 of module 105 as shown in FIG. 28A.

Referring now to FIG. 28B, this figure illustrates a side cross-sectional view of the module 105 illustrated in FIG. 28A. As more clearly visible in this this figure, the cross-sectional shape of the wand portion 110 may remain constant at the point/section where the wand portion 110 joins the body 108A of the module 105.

Referring now to FIG. 28C, this figure illustrates a bottom view of the module 105 illustrated in FIGS. 28A-28B. The wand portion 110 joins the body 108A of the module 105 with a constant cross-section.

Referring now to FIG. 29A, this figure illustrates a perspective view of a module 105 that is encased within a metallic outer jacket 2904. The module body 108A may comprise a generally cylindrical shape as illustrated and as described in previous embodiments. In this exemplary embodiment, the top of the module body 108A may have a substantially flat surface 2902. Exemplary metals for the jacket 2904 include, but are not limited to, stainless steel, titanium, tantalum, platinum, and palladium, and/or alloys thereof, including, nickel-chromium-iron alloys (i.e. sold under the brand INCONEL™ as of this writing), and a complex nickel-copper-iron alloy (i.e. sold under the brand MONEL™ as of this writing). just to name a few. Other metals are possible and are included within the scope of this disclosure as understood by one of ordinary skill in the art.

Referring now to FIG. 29B, this figure illustrates a cross-sectional view of the exemplary embodiment of the module 105 illustrated in FIG. 29A. This FIG. 29B demonstrates how the wand portion 110 may be integral with the metallic outer jacket 2904. In other words, the wand portion 110 and outer jacket 2904 may be formed from a single material, like metal. The metal can be poured into a single mold where the wand portion 110 and module casing are continuous. This means the wand portion 110 may be made of solid metal according to this exemplary embodiment.

Alternatively, an injection moldable metal-laden polymer may be used, such as Eco-Mass™. Such injection moldable metal-laden polymer methods are well understood by one of ordinary skill in the art. Alternative materials to polymers include, but are not limited to, glasses, crystalline materials, and any combination thereof.

As illustrated in FIG. 29B, the module 105 may receive a disk-shaped radiation source 102A. However, as described previously, other sources 102 having different shapes and sizes are possible and are included within the scope of this disclosure. In other words, any one or a combination of the sources 102 illustrated in FIGS. 27A-27F may be used with this exemplary embodiment and all other embodiments described previously.

With the flat surface 2902 of the module 105 illustrated in FIGS. 29A-29B, a medical practitioner may see areas around the source 102 without any magnification of the areas, as described above in connection with FIG. 15. The metallic outer jacket 2904 of this exemplary embodiment of FIGS. 29A-29B may block unwanted emissions of ionizing radiation (e.g. bremsstrahlung, beta, gamma, x-rays) in directions away from the treatment area.

The low impedance (Z) material of the polymer-based module 105 may more gradually absorb beta particle emissions, without generating significant amounts of bremsstrahlung photon radiation. However, the addition of a metal jacket 2904 may provide additional shielding against any such high-energy x-ray emissions from the radioactive source 102A. With the possible use of higher energy radionuclides for the source 102A, this additional shielding from the metal jacket 2904 may be necessary to reduce the overall dimension of the module 105 for best utility in a surgical environment.

Relative to conventional solid metal medical instruments, the metal jacket 2904 offers significant benefits: less weight due to less metal employed (compared to conventional solid metal instruments); while offering additional radioactive shielding beyond the shielding offered by polymer materials of the device such that the metal may block high-energy x-ray emissions from the source 102A. Thus, the material most proximate to the radiation source is the low-density material that can absorb beta radiation without producing significant quantities of unwanted radiation, while the outer metal jacket acts to block the remaining emission of these unwanted types of high energy radiation.

Typically, a medical practitioner using the applicator 100 of FIGS. 29A-29B may make targeting marks 3004 (see FIG. 30B) on the one or more tissues 3205 (see FIG. 32A) to be treated with the source 102A prior to the procedure. So preferably, the module 105 and its cylindrical body 108A are transparent, as described above, to allow the medical practitioner to view these marks 3004 for accurate placement of the radioactive source 102 adjacent to and/or on the treatment site.

Referring now to FIG. 30A, this figure illustrates a perspective view of a module 105 that is encased within a metallic outer jacket 2904 and having a convex surface 3002. The module body 108A may comprise a generally cylindrical shape as described in previous embodiments. In this exemplary embodiment, the top of the module body 108A may have a substantially convex surface 3002, compared to the flat surface 2902 of FIGS. 29A-29B.

Referring now to FIG. 30B, this figure illustrates a cross-sectional view of the exemplary embodiment of the module 105 illustrated in FIG. 30A. This FIG. 30B, like FIG. 29B, demonstrates how the wand portion 110 may be integral with the metallic outer jacket 2904. In other words, the wand portion 110 and outer jacket 2904 may be formed from a single material, like metal.

Figures 30C, 30D:
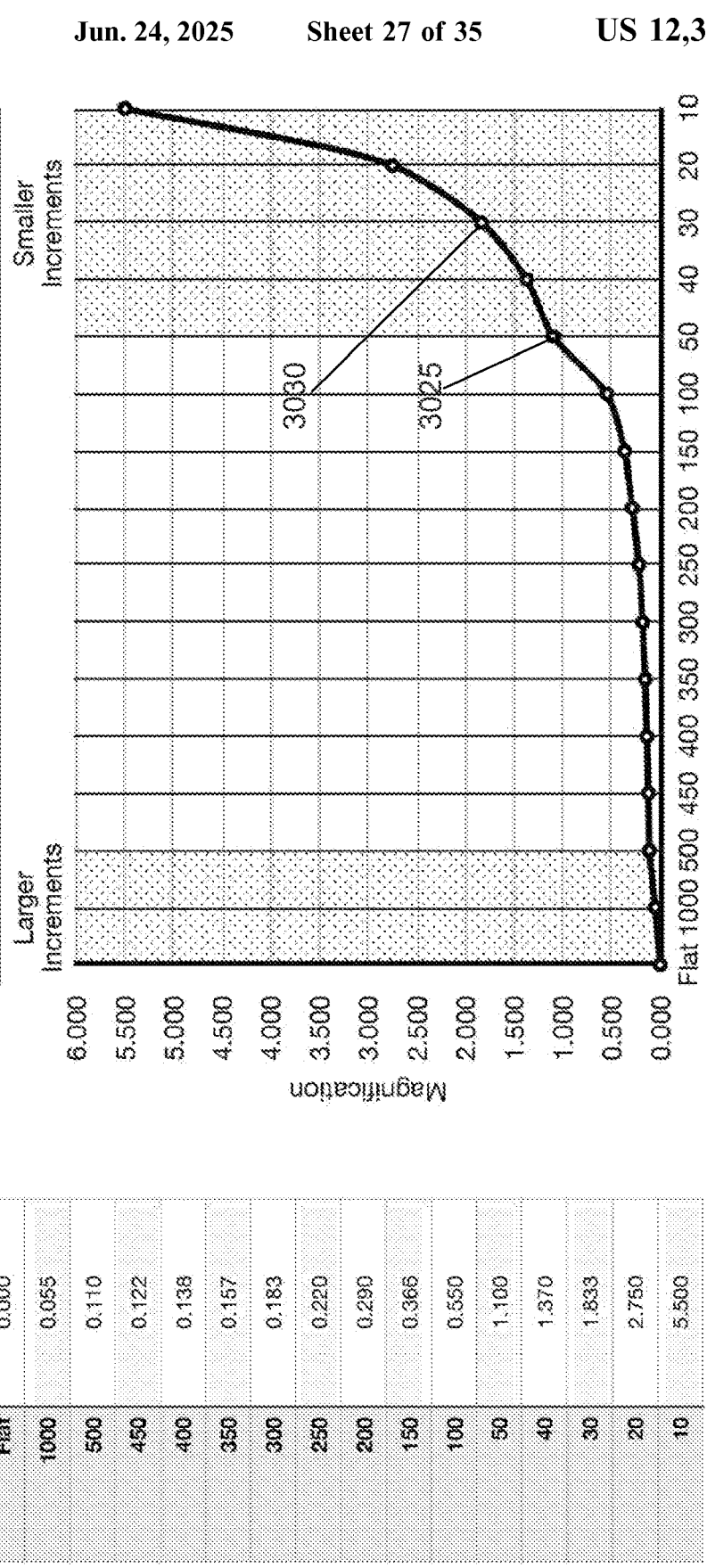
FIG. 30C illustrates an exemplary chart of radius of curvature values for the convex surface versus (vs.) magnification of an object viewed through the convex surface.
FIG. 30D illustrates magnification values on the y-axis plotted against radius of curvature values in centimeters (cm) for an 11 mm tall shielding module having a refractive index of 1.55.

The convex surface 3002 of FIGS. 30A-30B may function as a lens in accordance with its radius of curvature. Referring now to FIG. 30C, this figure illustrates an exemplary chart of radius of curvature values for the convex surface 3002 versus (vs.) magnification of an object viewed through the convex surface 3002. The left-hand side 3020 of the chart in FIG. 30C lists values of a radius of curvature for the convex surface 3002 in centimeters (cm) 3002 while the right-hand side 3025 of the chart lists the resultant magnification from the radius of curvature.

Referring now to FIG. 30D, this figure illustrates magnification values on the y-axis plotted against radius of curvature values in centimeters (cm) on the x-axis for an 11 mm tall shielding module 108 having a refractive index of 1.55. As shown by the chart of FIG. 30C, point 3030 on the plot shows that a magnification value of about 1.10 will have a radius of curvature of about 50.0 cm. Similarly, point 3035 on the plot shows that a magnification value of 1.8 will have a radius of curvature of about 30.0 cm.

One of ordinary skill in the art will recognize that other sizes and materials for the module 108 are possible and are included within the scope of this disclosure. And these other sizes and materials will impact the refractive index, and thus, the radius of curvature for the module 108.

The radius of curvature for the surface 3002 may be adjusted for any number of magnification ranges. For example, exemplary magnifications between 1.0 times to about 100.0 times the original size are possible and are included within the scope of this disclosure.

Typically, the medical practitioner, such as a surgeon, may make targeting marks 3004 on the tissue(s) 3205 (see FIG. 32A) to be treated prior to the procedure. And these marks 3220 are usually made more visible by the magnification afforded by the lens produced by the convex surface 3002 as illustrated in FIGS. 30A, 30B, 31A, and 32A-32B.

Referring now to FIG. 31A, this figure illustrates a cross-sectional view of an exemplary embodiment of a therapeutic applicator 100, similar to the exemplary embodiment of FIGS. 29A-29B, but with a light source 3104 and a light guide 3102 to produce light rays 3106. The light source 3104 may comprise light emitting diodes (LEDs), laser diodes, quartz halogen lights, xenon metal halide lights, etc. The light source 3104 may be powered by alternating current (AC) or by a battery under direct current (DC). Other light sources 3104 are possible and are included within the scope of this disclosure as understood by one of ordinary skill in the art. The light guide 3102 may comprise a fiber-optic cable or a molded polymer material capable of acting as a light guide, such as polymethyl methacrylate (PMMA), polycarbonate, co-polyester, or another transparent material possessing a high enough index of refraction to optimally transmit/propagate light along its length.

Such illumination from the light source 3104 would travel/propagate along the length of the wand portion 110 of the light guide 3102 and would then advantageously reflect internally in the transparent shielding material to add additional illumination of the surgical marks 3004 with the light rays 3016 shown in FIG. 31A. This would serve to benefit usability since the presence of the metal jacket 2904 may limit the amount of ambient light available for such purposes.

Referring now to FIG. 31B, this figure illustrates a cross-sectional view of an exemplary embodiment of a therapeutic applicator 100 similar to the exemplary embodiment of FIGS. 30A-30B, but with a light source 3104 and a light guide 3102 to produce light rays 3106. The exemplary therapeutic applicator 100 of FIG. 31B operates similarly to the exemplary embodiment of the therapeutic applicator of FIG. 31A, except that the therapeutic applicator 100 of FIG. 31B has a convex surface 3002 which functions as magnifying lens as described above similar to FIGS. 30A-30B. Thus, the light rays 3106 for FIG. 31B will illuminate a surface while the convex surface 3002 magnifies the surface adjacent to the module body 108A.

Referring now to FIG. 31C, this figure is a cross-sectional view of an exemplary embodiment of a therapeutic applicator 100 which has a hollow module 108A filled with a transparent liquid 3109. The liquid 3109 generally has the same refractive index as the substantially flat top surface 2902 such that areas adjacent to the radiation source 102A remain visible for the medical practitioner similar to the solid module embodiments described previously, like FIG. 31A. While permitting light to propagate through the transparent liquid 3109, the liquid 3109 also shields against radiation being emitted by the source 102A. That is, the liquid 3109 may absorb and/or block any gamma or beta radiation which is emitted from the source 102A in order to protect the medical practitioner using the applicator 100. It is noted that using liquids 3109 with refractive indices different from the enclosing polymer for the hollow module 108A could provide additional optical magnifying capabilities as understood by one of ordinary skill in the art.

Exemplary liquids 3109 include, but are not limited to, water, silicone, polyethylene glycol (PEG), polypropylene glycol (PPG), polytetrahydrofuran (PTHF), polydimethylsiloxane (PDMS), and polymethylphenylsiloxane (PMPS), and high index optical gels often used for fiber optic couplings, etc. Other transparent liquids 3109 which also block/absorb radiation while permitting light propagation and visibility therethrough are possible and are included within the scope of this disclosure as understood by one of ordinary skill in the art.

In the exemplary embodiment illustrated in FIG. 31C, the wand portion 110 may be made from the same material as the hollow module 108A. These two structures may be integral relative to each other as illustrated.

Referring now to FIG. 31D, this figure is a cross-sectional view of an exemplary embodiment of a therapeutic applicator 100 which has a hollow module 108A filled with a transparent liquid 3109 and having a convex surface 3002 for magnifying tissue 3205 (see FIG. 32A) adjacent to the radioactive source 102A. That is, the applicator 100 of FIG. 31D, like FIGS. 30B & 31B, has a convex surface 3002 that magnifies the view of regions surrounding the radiation source 102A when viewed by the medical practitioner.

In this exemplary embodiment of FIG. 31D, the hollow module 108A has a top, convex surface 3002 which is also adjacent to the transparent liquid 3109. The transparent liquid 3109 and the convex surface 3002 generally have the same index of refraction in order to permit visibility through both the surface 3002 and the liquid 3109, as well as the bottom surface of the module 108A adjacent to the source 102A.

The transparent liquid 3109 was described above in connection with FIG. 31C. Similarly, the convex surface 3002 was also described previously in connection with several prior figures, such as FIGS. 30A-30B. However, the convex surface 3002 of FIG. 31D is part of the module body 108A which is hollow and contains liquid 3109. According to an alternative exemplary embodiment, the thickness of the hollow module 108A near the source 102A could be modulated/adjusted based on the type of transparent liquid 3109 contained by the module 108A. Further, the shape of the module 108A near the source 102A could be adjusted to conform to the underlying tissue 3205 (See FIG. 32A) if the underlying tissue 3205 had a non-uniform (i.e. not horizontal shape) surface.

Referring now to FIG. 31E, this figure illustrates a cross-sectional view of an exemplary embodiment of a therapeutic applicator 100 which has a hollow module 108A filled with a transparent liquid 3109 and with a metal casing 2904. The metal casing 2904 is similar to the metal casing described above in connection with FIGS. 29A-30B and will not be described further here. The metal casing 2904 may provide additional shielding against radiation being emitted from the radioactive source 102A. The transparent liquid 3109 may also be the same as described previously.

In this embodiment of FIG. 31E, the applicator 100 may have a flat, transparent surface 2902. This flat surface 2902 may be similar to that described above in connection with FIGS. 29A-29B, 31A, & 31C. The metal casing 2904 surrounding the module 108A may be integral with the wand portion 110 as described above.

Referring now to FIG. 31F, this figure illustrates a cross-sectional view of an exemplary embodiment of a therapeutic applicator 100 which has a hollow module 108A filled with a transparent liquid 3109 and having a metal casing 2904 along with a convex or curved surface 3002 for magnifying tissue 3205 (see FIG. 32A) adjacent to the radioactive source 102A. This exemplary embodiment of FIG. 31F may be substantially similar to the embodiment of FIG. 31E except that the top surface 3002 may be curved/convex to provide magnification of tissue 3205 (see FIG. 32A) as described previously. Like FIG. 31E, the metal casing surrounding the module 108A of FIG. 31F may be integral with the wand portion 110.

Referring now to FIG. 31G, this figure illustrates a cross-sectional view of an exemplary embodiment of a therapeutic applicator 100 which has a hollow module 108A filled with a transparent liquid 3109 and having both a metal casing 2904 and an optical waveguide 3102 with light source 3104. This embodiment of FIG. 31G is at least a combination of the embodiments found in FIGS. 31A, 31C, & 31E. The liquid 3109 may have a high and/or variable index of refraction for providing magnification as well as absorbing any radiation being emitted from the radioactive source 102A.

The metal casing 2904 of FIG. 31G may provide for additional shielding against any ionizing radiation being emitted from the source 102A, while the optical lightguide 3102 and light source 3104 may provide light rays 3106 for illuminating tissue 3205 (see FIG. 32A) that is adjacent to the radioactive source 102A. The transparent liquid 3109 and flat transparent viewing surface 2902 may function similarly to the prior embodiments described above, like FIG. 31E.

Referring now to FIG. 31H, this figure illustrates a cross-sectional view of an exemplary embodiment of a therapeutic applicator 100 which has a hollow module 108A filled with a transparent liquid 3109 and having both a metal casing 2904 and an optical waveguide 3102 with light source 3104 in addition to a convex/curved surface 3002. This exemplary embodiment combines several of the features described above in connection with at least FIGS. 31B & 31F.

Like FIG. 31B, the convex/curved surface 3002 of FIG. 31H may magnify a view of tissue 3205 (see FIG. 32A) that is positioned adjacent to the radioactive source 102A for treatment of the tissue 3205. Like FIGS. 31A & 31G, the wand portion 110 may comprise an optical waveguide 3102 that may propagate light rays 3106 generated by the light source 3104.

Figure 31I:
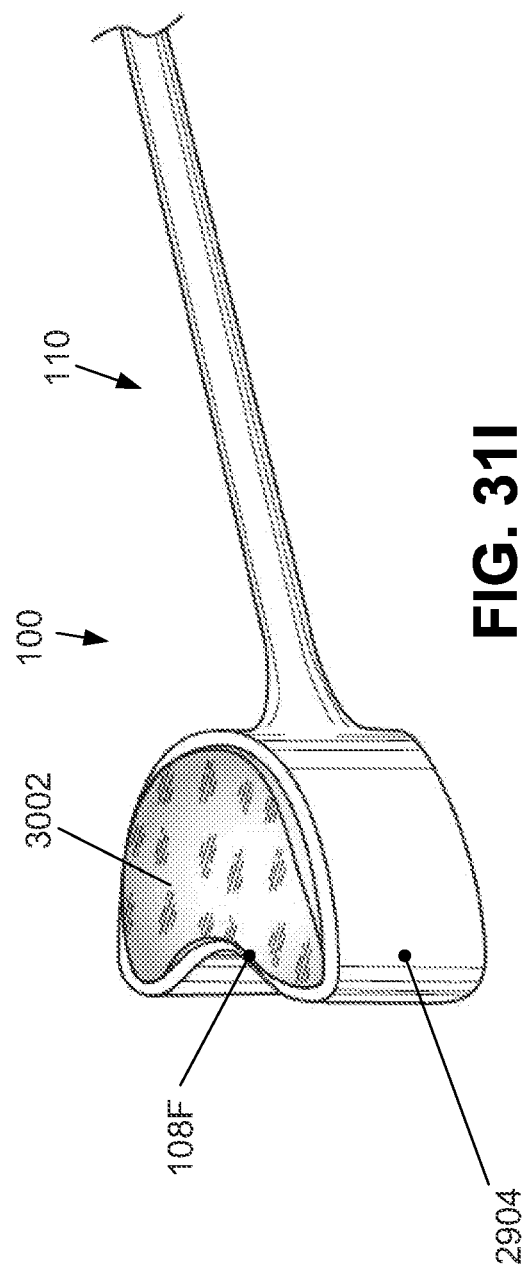
FIG. 31I illustrates a perspective view of an exemplary embodiment of a therapeutic applicator which has a hollow module having a kidney shape/geometry and which contains a transparent fluid.

Referring now to FIG. 31I, this figure illustrates a perspective view of an exemplary embodiment of a therapeutic applicator 100 which has a hollow module 108F having a kidney shape/geometry and which contains a transparent fluid 3109. The module 108F is hollow and has a convex/curved surface 3002 like the embodiment of FIGS. 31F & 31H. This embodiment of FIG. 31I also has a metal casing 2904 like that of FIGS. 31G & 31H. This embodiment demonstrates that the module 108F may be uniquely shaped to match the geometry of tissue 3205 or to circumvent an interfering anatomical feature adjacent to the treatment area. (see FIG. 32A.) Said treatment area is treated with the radiation source 102A (not visible in FIG. 31I, but see other Figures like FIG. 31H).

This embodiment of FIG. 31I may be characterized as a closed geometry since it does not envelope or enclose a substantial amount of empty space by its outer perimeter. The radiation source 102 of FIG. 31I (not visible in FIG.

31I) may have a unique geometry mirroring the kidney shape and/or it may have any of the variety of sources 102 described above in connection with FIGS. 27A-27F.

Figure 31J:
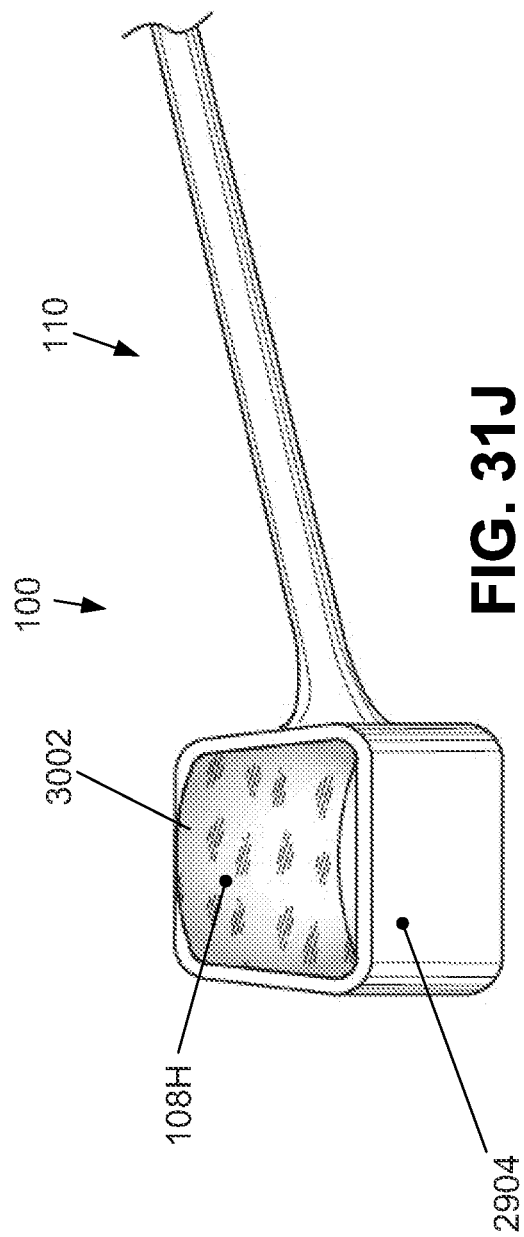
FIG. 31J illustrates a perspective view of an exemplary embodiment of a therapeutic applicator which has a hollow module having a rectangular prism/geometry and which contains a transparent fluid, similar to the embodiment illustrated in FIG. 27B.

Referring now to FIG. 31J, this figure illustrates a perspective view of an exemplary embodiment of a therapeutic applicator 100 which has a hollow module 108H having a rectangular prism/geometry and which contains a transparent fluid 3109, similar to the embodiment illustrated in FIG. 27B. The module 108H is hollow and has a convex/curved surface 3002 like the embodiment of FIGS. 31F & 31H. This embodiment of FIG. 31J also has a metal casing 2904 like that of FIGS. 31G, 31H, & 31I.

The radiation source 102B of FIG. 31J (not visible in FIG. 31I, but see FIG. 27B) may have a unique geometry mirroring the rectangular shape. Alternatively, the source 102 of FIG. 31I may have any of the variety of sources 102 described above in connection with FIGS. 27A-27F.

Figure 31K:
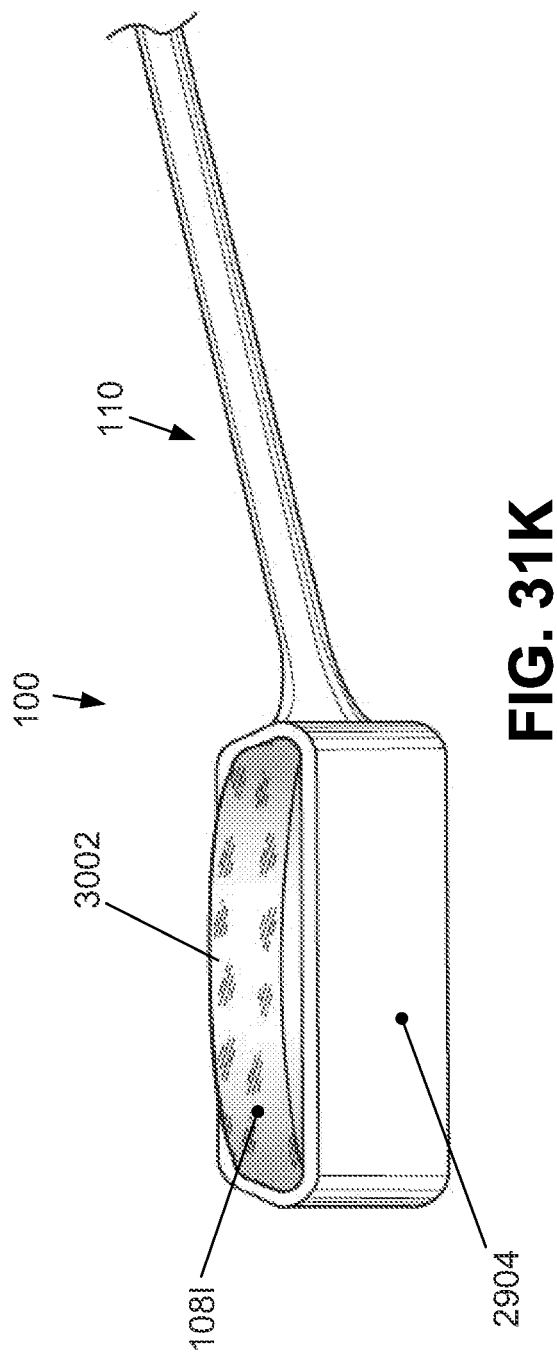
FIG. 31K illustrates a perspective view of an exemplary embodiment of a therapeutic applicator which has a hollow module 108I having a rectangular prism/geometry and which contains a transparent fluid, similar to the embodiment illustrated in FIGS. 27B & 31J.

Referring now to FIG. 31K, this figure illustrates a perspective view of an exemplary embodiment of a therapeutic applicator 100 which has a hollow module 108I having a rectangular prism/geometry and which contains a transparent fluid 3109, similar to the embodiment illustrated in FIGS. 27B & 31J. However, in this exemplary embodiment, the wand portion 110 is in alignment with a longest side of the rectangular geometry of the module 108I.

Meanwhile, the wand portion 110 of FIG. 31J is in alignment with a shorter side of the rectangular geometry of the module 108H. The module 108I is hollow and has a convex/curved surface 3002 like the embodiment of FIGS. 31F & 31H & 31J. This embodiment of FIG. 31L also has a metal casing 2904 like that of FIGS. 31G, 31H, 31I, & 31J.

The radiation source 102B of FIG. 31K (not visible in FIG. 31K, but see FIG. 27B) may have a unique geometry mirroring the rectangular shape. Alternatively, the source 102 of FIG. 31K may have any of the variety of sources 102 described above in connection with FIGS. 27A-27F.

Referring now to FIG. 32A, this figure illustrates an exemplary therapeutic applicator 100 having a convex surface 3002 that produces magnification, but the device does not have a wand portion or arm portion 110 which were described above in connection with FIGS. 29A-31B. Without a wand portion 110, a practitioner may grasp or hold the metal case 2904 (or module 108A itself if no case 2904) with his or her hand 3210. The convex surface 3002 still magnifies the tissue 3205 (see FIG. 32A) 3205 and markings 3004 which may be made by the medical practitioner to target certain tissue 3205 (see FIG. 32A) to be irradiated with the radiation source 102A (not visible in FIG. 32A, but see FIGS. 29A-31B).

While human eye tissue 3205 is one intended environment or use for the therapeutic applicator 100, other uses for the applicator 100 are possible. That is, the applicator 100 may be used on other tissue 3205 in the human body. For example, the applicator could be used on skin tissue 3205. And depending on the depth of radiation being emitted from the source 102A, other tissue 3205 below skin tissue could irradiated. Other surgical applications, beyond surgical eye applications are possible. Further, other applications beyond human ones are possible for the applicator 100 as understood by one of ordinary skill in the art: that is, animal tissue 3205 in a veterinary context may be another intended application/environment as understood by one of ordinary skill in the art.

Referring now to FIG. 32B, this figure illustrates an exemplary therapeutic applicator 100 having a convex surface 3002 that produces magnification along with a light waveguide 3102, but the device does not have a wand portion or arm portion 110 similar to FIG. 32A. This exemplary embodiment, like the embodiments of FIGS. 31A-31B may emit light rays 3106 near the tissue 3205 being irradiated with the radiation source 102A (not visible in FIG. 32B, but see FIGS. 31A-31B). A light source 3104 (not shown, but see FIGS. 31A-31B) produces the light rays 3106 and is coupled to an end of the optical waveguide 3102.

According to this exemplary embodiment of FIG. 32B, the light waveguide 3102 is not covered or coated with any metal like that of FIGS. 31A-31B. In this embodiment of FIG. 32B, only the module body 108A is surrounded or enveloped by the metal casing 2904. In this way, the light waveguide of this embodiment may be flexible.

The module body 108 should be thick enough to absorb radiation from the radiation source 102, whether the source 102 emits beta or gamma radiation. Beta radiation may be absorbed by water or plastic as they are clear. Meanwhile, gamma radiation may be absorbed and/or blocked by metals, such as the metal casing 2904 and/or liquids 3109 or solids containing metal material.

As noted previously, the metal casing 2904 described above may be formed with traditional molds in which metal is poured in liquid state to later harden into a solid state. Alternatively, an injection moldable metal-laden polymer may be used, such as eco-mass. Such injection moldable metal-laden polymers, such as Eco-Mass™, are well understood by one of ordinary skill in the art as of this writing.

Also, some embodiments in the several Figures are shown with metal casings 2904 and some are shown without metal casings 2904. It is clear to one of ordinary skill in the art that those embodiments not having metal casings 2904 can be provided with metal casings 2904 without departing from this disclosure, and vice-versa (i.e. metal casings 2904 may be dropped for those embodiments shown with casings 2904).

Certain steps in the processes or process flows enabled by the mechanical drawings described above naturally precede others for the invention to function as described. However, the invention is not limited to the order of the steps described if such order or sequence does not alter the functionality of the invention. That is, it is recognized that some steps may performed before, after, or parallel (substantially simultaneously with) other steps without departing from the scope and spirit of this disclosure. In some instances, certain steps may be omitted or not performed without departing from the invention.

Although a few embodiments have been described in detail above and illustrated in the several figures, those skilled in the art will readily appreciate that many modifications from those which were described and as illustrated are possible in the embodiments without materially departing from this disclosure. For example, several of the exemplary embodiments illustrated in the multiple figures may be combined without departing from the scope of this disclosure as understood by one of ordinary skill in the art. As but one example, the movable core embodiments of FIGS. 19-24 could be easily combined with the embodiments of FIGS. 6A-6D which have different radiation source mounts as well as with the embodiment of FIG. 10 which has an angled or flared wall 1002. Accordingly, such modifications are intended to be included within the scope of this disclosure as defined in the following claims.

While several mechanical configurations are illustrated in FIGS. 1-32B, it is possible that these mechanical configurations may be replaced/substituted by additional and/or fewer structures. Further, mechanical equivalents of any of the illustrated structures, such as the section body 108 of the module 105, could be substituted for many of the structures illustrated in the several views as understood by one of ordinary skill in the art. Such substitutions of mechanically equivalent structures are included within the scope of this disclosure.

Also, substances described in this disclosure may be substituted with equivalents as understood by one of ordinary skill in the art. While several branded substances have been referred to in this disclosure for several of the ingredients, other like ingredients sold under different brands and/or by different suppliers may be used without departing from the spirit and scope of this disclosure.

Further, in the claims, means-plus-function clauses (when used) are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

It is the express intention of the applicant not to invoke 35 U.S.C. § 112, sixth paragraph for any limitations of any of the claims herein (or in future cases), except for those in which the claim expressly uses the words 'means for' together with an associated function.

Therefore, although selected aspects have been illustrated and described in detail, it will be understood that various substitutions and alterations may be made therein without departing from the spirit and scope of the present invention, as defined by the following claims.

What is claimed is:

1. A therapeutic applicator comprising:
   a wand portion, the wand portion comprising a light guide made of a first transparent material;
   a module coupled to the wand portion, the module comprising a body section and a recess positioned within the body section, the body section comprising a prismatic member made of a second transparent material, the prismatic member contacting the light guide of the wand portion such that light may propagate from the light guide into the body section to illuminate the body section;
   a casing surrounding an outer surface of the module and the wand portion, the casing comprising a metal or metallic surface plating layer;
   the body section comprising a surface, the surface providing a view that includes a region surrounding the recess;
   a radiation source positioned within the recess, the body section having a thickness greater than a diameter of the radiation source which is sufficient to attenuate radiation being emitted from the radiation source while the transparent material of the body section allows visibility of a treatment site that is adjacent to the radiation source; and
   wherein the module comprising the prismatic member permits light to propagate therethrough and towards a treatment surface while also absorbing radiation being emitted by the radiation source.

2. The applicator of claim 1, wherein the applicator is coupled to a light source.

3. The applicator of claim 2, wherein the light source comprises at least one of a light emitting diode, a laser diode, a halogen light, a halide light, or any combination thereof.

4. The applicator of claim 1, wherein the metal comprises at least one of: stainless steel, titanium, tantalum, platinum, palladium, a metal alloy, a nickel-chromium-iron alloy, and a complex nickel-copper-iron alloy, or any combination thereof.

5. The applicator of claim 1, wherein the first transparent material comprises at least one of: polymethyl methacrylate (PMMA), a polycarbonate, a co-polyester, or any combination thereof.

6. The applicator of claim 5, wherein the second transparent material comprises at least one of a: co-polyester, polyethylene terephthalate, polycarbonate, polysulfone, leaded polymethyl methacrylate, glass, or any combination thereof.

7. The applicator of claim 1, wherein the first transparent material and the second transparent material comprise a same transparent material.

8. The applicator of claim 1, wherein the radiation source comprises at least one of a circular shape, a square shape, a rectangular shape, an obround shape, an elliptical shape, and a seed shape.

9. The applicator of claim 8, wherein the radiation source has a thickness which is less than a thickness of the body section.

10. The applicator of claim 1, wherein the radiation source comprises at least one of: $^9$Sr, $^{169}$Yb, $^{90}$Y, $^{192}$Ir, $^{103}$Pd, $^{177}$Lu, $^{149}$Pm, $^{140}$La, $^{153}$Sm, $^{186}$Re, $^{188}$Re, $^{166}$Ho, $^{166}$Dy, $^{137}$Cs, $^{57}$Co, $^{169}$Er, $^{165}$Dy, $^{97}$Ru, $^{193m}$Pt, $^{195m}$Pt, $^{105}$Rh, $^{68}$Ni, $^{67}$C, $^{64}$Cu, $^{109}$Cd, $^{111}$Ag, $^{198}$Au, $^{199}$Au, $^{201}$Tl, $^{175}$Yb, $^{47}$Sc, $^{159}$Gd, and $^{212}$Bi, or a combination thereof.

11. A therapeutic applicator comprising:
    a light source for emitting light;
    a wand portion coupled to the light source, the wand portion comprising a light guide made of a first transparent material;
    a module coupled to the wand portion, the module comprising a body section and a recess positioned within the body section, the body section comprising a prismatic member made of a second transparent material, the prismatic member contacting the light guide of the wand portion such that light emitted by the light source may propagate from the light guide into the body section to illuminate the body section;
    a casing surrounding an outer surface of the module and the wand portion, the casing comprising metal;
    the body section comprising a surface, the surface providing a view that includes a region surrounding the recess;
    a radiation source positioned within the recess, the body section having a thickness greater than a diameter of the radiation source which is sufficient to attenuate radiation being emitted from the radiation source while the transparent material of the body section allows visibility of a treatment site that is adjacent to the radiation source; and
    wherein the module comprising the prismatic member permits light from the light source to propagate therethrough and towards a treatment surface while also absorbing radiation being emitted by the radiation source.

12. The applicator of claim 11, wherein the light source comprises at least one of a light emitting diode, a laser diode, a halogen light, a halide light, or any combination thereof.

13. The applicator of claim 11, wherein the metal comprises at least one of: stainless steel, titanium, tantalum, platinum, palladium, a metal alloy, a nickel-chromium-iron alloy, and a complex nickel-copper-iron alloy, or any combination thereof.

14. The applicator of claim 11, wherein the first transparent material comprises at least one of: polymethyl methacrylate (PMMA), a polycarbonate, a co-polyester, or any combination thereof.

15. The applicator of claim 14, wherein the second transparent material comprises at least one of a: co-polyester, polyethylene terephthalate, polycarbonate, polysulfone, leaded polymethyl methacrylate, glass, or any combination thereof.

16. The applicator of claim 11, wherein the first transparent material and the second transparent material comprise a same transparent material.

17. The applicator of claim 11, wherein the radiation source comprises at least one of a circular shape, a square shape, a rectangular shape, an obround shape, an elliptical shape, and a seed shape.

18. The applicator of claim 17, wherein the radiation source has a thickness which is less than a thickness of the body section.

19. The applicator of claim 11, wherein the radiation source comprises at least one of: $^{9}$Sr, $^{169}$Yb, $^{90}$Y, $^{192}$Ir, $^{103}$Pd, $^{177}$Lu, $^{149}$Pm, $^{140}$La, $^{153}$Sm, $^{186}$Re, $^{188}$Re, $^{166}$Ho, $^{166}$Dy, $^{137}$Cs, $^{57}$Co, $^{169}$Er, $^{165}$Dy, $^{97}$Ru, $^{193m}$Pt, $^{195m}$Pt, $^{105}$Rh, $^{68}$Ni, $^{67}$C, $^{64}$Cu, $^{109}$Cd, $^{111}$Ag, $^{198}$Au, $^{199}$Au, $^{201}$Tl, $^{175}$Yb, $^{47}$Sc, $^{159}$Gd, and $^{212}$Bi, or a combination thereof.

20. The applicator of claim 11, wherein the surface of the body section comprises at least one of a flat surface and a convex surface.

* * * * *